US012715899B2

(12) United States Patent
Kim et al.

(10) Patent No.: US 12,715,899 B2
(45) Date of Patent: Aug. 25, 2026

(54) PHARMACEUTICAL COMPOSITION FOR LOWERING BLOOD CHOLESTEROL, PREVENTING OR TREATING CARDIOVASCULAR DISEASES AND REDUCING INFLAMMATION

(71) Applicant: SEOUL NATIONAL UNIVERSITY HOSPITAL, Seoul (KR)

(72) Inventors: Hyo-Soo Kim, Seoul (KR); Hyun-Duk Jang, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 916 days.

(21) Appl. No.: 17/905,461

(22) PCT Filed: Aug. 14, 2020

(86) PCT No.: PCT/KR2020/010925

§ 371 (c)(1),
(2) Date: Sep. 1, 2022

(87) PCT Pub. No.: WO2021/177518

PCT Pub. Date: Sep. 10, 2021

(65) Prior Publication Data

US 2023/0159601 A1 May 25, 2023

(30) Foreign Application Priority Data

Mar. 2, 2020 (KR) ........................ 10-2020-0026073

(51) Int. Cl.

| | |
|---|---|
| ***C07K 14/47*** | (2006.01) |
| ***A61P 3/06*** | (2006.01) |
| ***C12N 15/113*** | (2010.01) |
| ***G01N 33/68*** | (2006.01) |

(52) U.S. Cl.
CPC ............ *C07K 14/4738* (2013.01); *A61P 3/06* (2018.01); *C12N 15/113* (2013.01); *G01N 33/6893* (2013.01); *C07K 2319/30* (2013.01)

(58) Field of Classification Search
CPC . C07K 7/16; A61P 29/00; A61P 25/04; A61K 38/00
See application file for complete search history.

(56) References Cited

U.S. PATENT DOCUMENTS

| | | | |
|---|---|---|---|
| 2012/0014973 | A1 | 1/2012 | Naparstek et al. |
| 2014/0072951 | A1 | 3/2014 | Johnson |

FOREIGN PATENT DOCUMENTS

| | | | |
|---|---|---|---|
| KR | 10-1473526 | B1 | 12/2014 |
| KR | 10-2018-0089253 | A | 8/2018 |
| KR | 10-2019-0007267 | A | 1/2019 |
| WO | 2004/034062 | A2 | 4/2004 |

OTHER PUBLICATIONS

Bowie et al (Science, 1990, 247: 1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Guo et al (PNAS, 2004, 101(25), 9205-9210) (Year: 2004).*
Yampolsky et al (Genetics, 2005, 170, 1459-1472) (Year: 2005).*
Jang et al., "Cyclase-associated protein 1 is a binding partner of proprotein convertase subtilisin/kexin type-9 and is required for the degradation of low-density lipoprotein receptors by proprotein convertase subtilisin/kexin type-9", European Heart Journal, online publish-ahead of-print published Aug. 16, 2019, 21 pages—Internet URL: https://doi.org/10.1093/eurheartj/ehz566.
Jang et al., "Cyclase-associated protein 1 is a binding partner of proprotein convertase subtilisin/kexin type-9 and is required for the degradation of low-density lipoprotein receptors by proprotein convertase subtilisin/kexin type-9", European Heart Journal, 2020, vol. 41, pp. 239-252. (Journal publication of Citation 1).
Yang, "Low Cholesterol level in CAP1-Knockout mice: CAP1 is an essential binding partner of PCSK9 to degrade LDLR", Dept. of Molecular Medicine and Biopharmaceutical Sciences, Ph.D. Thesis, Seoul National University Graduate School, 2017, 81 pages.

* cited by examiner

*Primary Examiner* — Sudhakar Katakam
(74) *Attorney, Agent, or Firm* — Vorys, Sater, Seymour and Pease LLP; Mih Suhn Koh

(57) ABSTRACT

The present invention relates to a pharmaceutical composition and the like for lowering blood cholesterol, preventing or treating cardiovascular diseases and reducing inflammation, containing, as an active ingredient, an inhibitor of binding between CAP1 and PCSK9, an inhibitor of binding between CAP1 and resistin, or a CAP1 gene expression inhibitor. The present invention can lower the level of blood LDL-cholesterol by inhibiting the binding of CAP1 and PCSK9, the binding of CAP1 and resistin or the expression of a CAP1 gene. Therefore, the present invention can be effectively used as a pharmaceutical composition and the like for treating abnormal blood cholesterol levels and various cardiovascular diseases caused thereby, such as dyslipidemia, stroke, arteriosclerosis, and the like, and for inhibiting inflammation.

8 Claims, 43 Drawing Sheets

Specification includes a Sequence Listing.

kD (Dissociation equilibrium constant)

PCSK9 WT : 0.45 μM

PCSK9 A514T : 0.11 μM

PCSK9 G670E : 0.96 μM

PCSK9 S668RG670E : 2.32 μM

FIG. 3G

PHARMACEUTICAL COMPOSITION FOR LOWERING BLOOD CHOLESTEROL, PREVENTING OR TREATING CARDIOVASCULAR DISEASES AND REDUCING INFLAMMATION

CROSS-REFERENCE TO RELATED APPLICATIONS

This application is a 371 of PCT/KR2020/010925 filed on Aug. 14, 2020, which claims the benefit of priority from Korean Patent Application No. 10-2020-0026073 filed on Mar. 2, 2020, the contents of each of which are incorporated herein by reference in its entirety.

SEQUENCE LISTING

The Sequence Listing submitted in text format (.txt) filed on Sep. 8, 2022, named "SequenceListing.txt", created on Sep. 6, 2022 (32.3 KB), is incorporated herein by reference.

TECHNICAL FIELD

The present invention relates to a pharmaceutical composition and the like for lowering blood cholesterol, preventing or treating cardiovascular diseases and reducing inflammation, containing, as an active ingredient, an inhibitor of binding between CAP1 and PCSK9, an inhibitor of binding between CAP1 and resistin, or a CAP1 gene expression inhibitor, and a composition and the like for diagnosing hypercholesterolemia or cardiovascular diseases, including a preparation that measures the level of binding between CAP1 and PCSK9 or resistin.

This application claims priority to and the benefit of Korean Patent Application No. 10-2020-0026073 filed in the Korean Intellectual Property Office on Mar. 2, 2020, and all the contents disclosed in the specification and drawings of that application are incorporated in this application.

BACKGROUND ART

Proprotein convertase subtilisin/kexin type-9 (PCSK9) determines the level of plasma LDL-cholesterol by regulating the internalization and lysosomal degradation of a low-density lipoprotein (LDL) receptor, and accordingly, has become a promising treatment target. PCSK9 inhibitors reduced plasma LDL-cholesterol levels and showed improved cardiovascular outcomes. However, the precise mechanism by which PCSK9 determines the fate of LDL receptors has not been clarified. An LDL receptor enters cells while being bound to LDL-cholesterol, and then separated from the LDL-cholesterol in endosomes, and thus recycled to the cell surface, whereas the LDL-cholesterol is sent to the lysosomes for degradation. In contrast, when bound to PCSK9, the LDL receptor is internalized and guided to lysosomes for degradation through an unknown mechanism. Although PCSK9 is a proteinase K-like serine protease, after autocatalytic cleavage, the terminal part of a pro-domain (amino acids 32-152) covers the catalytic triad to prevent additional proteolytic activity. It has been suspected that the catalytic domain of PCSK9 binds to the LDL receptor, and another part of PCSK9, that is, a cysteine-rich domain (CRD), interacts with a putative membrane-bound protein that escorts a protein complex toward lysosomal degradation.

Meanwhile, CAP1 is known to regulate the dynamics of actin filaments that are important for cell morphology, migration, and endocytosis, and previous results reported that CAP1 is a receptor for human resistin. However, it is completely unknown whether CAP1 interacts with PCSK9 or resistin to be involved in regulation of LDL-cholesterol levels in various cardiovascular diseases including dyslipidemia, stroke, arteriosclerosis and the like.

DISCLOSURE

Technical Problem

The present inventors found that CAP1 directly binds to PCSK9, which determines the fate of an LDL receptor, induces degradation of the receptor, and when the binding between CAP1 and PCSK9 or between CAP1 and resistin is suppressed, or the expression of CAP1 is suppressed, LDL receptor degradation can be inhibited to lower the level of LDL-cholesterol and simultaneously inflammation is suppressed, thereby completing the present invention.

Therefore, an object of the present invention is to provide a composition for lowering blood cholesterol, containing, as an active ingredient, an inhibitor of binding between adenylyl cyclase-associated protein 1 (CAP1) consisting of an amino acid sequence of SEQ ID NO: 1 and protein convertase subtilisin/kexin type-9 (PCSK9) consisting of an amino acid sequence of SEQ ID NO: 2.

Another object of the present invention is to provide a composition for lowering blood cholesterol, containing, as an active ingredient, an expression inhibitor of a CAP1 gene consisting of a base sequence encoding an amino acid sequence of SEQ ID NO: 1.

Still another object of the present invention is to provide a composition for preventing, ameliorating or treating cardiovascular diseases, including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii).

Yet another object of the present invention is to provide a pharmaceutical composition for reducing inflammation or a health functional food composition, containing, as an active ingredient, one or more selected from the group consisting of (i) an inhibitor of binding between CAP1 consisting of an amino acid sequence of SEQ ID NO: 1 and PCSK9 consisting of an amino acid sequence of SEQ ID NO: 2; (ii) an inhibitor of binding between CAP1 consisting of an amino acid sequence of SEQ ID NO: 1 and resistin consisting of an amino acid sequence of SEQ ID NO: 3; and (iii) an expression inhibitor of a CAP1 gene consisting of a base sequence encoding the amino acid sequence of SEQ ID NO: 1.

Yet another object of the present invention is to provide a composition for diagnosing hypercholesterolemia or cardiovascular diseases, including a preparation that measures the level of binding between CAP1 consisting of an amino acid sequence of SEQ ID NO: 1; and PCSK9 consisting of an amino acid sequence of SEQ ID NO: 2 or resistin consisting of an amino acid sequence of SEQ ID NO: 3.

Yet another object of the present invention is to provide a method for diagnosing hypercholesterolemia or cardiovascular diseases or a method for providing information for diagnosis, the method including: measuring the level of binding between CAP1 consisting of an amino acid sequence of SEQ ID NO: 1; and PCSK9 consisting of an amino acid sequence of SEQ ID NO: 2 or resistin consisting of an amino acid sequence of SEQ ID NO: 3.

Further, an object of the present invention is to provide a method for screening a therapeutic agent for hypercholesterolemia or cardiovascular diseases.

However, the technical objects which the present invention intends to achieve are not limited to the technical objects which have been mentioned above, and other technical objects which have not been mentioned will be apparently understood by a person with ordinary skill in the art to which the present invention pertains from the following description.

Technical Solution

To achieve the objects of the present invention, the present invention provides a pharmaceutical composition for lowering blood cholesterol, containing, as an active ingredient, an inhibitor of binding between adenylyl cyclase-associated protein 1 (CAP1) consisting of an amino acid sequence of SEQ ID NO: 1 and proprotein convertase subtilisin/kexin type-9 (PCSK9) consisting of an amino acid sequence of SEQ ID NO: 2.

In addition, the present invention provides a method for lowering blood cholesterol, the method including: a step of administering an inhibitor of binding between CAP1 consisting of an amino acid sequence of SEQ ID NO: 1 and PCSK9 consisting of an amino acid sequence of SEQ ID NO: 2 to a subject in need.

Furthermore, the present invention provides a use of an inhibitor of binding between CAP1 consisting of an amino acid sequence of SEQ ID NO: 1 and PCSK9 consisting of an amino acid sequence of SEQ ID NO: 2 for lowering blood cholesterol.

In addition, the present invention provides a use of an inhibitor of binding between CAP1 consisting of an amino acid sequence of SEQ ID NO: 1 and PCSK9 consisting of an amino acid sequence of SEQ ID NO: 2 for producing a drug used for lowering blood cholesterol or preventing or treating hypercholesterolemia.

In an exemplary embodiment of the present invention, the inhibitor of binding may be one or more selected from the group consisting of proteins, peptides, peptide mimetics, substrate analogs, aptamers and antibodies which specifically bind to CAP1 or PCSK9, but is not limited thereto.

In another exemplary embodiment of the present invention, the inhibitor of binding may be a fusion protein including: a CAP1 protein consisting of an amino acid sequence of SEQ ID NO: 1 or a fragment thereof; and an Fc fragment of an immunoglobulin heavy chain.

In still another exemplary embodiment of the present invention, the fusion protein may consist of an amino acid sequence of SEQ ID NO: 4 or 6, but is not limited thereto.

In yet another exemplary embodiment of the present invention, the inhibitor of binding may bind to one or more domains selected from the group consisting of a Src homology 3 (SH3) binding domain of CAP1 and a cysteine-rich domain (CRD) of PCSK9, but is not limited thereto.

In yet another exemplary embodiment of the present invention, the SH3 binding domain of CAP1 may include an amino acid sequence of SEQ ID NO: 10, but is not limited thereto.

In yet another exemplary embodiment of the present invention, the cysteine-rich domain of PCSK9 may consist of an amino acid sequence of SEQ ID NO: 11, but is not limited thereto.

In yet another exemplary embodiment of the present invention, the cysteine-rich domain of PCSK9 may include an M1 domain consisting of an amino acid sequence of SEQ ID NO: 12, but is not limited thereto.

In yet another exemplary embodiment of the present invention, the cysteine-rich domain of PCSK9 may include an M3 domain consisting of an amino acid sequence of SEQ ID NO: 13, but is not limited thereto.

In yet another exemplary embodiment of the present invention, the inhibitor of binding may specifically bind to a site including aspartic acid 34B present in the SH3 binding domain of CAP1, but is not limited thereto.

In yet another exemplary embodiment of the present invention, the inhibitor of binding may specifically bind to a site including lysine 494 present in the M1 domain of PCSK9, but is not limited thereto.

In yet another exemplary embodiment of the present invention, the inhibitor of binding may specifically bind to a site including arginine 659 present in the M3 domain of PCSK9, but is not limited thereto.

Further, the present invention provides a pharmaceutical composition for lowering blood cholesterol, containing, as an active ingredient, an expression inhibitor of a CAP1 gene consisting of a base sequence encoding an amino acid sequence of SEQ ID NO: 1.

Furthermore, the present invention provides a method for lowering blood cholesterol, the method including: a step of administering an expression inhibitor of a CAP1 gene consisting of a base sequence encoding an amino acid sequence of SEQ ID NO: 1 to a subject in need.

In addition, the present invention provides a use of an expression inhibitor of a CAP1 gene consisting of a base sequence encoding an amino acid sequence of SEQ ID NO: 1 for lowering blood cholesterol.

Furthermore, the present invention provides a use of an expression inhibitor of a CAP1 gene consisting of a base sequence encoding an amino acid sequence of SEQ ID NO: 1 for producing a drug used for lowering blood cholesterol or preventing or treating hypercholesterolemia.

In an exemplary embodiment of the present invention, the expression inhibitor may be one or more selected from the group consisting of antisense nucleotides, siRNA, shRNA, miRNA, ribozymes and PNA capable of complementarily binding to mRNA of the CAP1 gene, but is not limited thereto.

In another exemplary embodiment of the present invention, the expression inhibitor may be siRNA consisting of a base sequence of SEQ ID NO: 8, but is not limited thereto.

In still another exemplary embodiment of the present invention, the expression inhibitor may be shRNA consisting of a base sequence of SEQ ID NO: 9, but is not limited thereto.

In yet another exemplary embodiment of the present invention, the composition may suppress the degradation of a low-density lipoprotein (LDL) receptor.

In yet another exemplary embodiment of the present invention, the cholesterol may be LDL-cholesterol, but is not limited thereto.

Further, the present invention provides a health functional food composition for lowering blood cholesterol, including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii).

Further, the present invention provides a pharmaceutical composition for preventing or treating cardiovascular diseases or a health functional food for preventing or ameliorating cardiovascular diseases, including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii).

Furthermore, the present invention provides a method for preventing or treating cardiovascular diseases, the method including: a step of administering, to a subject in need, (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii).

In addition, the present invention provides a use of a composition including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii) for preventing or treating cardiovascular diseases.

Furthermore, the present invention provides a use of a composition including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii) for producing a drug used for preventing or treating cardiovascular diseases.

In an exemplary embodiment of the present invention, the inhibitor of binding may be one or more selected from the group consisting of proteins, peptides, peptide mimetics, substrate analogs, aptamers and antibodies which specifically bind to CAP1 or PCSK9, but is not limited thereto.

In another exemplary embodiment of the present invention, the inhibitor of binding may be a fusion protein including: a CAP1 protein consisting of an amino acid sequence of SEQ ID NO: 1 or a fragment thereof; and an Fc fragment of an immunoglobulin heavy chain.

In still another exemplary embodiment of the present invention, the fusion protein may consist of an amino acid sequence of SEQ ID NO: 4 or 6, but is not limited thereto.

In yet another exemplary embodiment of the present invention, the expression inhibitor may be one or more selected from the group consisting of antisense nucleotides, siRNA, shRNA, miRNA, ribozymes and PNA capable of complementarily binding to mRNA of the CAP1 gene, but is not limited thereto.

In yet another exemplary embodiment of the present invention, the expression inhibitor may be siRNA consisting of a base sequence of SEQ ID NO: 8, but is not limited thereto.

In yet another exemplary embodiment of the present invention, the expression inhibitor may be shRNA consisting of a base sequence of SEQ ID NO: 9, but is not limited thereto.

In yet another exemplary embodiment of the present invention, the cardiovascular disease may be a disease selected from the group consisting of diabetes, obesity, dyslipidemia, fatty liver, hypertension, gout, stroke, arteriosclerosis, myocardial infarction, angina pectoris, a peripheral vascular disease and a combination thereof, but is not limited thereto.

Further, the present invention provides a pharmaceutical composition for reducing inflammation, containing, as an active ingredient, one or more selected from the group consisting of (i) an inhibitor of binding between CAP1 consisting of an amino acid sequence of SEQ ID NO: 1 and PCSK9 consisting of an amino acid sequence of SEQ ID NO: 2; (ii) an inhibitor of binding between CAP1 consisting of an amino acid sequence of SEQ ID NO: 1 and resistin consisting of an amino acid sequence of SEQ ID NO: 3; and (iii) an expression inhibitor of a CAP1 gene consisting of a base sequence encoding the amino acid sequence of SEQ ID NO: 1.

In an exemplary embodiment of the present invention, the inhibitor of binding of (i) may be one or more selected from the group consisting of a protein, a peptide, a peptide mimetic, a substrate analog, an aptamer and an antibody specifically binding to PCSK9, but is not limited thereto.

In another exemplary embodiment of the present invention, the inhibitor of binding of (ii) may be one or more selected from the group consisting of a protein, a peptide, a peptide mimetic, a substrate analog, an aptamer and an antibody specifically binding to resistin, but is not limited thereto.

In still another exemplary embodiment of the present invention, the inhibitor of binding of (i) or (ii) may be a fusion protein including: a CAP1 protein consisting of an amino acid sequence of SEQ ID NO: 1 or a fragment thereof; and an Fc fragment of an immunoglobulin heavy chain.

In yet another exemplary embodiment of the present invention, the fusion protein may consist of an amino acid sequence of SEQ ID NO: 4 or 6, but is not limited thereto.

In yet another exemplary embodiment of the present invention, the expression inhibitor of (iii) may be one or more selected from the group consisting of antisense nucleotides, siRNA, shRNA, miRNA, ribozymes and PNA capable of complementarily binding to mRNA of the CAP1 gene, but is not limited thereto.

In yet another exemplary embodiment of the present invention, the composition may suppress the activity of NF-κB.

Further, the present invention provides a composition for diagnosing hypercholesterolemia or cardiovascular diseases, including a preparation that measures the level of binding between CAP1 consisting of an amino acid sequence of SEQ ID NO: 1; and PCSK9 consisting of an amino acid sequence of SEQ ID NO: 2 or resistin consisting of an amino acid sequence of SEQ ID NO: 3.

Further, the present invention provides a method for diagnosing hypercholesterolemia or cardiovascular diseases or a method for providing information for diagnosis, the method including: measuring the level of binding between CAP1 consisting of an amino acid sequence of SEQ ID NO: 1; and PCSK9 consisting of an amino acid sequence of SEQ ID NO: 2 or resistin consisting of an amino acid sequence of SEQ ID NO: 3.

In an exemplary embodiment of the present invention, a sample of the patient may be selected from the group consisting of liver tissue, liver cells, blood, serum, plasma, saliva, sputum and urine, but is not limited thereto.

Further, the present invention provides a method for screening a therapeutic agent for hypercholesterolemia or cardiovascular diseases, the method including: (a) a step of treating a test material to a sample including a CAP1 protein consisting of an amino acid sequence of SEQ ID NO: 1 or a fragment thereof; and a PCSK9 protein consisting of an amino acid sequence of SEQ ID NO: 2 or a fragment thereof, or a resistin protein consisting of an amino acid sequence of an amino acid sequence of SEQ ID NO: 3 or a fragment thereof with a test material; (b) a step of measuring the level of binding between the CAP1 or the fragment thereof; and the PCSK9 protein or the fragment thereof, or the resistin protein or the fragment thereof; and (c) a step of selecting the test material with a reduced binding level compared to a control sample.

In an exemplary embodiment of the present invention, the level of binding of Step (b) may be measured by any one selected from the group consisting of yeast two-hybrid, surface plasmon resonance (SPR), immunoprecipitation, radioactive immunoassay (RIA), enzyme-linked immunosorbent assay (ELISA), immunohistochemistry, western blotting and fluorescence activated cell sorting (FACS), but is not limited thereto.

Advantageous Effects

According to the present invention, cholesterol levels can be regulated by inhibiting the binding of CAP1, which directly binds to PCSK9 to regulate the life cycle of LDL receptors, to PCSK9 or resistin, or suppressing the expression of the CAP1 gene. Therefore, the inhibitor of binding between CAP1; and PCSK9 or resistin or the CAP1 gene expression inhibitor according to the present invention, and the like can lower the level of blood cholesterol, and accordingly, can be usefully used as a composition for treating various cardiovascular diseases associated with abnormal levels of blood cholesterol or caused thereby, and furthermore, can also show an effect of suppressing inflammation through suppression of NF-κB activation.

DESCRIPTION OF DRAWINGS

(FIG. 1A) Results of immunoprecipitation reaction of endogenous CAP1 or PCSK9 from liver lysates of C57/BL6 wild-type mice; (FIG. 1B) Results of far-western blot analysis of mFc-hCAP1 and HPSK9-His; (FIG. 1C) Results of bimolecular fluorescence complementation analysis visualizing the interaction between hCAP1 and hPCSK9 in living cells; (FIG. 1D) Results of immunofluorescent staining to confirm the co-localization of CAP1 and PCSK9 in HepG2 cells treated with exogenous recombinant hPCSK9 (over-lap coefficient: mean±standard deviation); (FIG. 1E) Results of direct binding analysis between rhPCSK9 and CAP1 using surface plasmon resonance (Dissociation equilibrium constant: 1.01 μM); (FIG. 1F) Results of co-immunoprecipitation reaction of hPSK9-Flag and wild-type CAP1 or each CAP1 variant in HEK293 cells; (FIG. 1G) Results of co-immunoprecipitation reaction of hPSK9-Flag and CAP1 SH3BD in HEK293 cells; (FIG. 1H) Results of co-immunoprecipitation reaction of wild-type PCSK9 or CRD-deleted PCSK9 variants with wild-type hCAP1 in HEK293 cells; (FIG. 1I) 3D molecular modeling of complexes using protein-protein docking simulations and binding energy score analysis.

(FIG. 2A) Schematic view of eight PCSK9-CRD single nucleotide variants known to be associated with LDL-cholesterol in human plasma; (FIG. 2B) Results of binding affinity experiments between loss-of-function variant of PCSK9 and CAP1; (FIG. 2C) Results of direct binding analysis for the interaction of wild-type PCSK9 and its variants with CAP1 using the BLItz system.

FIGS. 3A to 3J are views showing that CAP1 is essential for LDL receptor degradation by PCSK9: (FIG. 3A) View showing that the degradation of LDL receptors induced by PCSK9 is attenuated by CAP1 siRNA; (FIG. 3B) View illustrating the distribution of LDL receptors, PCSK9 and CAP1 after treatment with His-rhPCSK9 in HepG2 cells treated with CAP1 siRNA; (FIG. 3C) Results of measuring the degree of LDL receptor degradation by expression of wild-type CAP1 and each variant in CAP1-deficient cells; (FIG. 3D) View comparing CAP1 expression levels in each organ in $CAP1^{+/-}$ mice; (FIG. 3E) View comparing the expression levels of LDL receptor in $CAP1^{+/+}$ and $CAP1^{+/-}$ mice; (FIG. 3F) View measuring the plasma cholesterol levels in $CAP1^{+/-}$ and $CAP^{+/+}$ mice fed a high-fat diet or normal diet for 16 weeks; (FIG. 3G) View illustrating the cholesterol levels of FPLC fractions from pooled plasma samples in $CAP^{+/+}$ and $CAP^{+/-}$ mice fed a high-fat diet; (FIG. 3H) Results of western blot analysis for LDL receptor degradation induced by PCSK9 in the livers of $CAP1^{+/-}$ and $CAP1^{+/+}$ mice (P, pro-PCSK9; M, mature PCSK9); (FIG. 3I) Plasma hPCSK9 levels measured by ELISA; (FIG. 3J) Results of plasma cholesterol level analysis in $CAP1^{+/-}$ and $CAP1^{+/+}$ mice with or without PCSK9 overexpression.

(FIGS. 4A to 4C) Results of treating HepG2 cells with recombinant hPCSK9, and then performing a series of immunofluorescent staining with LDL receptor (green), PCSK9 (red) and endosomal marker EEA1 or lysosomal maker LAMP2 (white); (FIG. 4S) Schematic view of the LDL receptor undergoing caveolae-dependent endocytosis and PCSK9-induced lysosomal degradation.

(FIG. 5A) Western blot photograph confirming the phosphorylation pattern of p65 according to treatment with recombinant human resistin (rhResistin) and/or mFc-CAP1 at different concentrations; (FIG. 5B) Western blot photographs confirming the phosphorylation pattern of p65 according to treatment with PCSK9 and/or mFc-CAP1 at different concentrations.

(FIG. 6A) Western blot photograph (left side) confirming the expression level of LDL receptor and pAMPK and pACC levels according to treatment with recombinant human PSCK9 (rhPCSK9) and/or mFc-CAP1 at different concentrations (0.1, 1 μg/ml) and a graph (right side) quantifying the same with GAPDH; (FIG. 6B) Western blot photograph (left side) confirming the expression level of LDL receptor according to treatment with rhPCSK9 and/or mFc-CAP1 at different concentrations (0.01, 0.1, and 1 μg/ml) and a graph (right side) quantifying the same; (FIG. 6C) Western blot photograph (left side) confirming the expression level of LDL receptor, p-p65 and pAMPK levels according to treatment with rhResistin and/or mFc-CAP1 at different concentrations (50, 150, and 500 ng/ml) and graph (right side) quantifying the same with GAPDH; (FIG. 6D) Western blot photograph (left side) confirming the expression level of LDL receptor according to treatment with rhResistin and/or mFc-CAP1 at different concentrations (10, 50, and 500 ng/ml) and a graph (right side) quantifying the same; (FIG. 6E) Western blot photograph (left side) confirming the expression levels of pAMPK and LDL receptor according to treatment with rhResistin and/or mFc-CAP1 at different concentrations (50, 500 ng/ml) after stimulating AMPK with AICAR and graph (right side) quantifying the same normalized to GAPDH; (FIG. 6F) Western blot photograph (left side) confirming the expression level of LDL receptor according to treatment with rhResistin and/or mFc-CAP1 at different concentrations (50, 150, and 500 ng/ml) and a graph (right side) quantifying the same.

MODES OF THE INVENTION

Figure 1A:
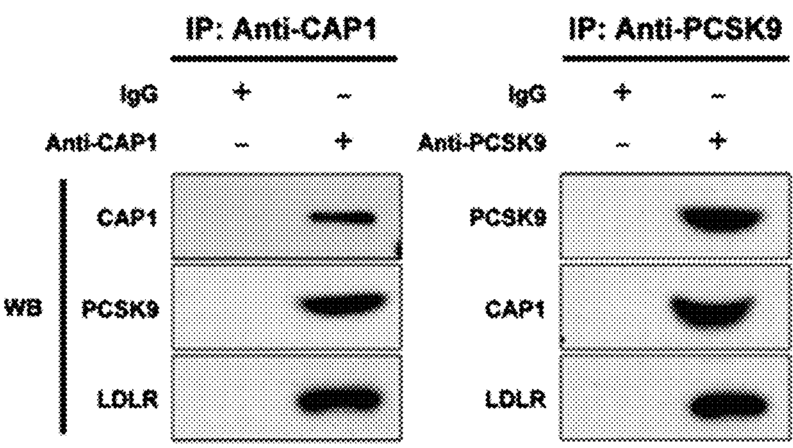
FIGS. 1A to 1I are views showing that CAP1 and PCSK9 directly interact with each other.
Figure 1A:
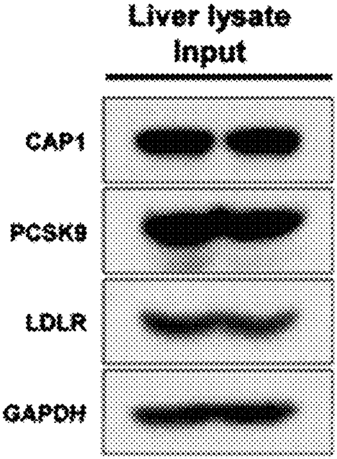

The present inventors have broadened our understanding of the endocytosis of LDL receptors by PCSK9 by identifying CAP1 as a new binding partner of PCSK9.

First, in an exemplary embodiment of the present invention, it was shown that the Src homology 3 binding domain (SH3BD) of CAP1 directly binds to a cysteine-rich domain (CRD) of PCSK9 (see Example 1).

In another exemplary embodiment of the present invention, it was confirmed that two loss-of-function polymorphisms found in human PCSK9 are defective in their interaction with CAP1 (see Example 2).

In still another exemplary embodiment of the present invention, it was confirmed that the degradation of a PCSK9-mediated LDL receptor was prevented in not only siRNA against CAP1 in hepatocytes, but also in heterozygous CAP1 knockout mice with low plasma LDL-cholesterol levels (see Example 3).

In yet another exemplary embodiment of the present invention, it was demonstrated that CAP1 binds to caveolin-1 and then directs the PCSK9-LDL receptor complex to caveolae-dependent endocytosis and lysosomal degradation (see Example 4).

In yet another exemplary embodiment of the present invention, mFc-CAP1 was prepared as a competitive inhibitor of CAP1 (see Example 5), and peripheral blood mononuclear cells and hepatocytes were treated with the mFc-CAP1 to confirm a protective effect on LDL receptors and an inhibitory effect on NF-κB associated with regulation of almost all inflammatory responses in the body (see Examples 6 and 7).

In yet another exemplary embodiment of the present invention, it was confirmed that the uptake of LDL cholesterol is suppressed when CAP1 is knocked down to suppress its expression (see Example 8).

Thus, the present invention provides a pharmaceutical composition for lowering blood cholesterol, containing, as an active ingredient, an inhibitor of binding between adenylyl cyclase-associated protein 1 (CAP1) consisting of an amino acid sequence of SEQ ID NO: 1 and proprotein convertase subtilisin/kexin type-9 (PCSK9) consisting of an amino acid sequence of SEQ ID NO: 2.

As used herein, the term CAP1 refers to 'adenylyl cyclase-associated protein 1', and may be divided into three domains in terms of structure and function. First, a highly conserved carboxyl-terminal domain binds to monomeric actin, and is essential for general cell morphology. Second, the amino-terminal domain of CAP1 interacts with adenyl cyclase in yeast. Third, a centrally-located proline-rich domain interacts with the Src homology 3 (SH3) domain of specific proteins. CAP1 according to the present invention includes, for example, an amino acid sequence represented by SEQ ID NO: 1, consists of the amino acid sequence represented by SEQ ID NO: 1, or may consist of an amino acid sequence having a sequence homology of 80% or more, more preferably 90% or more, and even more preferably 95% or more with the amino acid sequence of SEQ ID NO: 1. For example, CAP1 according to the present invention includes an amino acid sequence having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%. The % sequence homology to an amino acid sequence is confirmed by comparing a comparison region with an optimally aligned sequence, and a portion of the amino acid sequence in the comparison region may further include an addition or deletion (that is, a gap) compared to the reference sequence (without addition or deletion) for the optimal alignment of the sequence.

As used herein, the term PCSK9 refers to 'proprotein convertase subtilisin/kexin type-9', and a human PCSK9 gene is located on chromosome 1p32.3 and has a length of 25,378 bp. It includes 12 exons encoding 692 amino acids. The PCSK9 protein includes a signal peptide, a pro-domain, a catalytic domain, and a C-terminal cysteine-histidine-rich domain consisting of three modules (M1, M2 and M3). PCSK9 according to the present invention includes, for example, an amino acid sequence represented by SEQ ID NO: 2, consists of the amino acid sequence represented by SEQ ID NO: 2, or may consist of an amino acid sequence having a sequence homology of 80% or more, more preferably 90% or more, and even more preferably 95% or more with the amino acid sequence of SEQ ID NO: 2. For example, PCSK9 according to the present invention includes an amino acid sequence having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%. The meaning of % sequence homology to the amino acid sequence is as described above.

In the present invention, the binding inhibitor may be one or more selected from the group consisting of proteins, peptides, peptide mimetics, substrate analogs, aptamers and antibodies which specifically bind to CAP1 or PCSK9, but all materials capable of binding to CAP1 or PCSK9 to interfere with their interaction are included within the scope of the present invention.

As used herein, the term peptide mimetics refers to those that bind to the binding domain of CAP1 or PCSK9 to inhibit the binding between CAP1 and PCSK9. Peptide mimetics may be peptides or non-peptides, and may consist up of amino acids bound by non-peptide bonds, such as psi bonds. Further, peptide mimetics may be conformationally constrained peptides, cyclic mimetics, or cyclic mimetics including at least one exocyclic domain, binding moieties (binding amino acids) and active sites. Peptide mimetics may be novel small molecules which are structured similar to the secondary structural properties of CAP1 or PCSK9 proteins, can mimic the inhibitory properties of large molecules such as antibodies or water-soluble receptors, and can act with an effect comparable to natural antagonists.

As used herein, the term antibody refers to a proteinaceous molecule capable of specifically binding to antigenic sites of protein or peptide molecules, and such an antibody may be prepared by cloning each gene into an expression vector by a typical method to obtain a protein encoded by the marker gene and from the obtained protein by a typical method.

As used herein, the term aptamer refers to a nucleic acid molecule that has binding activity for a predetermined target molecule. The aptamer may be RNA, DNA, a modified nucleic acid or a mixture thereof and may be in a straight-chain or cyclic form, and in general, it is known that the shorter the sequence of the nucleotides constituting the aptamer, the easier the chemical synthesis and mass production, the better the cost, the easier the chemical modification, the better the in vivo stability, and the lower the toxicity.

In the present invention, the inhibitor of binding may be a fusion protein including: a CAP1 protein consisting of an amino acid sequence of SEQ ID NO: 1 or a fragment thereof; and an Fc fragment of an immunoglobulin heavy chain. The CAP1 protein may be a fragment capable of specifically binding to PCSK9, for example, a fragment capable of specifically binding to a cysteine-rich domain corresponding to the portion of amino acids 421 to 629 of PCKS9 represented by SEQ ID NO: 2, the fragment is a polypeptide including all or part of the SH3-binding domain of the CAP1 protein, and there is no limitation on the length of the polypeptide.

The Fc fragment may be derived from immunoglobulin heavy chains of mammals including humans, for example, monkeys, orangutans, chimpanzees, mice, dogs, cats, cows, pigs, horses, and the like, and may be preferably derived from immunoglobulin heavy chains of humans or mice, but is not limited thereto. The sequence of the Fc fragment may be used by appropriately changing/modifying the sequence within a limitation that a person with ordinary skill in the art of the present invention can achieve the purpose of inhibiting in vivo CAP1 from binding to PCSK9 or resistin and inhibiting the degradation of the LDL receptor which binds to PCSK9 or resistin instead of the in vivo CAP1 and is regulated by the PCSK9 or resistin.

Further, the Fc fragment may bind to the N-terminal portion of the CAP1 protein or preferably the C-terminal portion, and may be directly or indirectly linked via a peptide linker or hinge, which is widely known in the art of the present invention.

In addition, in the present invention, the fusion protein may be a CAP1 protein fused with the Fc fragment of a human immunoglobulin heavy chain or the Fc fragment of a mouse immunoglobulin heavy chain. In this case, the CAP1 protein fused with the Fc fragment of a human immunoglobulin heavy chain may consist of an amino acid sequence of SEQ ID NO: 4 or may be encoded by a base sequence of SEQ ID NO: 5. Furthermore, the CAP1 protein fused with the Fc fragment of a mouse immunoglobulin heavy chain may consist of an amino acid sequence of SEQ ID NO: 6 or may be encoded by a base sequence of SEQ ID NO: 7. The fusion protein also includes functional equivalents of the amino acid sequence represented by SEQ ID NO: 4 or 6 within the scope of the present invention, and the functional equivalent has, as a result of addition, substitution, or deletion of an amino acid, a sequence homology of at least 60% or more, preferably 70% or more, more preferably 80% or more, and most preferably 90% or more with the amino acid sequence, and refers to a polypeptide showing substantially the same activity as that of the amino acid sequence represented by SEQ ID NO: 4 or 6, and is not limited thereto as long as the amino acid sequence is an amino acid sequence capable of specifically binding to PCSK9.

The present inventors prepared a fusion protein (Fc-CAP1) in which the Fc fragment of an immunoglobulin heavy chain was conjugated to the human CAP1 protein, and directly observed the LDL receptor protective effect thereof, and accordingly, it was confirmed that the Fc-CAP1 can lower blood LDL-cholesterol levels.

In the present invention, the inhibitor of binding may bind to one or more domains selected from the group consisting of a Src homology 3 (SH3) binding domain of CAP1 and a cysteine-rich domain (CRD) of PCSK9.

In this case, the SH3-binding domain of CAP1 with which the inhibitor of binding interacts may consist of an amino acid sequence of SEQ ID NO: 10, but is not limited thereto, and for example, the amino acid sequence may specifically bind to an amino acid site including the Asp34B amino acid of the SH3 binding domain and having a length of 3-250, 3-200, 3-150, 3-100, 3-50, 3-25, 3-10, 3-7 or 3-5.

In the present invention, the inhibitor of binding may specifically bind to a site including Asp34B present in the SH3-binding domain of CAP1. For example, the inhibitor of binding may specifically bind to a site including Asp34B within the SH3-binding domain of CAP1 to inhibit binding to PCSK9.

Further, in the present invention, the CRD of PCSK9 may consist of an amino acid sequence of SEQ ID NO: 11. The CRD includes an M1 domain consisting of an amino acid sequence of SEQ ID NO:12 or an M3 domain consisting of an amino acid sequence of SEQ ID NO:13.

In addition, in the present invention, the inhibitor of binding may specifically bind to a site including lysine 494 present in the M1 domain of PCSK9. For example, the inhibitor of binding may specifically bind to a site including amino acid 494 of the amino acid sequence represented by SEQ ID NO: 2 to inhibit binding to PCSK9.

In this case, the M1 domain of PCSK9 to which the inhibitor of binding binds may include an amino acid sequence of SEQ ID NO: 12, but is not limited thereto, and the inhibitor of binding may specifically bind to, for example, an amino acid site including amino acid 42 (or amino acid 494 of the amino acid sequence represented by SEQ ID NO: 2) and having a length of 3-70, 3-60, 3-50, 3-40, 3-30, 3-25, 3-20, 3-15, 3-10, 3-7 or 3-5.

Furthermore, in the present invention, the inhibitor of binding may specifically bind to a site including arginine 659 present in the M3 domain of PCSK9. For example, the inhibitor of binding may specifically bind to a site including amino acid 659 of the amino acid sequence represented by SEQ ID NO: 2 to inhibit binding to PCSK9.

In this case, the M3 domain of PCSK9 to which the inhibitor of binding binds may include an amino acid sequence of SEQ ID NO: 13, but is not limited thereto, and the inhibitor of binding may specifically bind to, for example, an amino acid site including amino acid 56 (or amino acid 659 of the amino acid sequence represented by SEQ ID NO: 2) and having a length of 3-85, 3-75, 3-65, 3-55, 3-45, 3-35, 3-25, 3-20, 3-15, 3-10, 3-7 or 3-5.

As another aspect of the present invention, the present invention provides a pharmaceutical composition for lowering blood cholesterol, containing, as an active ingredient, an expression inhibitor of a CAP1 gene consisting of a base sequence encoding an amino acid sequence of SEQ ID NO: 1.

As still another aspect of the present invention, the present invention provides a health functional food composition for lowering blood cholesterol, including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii).

In the present invention, the expression inhibitor of the CAP1 gene may be one or more selected from the group consisting of antisense nucleotides, siRNA, shRNA, miRNA, ribozymes and PNA capable of complementarily binding to mRNA of the CAP1 gene, but is not limited thereto.

In the present invention, the suppression of expression includes suppression of transcription of the CAP1 gene and suppression of translation into protein. Further, the suppression of expression also includes not only the case in which gene expression is completely stopped, but also the case in which expression is reduced.

As used herein, the terms siRNA, shRNA and miRNA refer to nucleic acid molecules that primarily bind to mRNA transcribed from a target gene to inhibit translation of the mRNA in order to mediate RNA interference or gene silencing. The miRNA, siRNA and shRNA can suppress the expression of the target gene at the translational level, and thus may be used in an efficient gene knockdown or gene therapy method.

As used herein, the term antisense oligonucleotide refers to DNA or RNA including a nucleic acid sequence complementary to that of a particular mRNA, or derivatives thereof, and may exhibit an effect of binding to a complementary sequence within mRNA to inhibit the translation of mRNA to protein.

As used herein, the term ribozyme may suppress protein expression of a target gene by recognizing and site-specifically cleaving a specific nucleotide sequence within a target RNA molecule.

As used herein, the term PNA refers to a nucleic acid mimetic, for example, a DNA mimetic, and here, a deoxyribose phosphate backbone is substituted with a pseudopeptide backbone, and only original four nucleobases are maintained. A neutral backbone of PNA is known to provide a hybrid specific for DNA and RNA under conditions of low ionic strength, and may be used as an antisense or antigen preparation for sequence-specific regulation of gene expression by inducing transcriptional or translational suppression or suppressing replication.

In the present invention, the expression inhibitor may be siRNA consisting of a base sequence of SEQ ID NO: 8, shRNA consisting of a base sequence of SEQ ID NO: 9, or a mixture thereof, but the siRNA sequence or shRNA sequence may be used while being appropriately changed/modified within a limitation that a person with ordinary skill in the art of the present invention can achieve the purpose of inhibiting the expression (or knockdown) of the CAP1 gene.

In the present invention, the cholesterol may be LDL-cholesterol, but is not limited thereto. For example, the cholesterol may be total cholesterol including LDL-cholesterol.

In the present invention, the composition may suppress the degradation of a low-density lipoprotein (LDL) receptor. When the expression or activity of CAP1 is suppressed, the degradation of LDL receptors by PCSK9 is suppressed, and as a result, there is an effect of lowering blood LDL-cholesterol levels.

As yet another aspect of the present invention, the present invention provides a pharmaceutical composition for preventing or treating cardiovascular diseases or a health functional food for preventing or ameliorating cardiovascular diseases, including: (i) an inhibitor of binding between CAP1 consisting of an amino acid sequence of SEQ ID NO: 1 and PCSK9 consisting of an amino acid sequence of SEQ ID NO: 2; (ii) an expression inhibitor of a CAP1 gene consisting of a base sequence encoding the amino acid sequence of SEQ ID NO: 1; or (iii) a mixture of (i) and (ii).

In the present invention, the inhibitor of binding may be one or more selected from the group consisting of proteins, peptides, peptide mimetics, substrate analogs, aptamers and antibodies which specifically bind to CAP1 or PCSK9, but is not limited thereto.

In the present invention, the inhibitor of binding may be a fusion protein including: a CAP1 protein consisting of an amino acid sequence of SEQ ID NO: 1 or a fragment thereof; and an Fc fragment of an immunoglobulin heavy chain. Details on the fusion protein are as described above.

Further, in the present invention, the expression inhibitor may be one or more selected from the group consisting of antisense nucleotides, siRNA, shRNA, miRNA, ribozymes and PNA capable of complementarily binding to mRNA of the CAP1 gene, but is not limited thereto.

In the present invention, the expression inhibitor may be siRNA consisting of a base sequence of SEQ ID NO: 8, shRNA consisting of a base sequence of SEQ ID NO: 9, or a mixture thereof, but is not limited thereto.

In the present invention, the cardiovascular disease may be a disease selected from the group consisting of diabetes, obesity, dyslipidemia, fatty liver, hypertension, gout, stroke, arteriosclerosis, myocardial infarction, angina pectoris, a peripheral vascular disease and a combination thereof, but is not limited thereto as long as the cardiovascular disease is a case having an abnormal blood cholesterol level or caused thereby.

As yet another aspect of the present invention, the present invention provides a pharmaceutical composition for reducing inflammation, containing, as an active ingredient, one or more selected from the group consisting of (i) an inhibitor of binding between CAP1 consisting of an amino acid sequence of SEQ ID NO: 1 and PCSK9 consisting of an amino acid sequence of SEQ ID NO: 2; (ii) an inhibitor of binding between CAP1 consisting of an amino acid sequence of SEQ ID NO: 1 and resistin consisting of an amino acid sequence of SEQ ID NO: 3; and (iii) an expression inhibitor of a CAP1 gene consisting of a base sequence encoding the amino acid sequence of SEQ ID NO: 1.

In the present invention, the inhibitor of binding of (i) may be one or more selected from the group consisting of proteins, peptides, peptide mimetics, substrate analogs, aptamers and antibodies which specifically bind to PCSK9, the inhibitor of binding of (ii) may be one or more selected from the group consisting of proteins, peptides, peptide mimetics, substrate analogs, aptamers and antibodies which specifically bind to resistin, but are not limited thereto.

In the present invention, the inhibitor of binding of (i) or (ii) may be a fusion protein including: a CAP1 protein consisting of an amino acid sequence of SEQ ID NO: 1 or a fragment thereof; and an Fc fragment of an immunoglobulin heavy chain. The fusion protein may consist of an amino acid sequence of SEQ ID NO: 4 or 6, but is not limited thereto.

Further, in the present invention, the expression inhibitor of (iii) may be one or more selected from the group consisting of antisense nucleotides, siRNA, shRNA, miRNA, ribozymes and PNA capable of complementarily binding to mRNA of the CAP1 gene, but is not limited thereto.

In the present invention, the composition may suppress the activity of NF-κB.

Meanwhile, the pharmaceutical composition according to the present invention may further include a suitable carrier, excipient and/or diluent which are/is typically used for preparation of a pharmaceutical composition in addition to the active ingredient. In addition, the pharmaceutical composition may be used by being formulated in the form of an oral formulation such as a powder, granules, a tablet, a capsule, a suspension, an emulsion, a syrup, and an aerosol, an external preparation, a suppository, and a sterile injection solution, according to a typical method.

Examples of the carrier, the excipient, and the diluent, which may be included in the composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. When the composition is prepared, the composition may be prepared using a commonly used diluent or excipient, such as a filler, an extender, a binder, a wetting agent, a disintegrant, and a surfactant.

The pharmaceutical composition according to the present invention is administered in a pharmaceutically effective amount. In the present invention, pharmaceutically effective amount means an amount sufficient to treat diseases at a reasonable benefit/risk ratio applicable to medical treatment, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field.

In consideration of all the aforementioned factors, it is important to administer the composition in a minimum amount that can obtain the maximum effect without any side effects, and this amount may be determined by those skilled in the art. Specifically, the effective amount of the pharmaceutical composition according to the present invention may vary depending on the age, sex, condition, and body weight of a patient, the absorption rate, inactivation rate and excretion rate of the active ingredient in vivo, the type of the disease, and the drug to be used in combination.

The pharmaceutical composition of the present invention may be administered to an subject via various routes. For example, the pharmaceutical composition may be administered, for example, by oral administration, intranasal administration, transtracheal administration, arterial injection, intravenous injection, subcutaneous injection, intramuscular injection, or intraperitoneal injection. The daily dosage may be administered once or in several divided doses per day.

As used herein, the term subject in need refers to a subject in need of prevention and treatment of a disease, enhancement of treatment, or suppression of resistance. For example, the subject in need may be a human or a mammal, including a non-human primate, a mouse, a dog, a cat, a horse, a sheep and a cow.

As used herein, the "prevention" refers to all actions that suppress or delay the onset of a target disease, and the "treatment" refers to all actions that ameliorate or beneficially change a target disease and the resulting metabolic abnormalities by administration of the pharmaceutical composition according to the present invention, and the "amelioration" refers to all actions that reduce a target disease and associated parameters, for example, the severity of symptoms, by administration of the composition according to the present invention.

In the present invention, the composition according to the present invention may be prepared as a food composition, and the food composition may be used by adding an active ingredient to food as it is or with other food or food ingredients, and may be used appropriately by typical methods. The mixing amount of the active ingredient may be suitably determined depending on its purpose of use (for prevention or alleviation).

Other ingredients are not particularly limited, except that the food composition includes the active ingredient as an essential ingredient at an indicated ratio, and the food composition may contain various flavoring agents, natural carbohydrates, and the like as an additional ingredient as in a typical beverage. Examples of the above-described natural carbohydrate include typical sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavoring agent other than those described above, a natural flavoring agent (thaumatin, a *stevia* extract, for example, rebaudioside A, glycyrrhizin and the like), and a synthetic flavoring agent (saccharin, aspartame and the like) may be advantageously used. The proportion of the natural carbohydrate may be appropriately determined by the choice of a person skilled in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The proportion of these additives may also be appropriately selected by a person skilled in the art.

The food composition of the present invention may include a health functional food.

As used herein, the term "health functional food" refers to a food prepared and processed in the form of a tablet, capsule, powder, granule, liquid, pill, and the like using raw materials or ingredients that have functionality useful to the human body. Here, functionality means that useful effects for health applications such as regulating nutrients and physiological actions are obtained for the structure and function of the human body. The health functional food of the present invention can be prepared by a method typically used in the art, and may be prepared by adding raw materials and components typically added in the art during preparation. Furthermore, since the health functional food has an advantage of having no side effects which may occur when the drug is taken for a long period of time because food is used as a raw material unlike general drugs, and may be excellent in portability, the health functional food of the present invention can be ingested as a supplement for enhancing anti-metabolic disease effects.

The health functional food of the present invention includes an inhibitor of binding between CAP1 and PCSK9 or resistin or a CAP1 gene expression inhibitor, and may further include an appropriate food supplement.

As yet another aspect of the present invention, the present invention provides a composition for diagnosing hypercholesterolemia or cardiovascular diseases, including a preparation that measures the level of binding between CAP1 consisting of an amino acid sequence of SEQ ID NO: 1; and PCSK9 consisting of an amino acid sequence of SEQ ID NO: 2 or resistin consisting of an amino acid sequence of SEQ ID NO: 3. In the present specification, it was confirmed that when the binding of CAP1 and PCSK9 was increased, the degradation of LDL receptors was also increased, resulting in high blood cholesterol levels, and conversely, when the binding of CAP1 and resistin is interfered with by Fc-CAP1, the degradation of the LDL receptor is decreased and the level of blood cholesterol is decreased, so that the case where a level of binding higher than that of a normal control is shown when the level of binding between CAP1 and PCSK9 or the level of binding between CAP1 and resistin is measured may be diagnosed as hypercholesterolemia or a cardiovascular disease.

As yet another aspect of the present invention, the present invention provides a method for diagnosing hypercholesterolemia or cardiovascular diseases or a method for providing information for diagnosis, the method including: measuring the level of binding between CAP1 consisting of an amino acid sequence of SEQ ID NO: 1; and PCSK9 consisting of an amino acid sequence of SEQ ID NO: 2 or resistin consisting of an amino acid sequence of SEQ ID NO: 3.

In the present invention, a sample of the patient may be selected from the group consisting of liver tissue, liver cells, blood, serum, plasma, saliva, sputum and urine, but is not limited thereto.

As yet another aspect of the present invention, the present invention provides a method for screening a therapeutic agent for hypercholesterolemia or cardiovascular diseases, the method including: (a) a step of treating test material into a sample including a CAP1 protein consisting of an amino acid sequence of SEQ ID NO: 1 or a fragment thereof; and a PCSK9 protein consisting of an amino acid sequence of SEQ ID NO: 2 or a fragment thereof, or a resistin protein consisting of an amino acid sequence of an amino acid sequence of SEQ ID NO: 3 or a fragment thereof with a test material; (b) a step of measuring the level of binding between the CAP1 or the fragment thereof; and the PCSK9 protein or the fragment thereof, of the resistin protein or the fragment thereof; and (c) a step of selecting the test material with a reduced binding level compared to a control sample.

In the present invention, the level of binding of Step (b) may be measured by any one selected from the group consisting of yeast two-hybrid, surface plasmon resonance (SPR), immunoprecipitation, radioactive immunoassay (RIA), enzyme-linked immunosorbent assay (ELISA), immunohistochemistry, western blotting and fluorescence activated cell sorting (FACS), but is not limited thereto as long as the method can measure the level of binding between CAP1 and PCSK9.

Terms or words used in the specification and the claims should not be interpreted as being limited to typical or dictionary meanings and should be interpreted with a meaning and a concept that are consistent with the technical spirit of the present invention based on the principle that an inventor can appropriately define a concept of a term in order to describe his/her own invention in the best way.

Hereinafter, preferred examples for helping with understanding of the present invention will be suggested. However, the following examples are provided only so that the present invention may be more easily understood, and the content of the present invention is not limited by the following examples.

EXAMPLES

Example 1. CAP1 Directly Binds to Cysteine-Rich Domain (CRD) of PCSK9

Figure 1B:
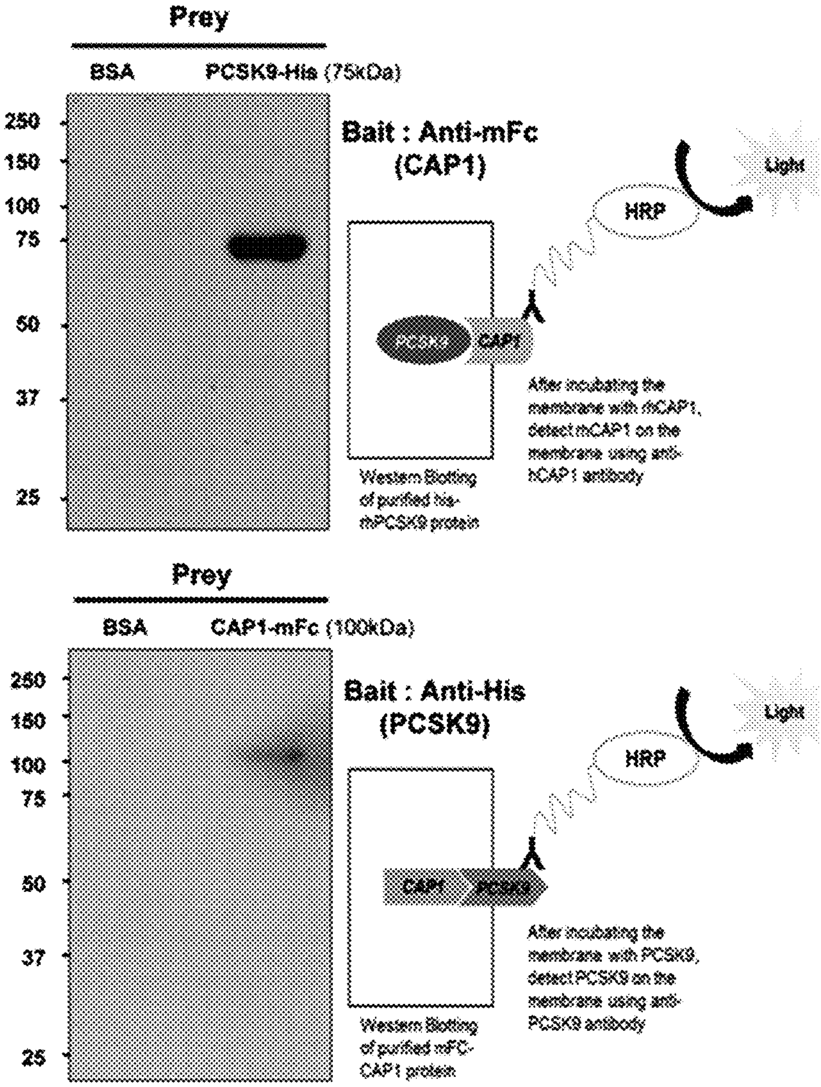
Figure 1C:
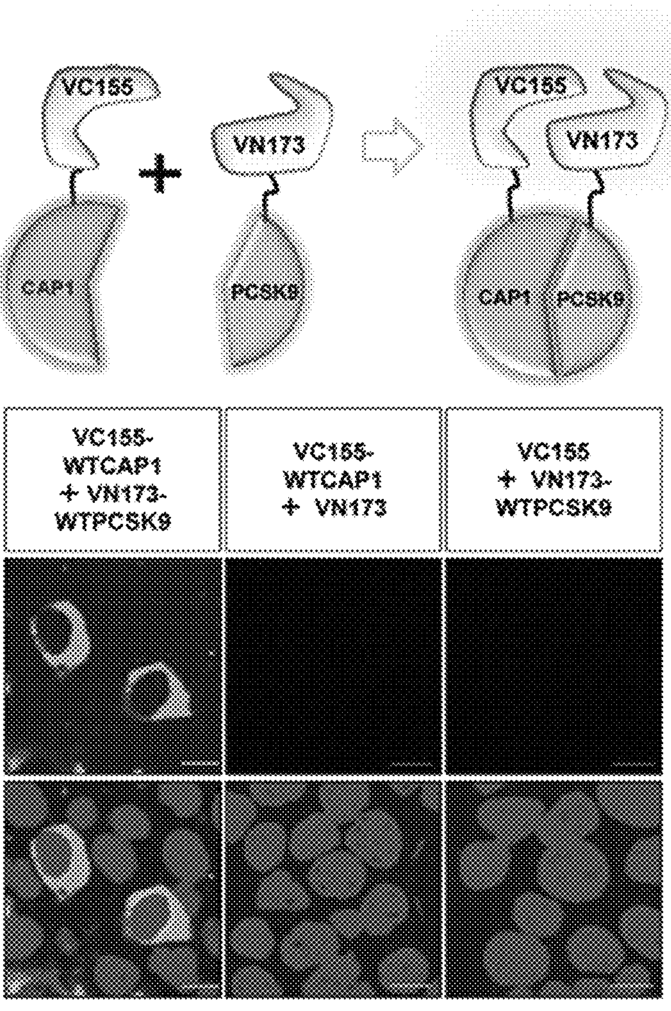

A physical interaction between CAP1 and PCSK9 was confirmed using immunoprecipitation in mouse liver tissues (FIG. 1A). For far-western blot analysis, mFc-CAP1 or His-PCSK9 purified under non-reducing conditions were used as prey, and His-PCSK9 or mFc-CAP1 was used as bait for each (FIG. 1B). To visualize the interaction described above in living cells, a bimolecular fluorescence complementation assay based on complementarity between two non-fluorescent fragments of fluorescent proteins brought together by interactions between the proteins fused to each fragment was performed. Through this, a direct binding between hCAP1 and hPCSK9 was clearly visualized. As illustrated in FIG. 1C, green fluorescence was observed when CAP1 and PCSK9 were fused to their respective fragments (pVC155 and pVN173) and both were expressed (left panel). However, no fluorescence was detected when human CAP1 or PCSK9 were expressed alone (middle and right panels, respectively).

Figure 1D:
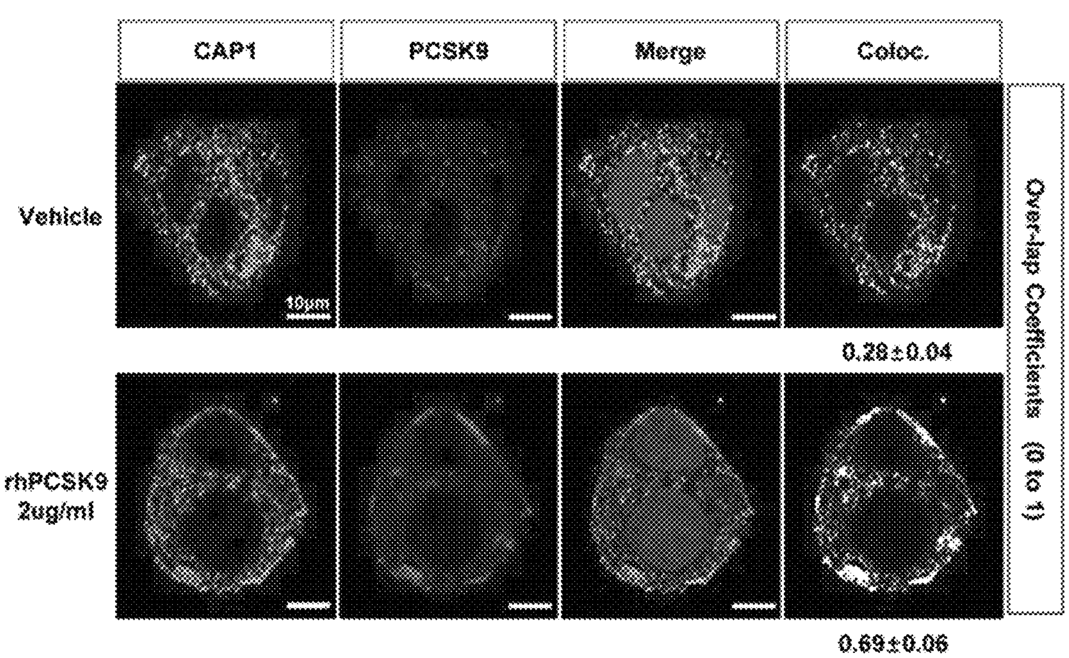
Figure 1E:
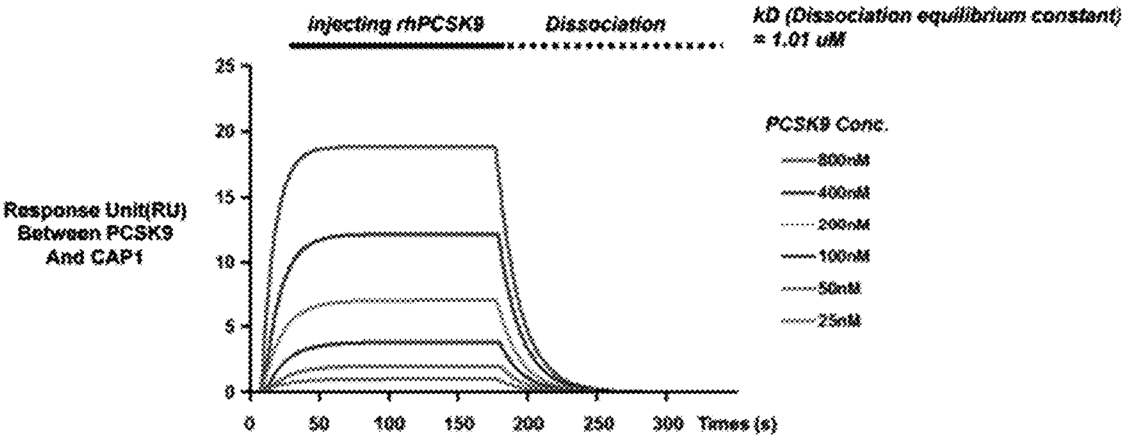

In addition, through immunofluorescent staining, it was demonstrated that PCSK9 was localized along with CAP1 and the LDL receptor in the plasma membrane and cytosol when HepG2 cells were treated with recombinant PCSK9 (FIG. 1D). Finally, as a result of performing direct binding analysis using a surface plasmon resonance-based system, it was confirmed that a response unit between CAP1 and PCSK9 was increased in a dose-dependent manner of PCSK9 (FIG. 1E).

Furthermore, the present inventors tested whether the CRD of PCSK9 binds to the Src homology 3 binding domain (SH3BD) of CAP1. For this purpose, an in vitro co-immunoprecipitation assay was performed using wtPCSK9-Flag and the following CAP1 variants: an adenylyl cyclase binding domain deletion (ΔACBD) variant, an actin-binding domain deletion (ΔActinBD) variant and a SH3BD and ActinBD deletion (ΔSH3BD ΔActinBD) variant.

Figure 1F:
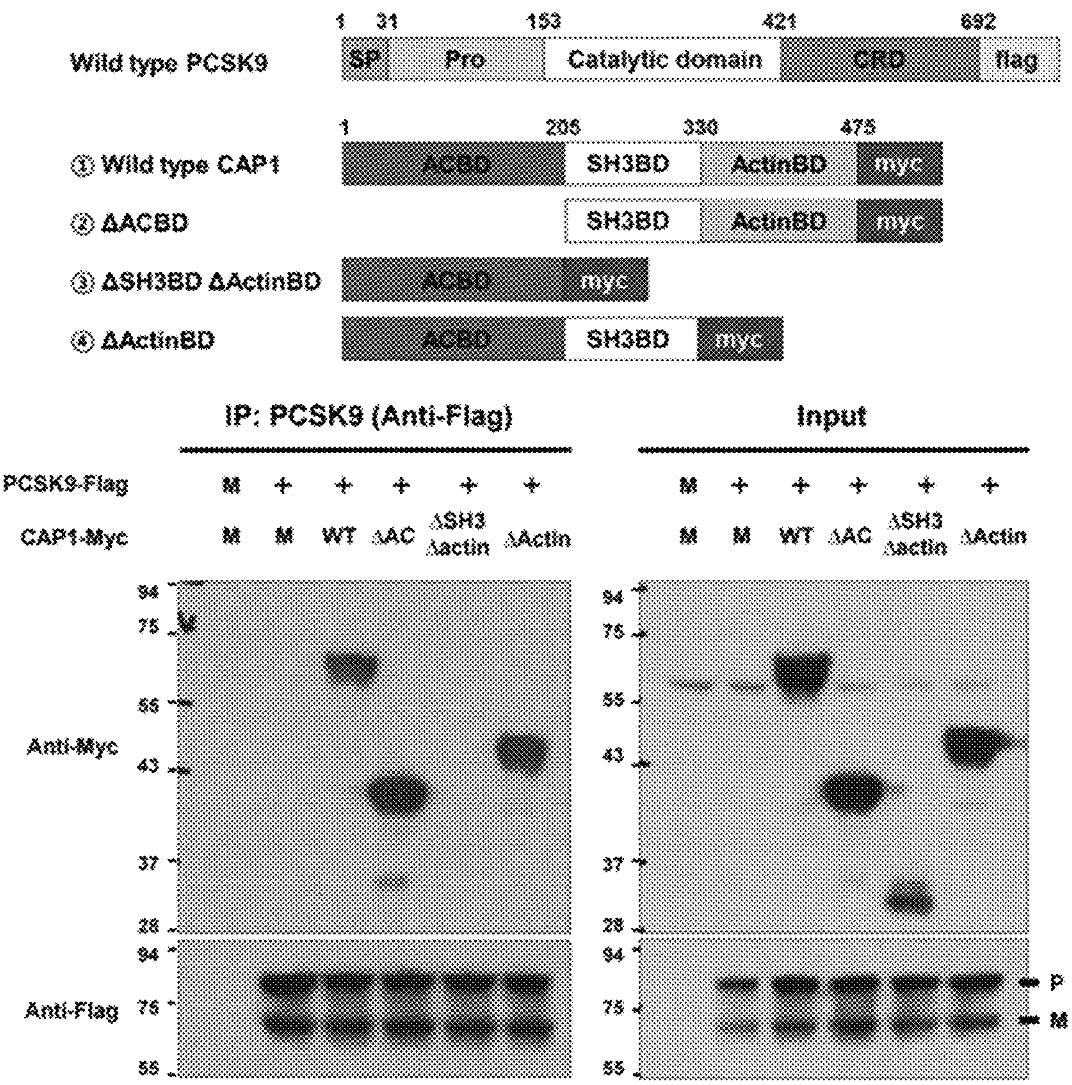
Figure 1G:
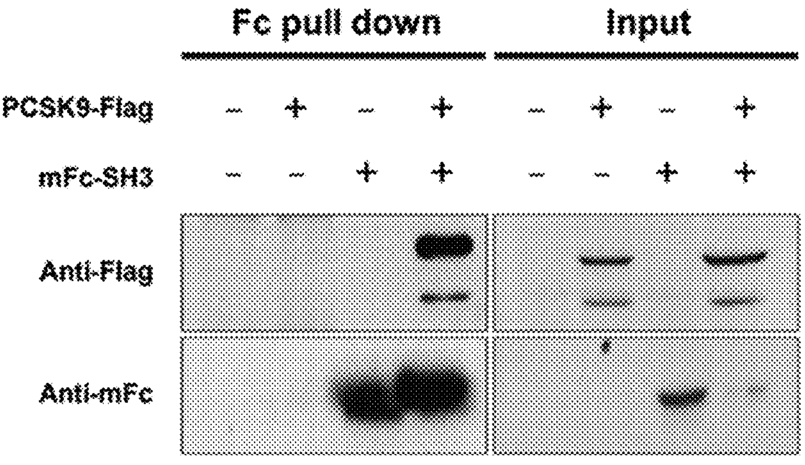
Figure 1H:
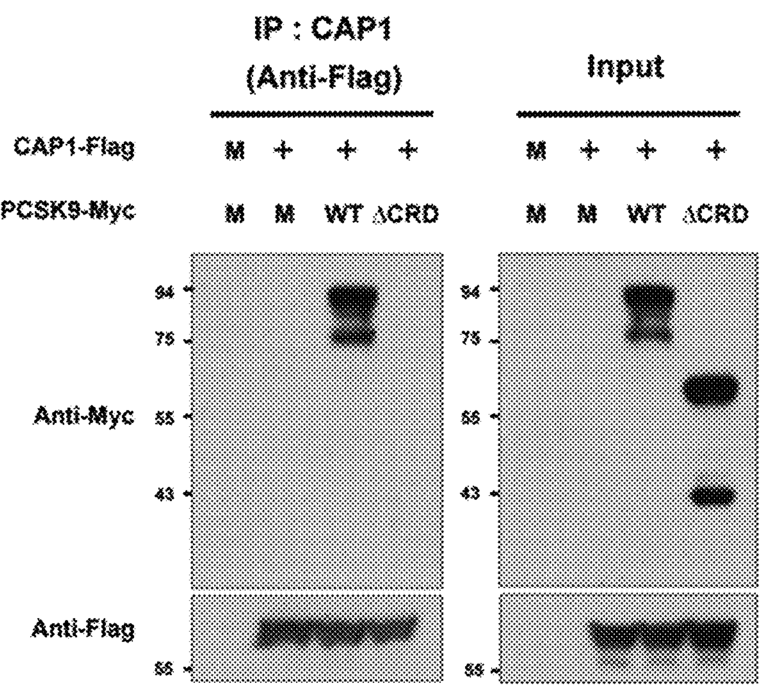

As a result, as illustrated in FIG. 1F, PCSK9 interacted with wtCAP1, the ΔACBD variant and the ΔActinBD variant, but did not interact with the ΔSH3BD ΔActinBD variant, suggesting that CAP1 binds to PCSK9 through SH3BD. Further, as illustrated in FIG. 1G it was confirmed that SH3BD of CAP1 is sufficient for interaction with PCSK9. CAP1 bound to wtPCSK9, but not to CRD-deleted PCSK9 (FIG. 1H).

Figure 1I:
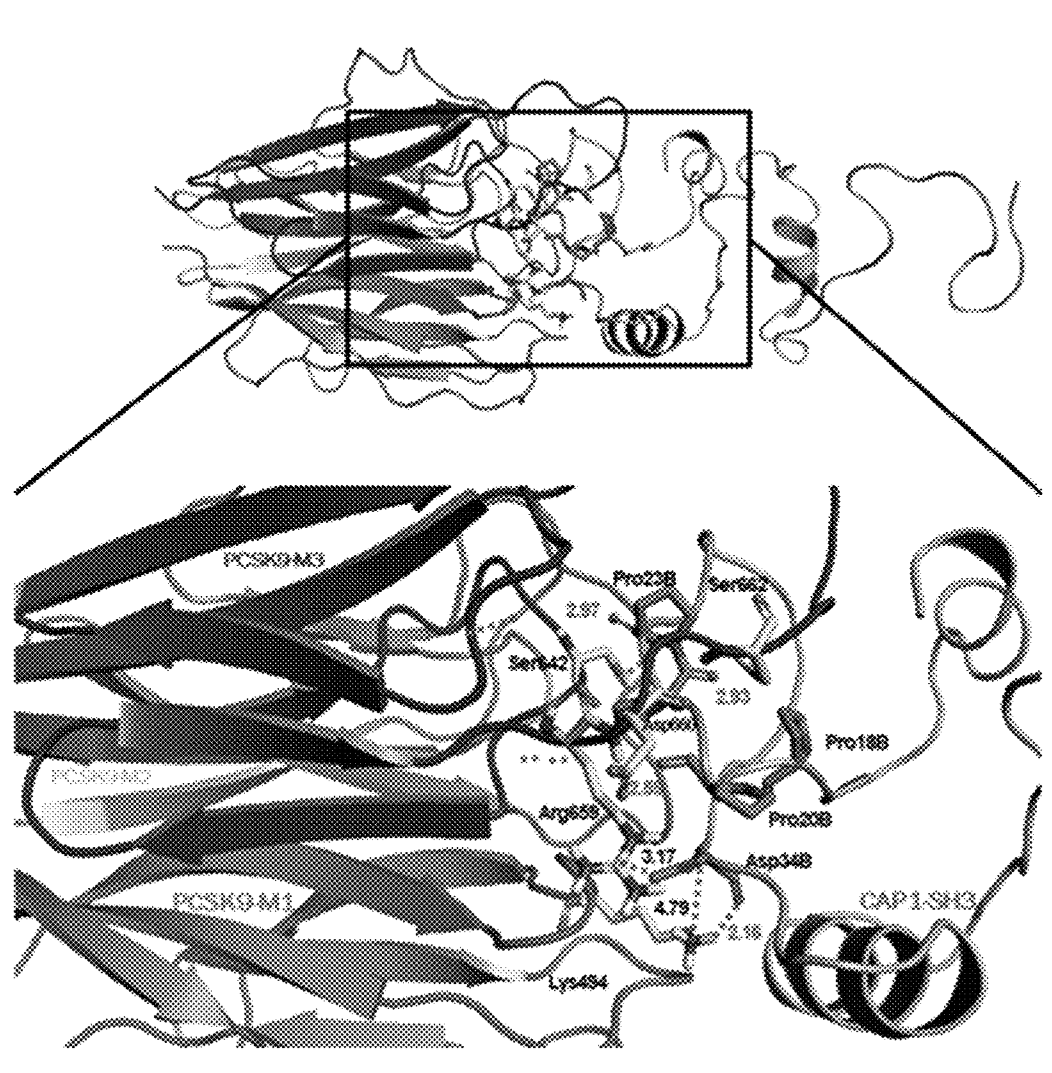

Furthermore, as illustrated in FIG. 1I, through the 3D molecular modeling analysis of a complex using a protein-protein docking simulation and a binding energy score analysis, it was confirmed that the interaction between Asp34B present in the SH3BD of CAP1 and Lys494 present in the M1 domain of PCSK9-CRD and Arg659 present in the M3 domain is important.

Example 2. PCSK9 Loss-of-Function Variants are Unable to Interact with CAP1

Figure 2A:
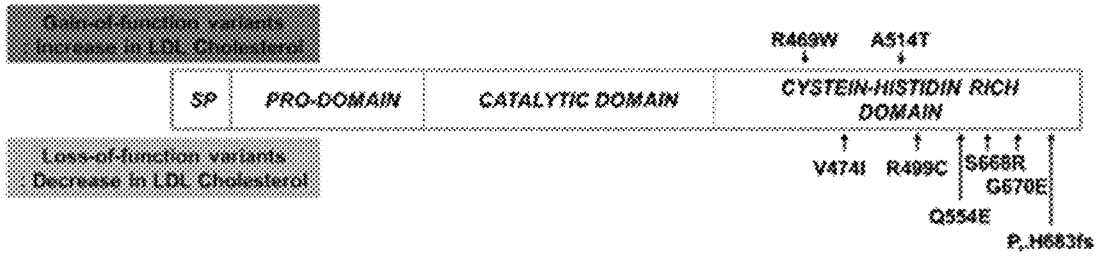
FIGS. 2A to 2C are views illustrating the results of experiments using loss-of-function variants of PCSK9.

The present inventors produced eight PCSK9 point mutants by site-directed mutagenesis of the PCSK9-CRD including well-known loss-of-function and gain-of-function mutations discovered in human genetic studies (FIG. 2A; arrows indicate points of point mutagenesis). The Q544E and H683fs variants of PCSK9 were not expressed in HepG2 cells, suggesting that these variants are associated with protein expression or stability.

Figure 2B:
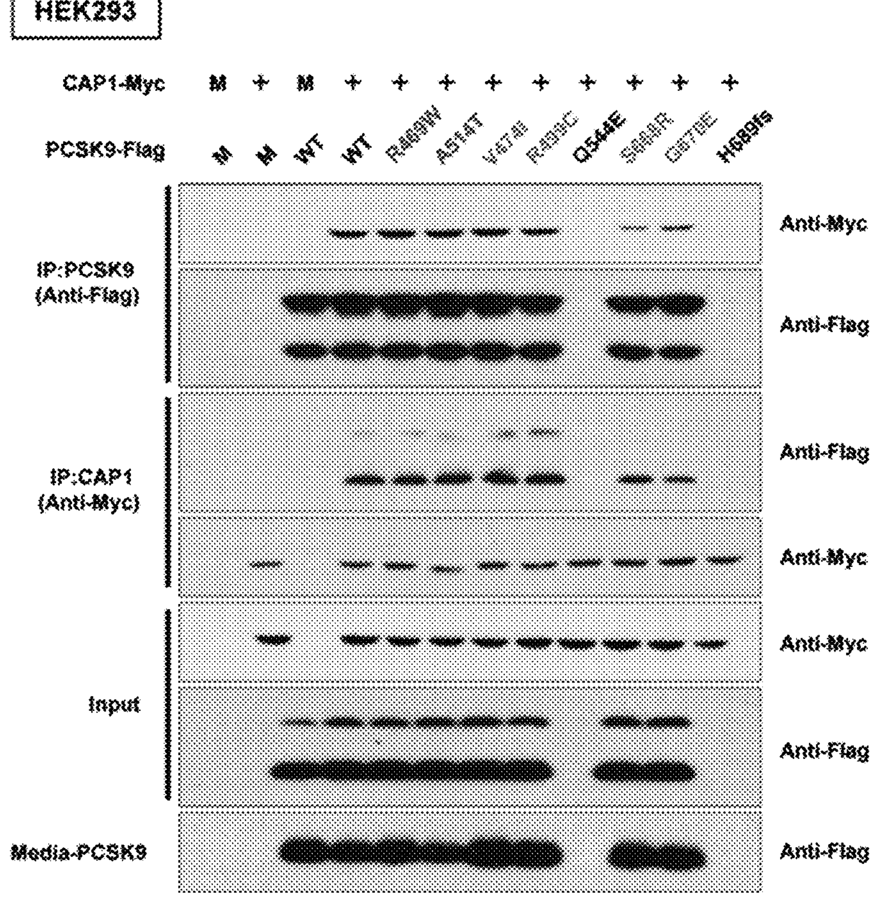

In contrast, as illustrated in FIG. 2B, it was confirmed by immunoprecipitation that the S668R and G670E variants of PCSK9 CRD were well expressed, but their ability to bind to CAP1 was severely impaired. These results suggest that the CRD of PCSK9 is important in binding to CAP1 and is important in regulating levels of the LDL receptor protein, that is, LDL-cholesterol.

Figure 2C:
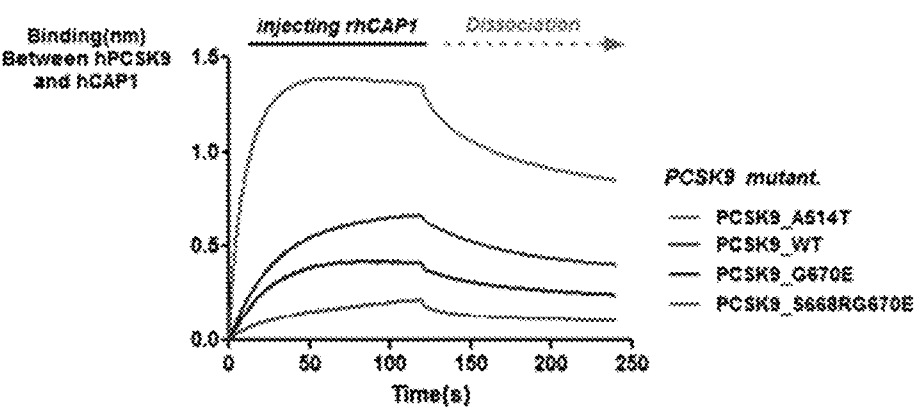

To examine additional features about the direct interaction between PCSK9-CRD mutations and CAP1, the present inventors measured the binding affinities of PCSK9 WT, PCSK9 A514T, PCSK9 G670E and PCSK9 S668RG670E to CAP1 using a BLITz system (Molecular Devices, LLC., USA). As a result, as illustrated in FIG. 2C, PCSK9 A514T exhibited a stronger interaction than the wild type (WT), whereas the G670E and G670ES668R variants exhibited a weaker interaction.

Example 3. CAP1 Induces PCSK9-Mediated LDL Receptor Degradation and Increases Levels of LDL-Cholesterol 3.1. Study of CAP1 Expression Suppression Effect Using siRNA PCSK9 treatment in HepG2 cells promotes the degradation of the LDL receptor in a dose-dependent manner. The present inventors suppressed the expression of a CAP1 gene using siRNA in order to examine the effect of CAP1 expression suppression on the degradation of the LDL receptor. The siRNA sequence is as follows:

```
CAP1 siRNA,
                                    (Seq ID NO: 8)
5'-AAACCGAGUCCUCAAAGAGUA-3'.
```

Figure 3A:
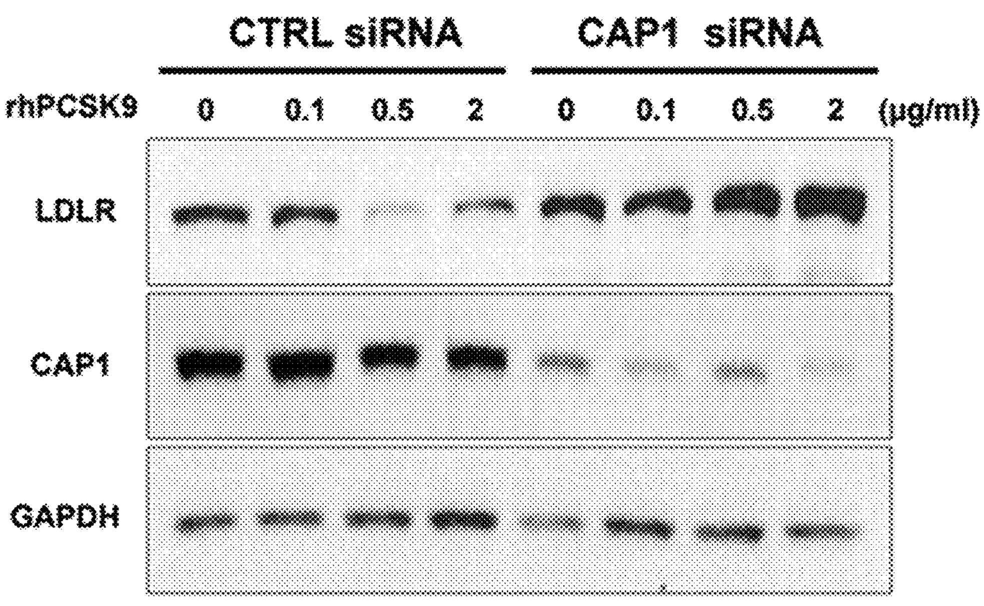
Figure 3A:
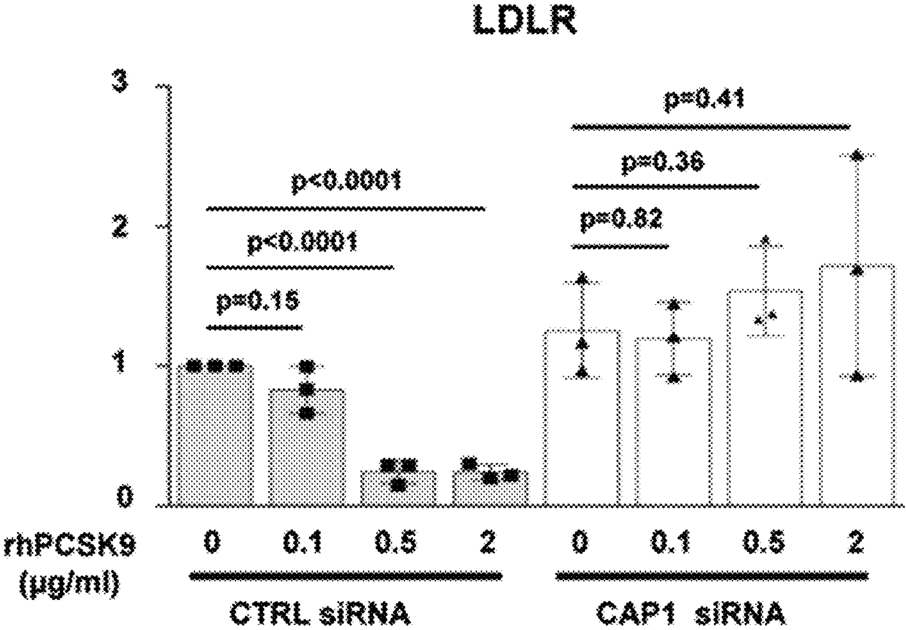
Figure 3B:
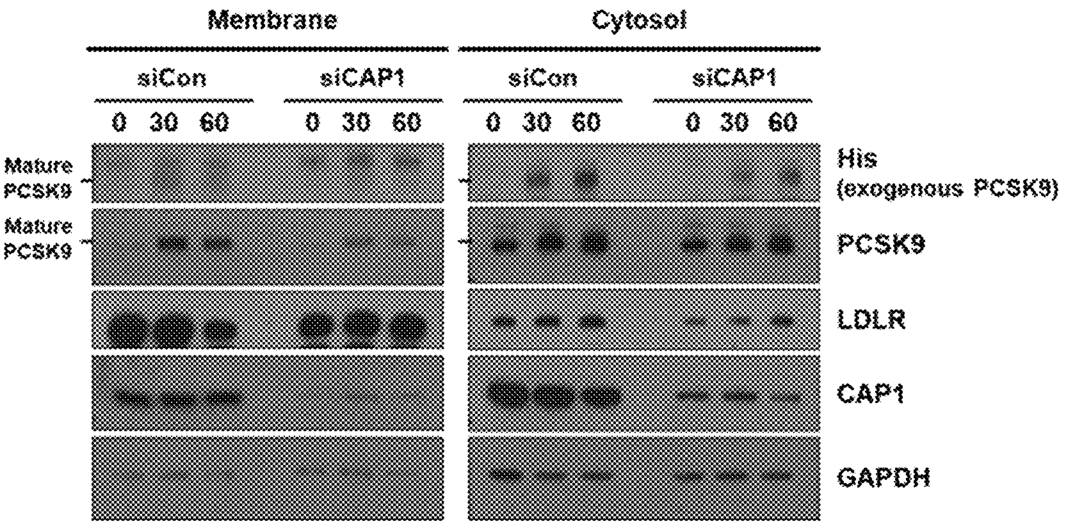

As a result, as illustrated in FIG. 3A, when CAP1 was depleted by siRNA (siCAP1), the degradation of the LDL receptor by exogenous PCSK9 was also significantly reduced. In addition, the results illustrated in FIG. 3B demonstrate that less LDL receptor and exogenous His-tagged PCSK9 were detected at both 30 or 60 min after His-rhPCSK9 treatment in the cytosol of CAP1siRNA-treated cells.

Figure 3C:
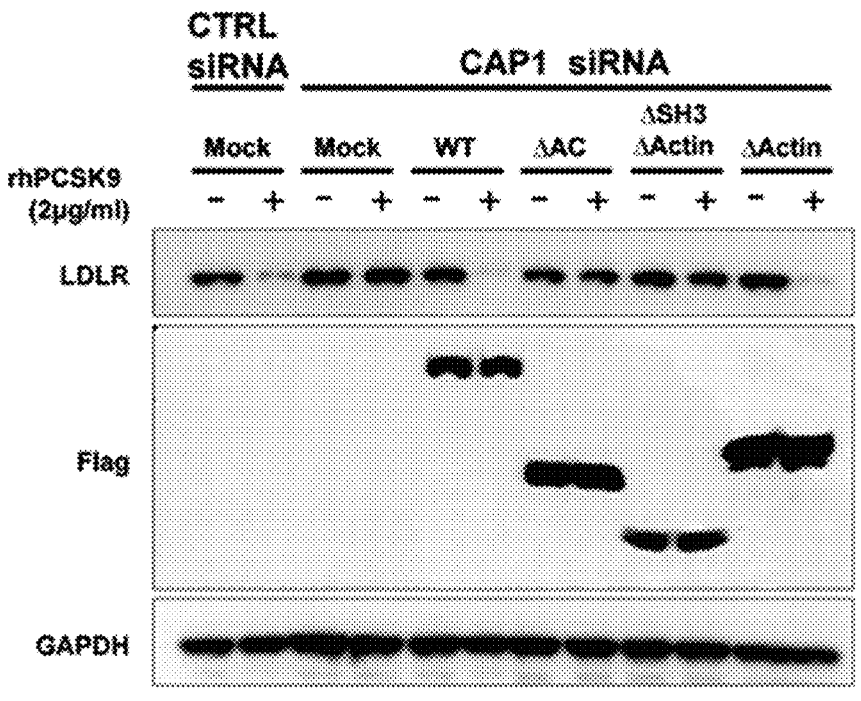
Figure 3C:
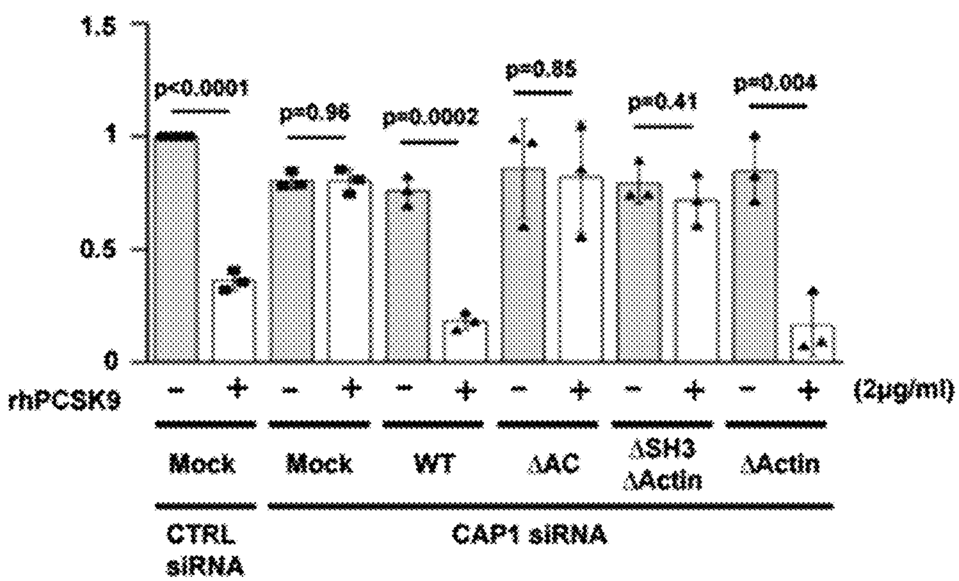

The present inventors rescued CAP1-deficient cells (si-CAP1) having wtCAP1 or each CAP1 variant by overexpression, and investigated PCSK9-mediated LDL receptor degradation. As a result, as illustrated in FIG. 3C, only wtCAP1 and the ΔactinBD variant rescued the attenuated PCSK9-mediated LDL receptor degradation, and the results suggest that SH3BD and ACBD are important in PCSK9-mediated LDL receptor degradation.

3.2. Study of LDL Receptor Degradation Effect of CAP1 Using CAP1 Knockout Mice

Figure 3D:
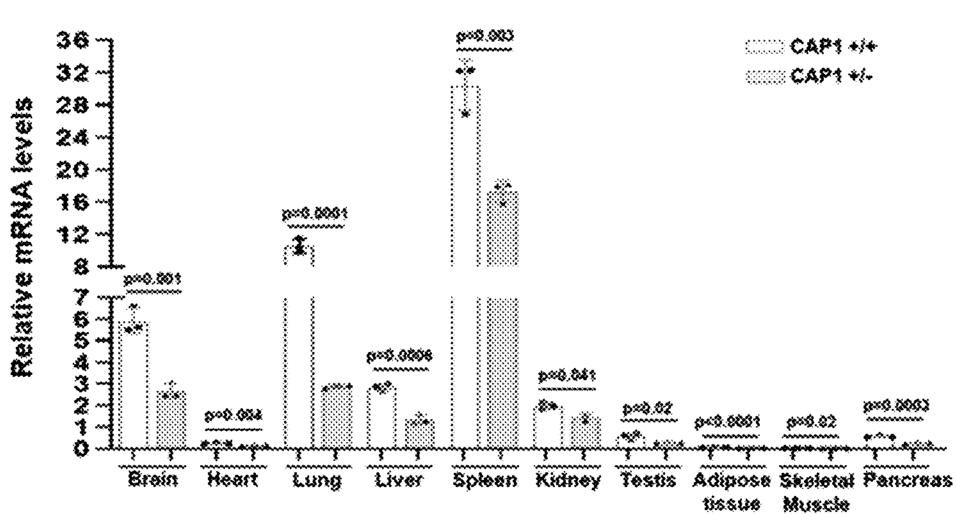
Figure 3D:
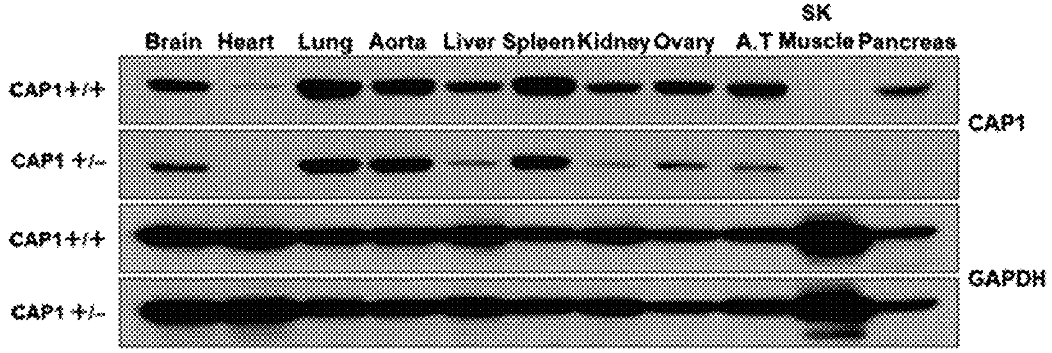
Figure 3E:
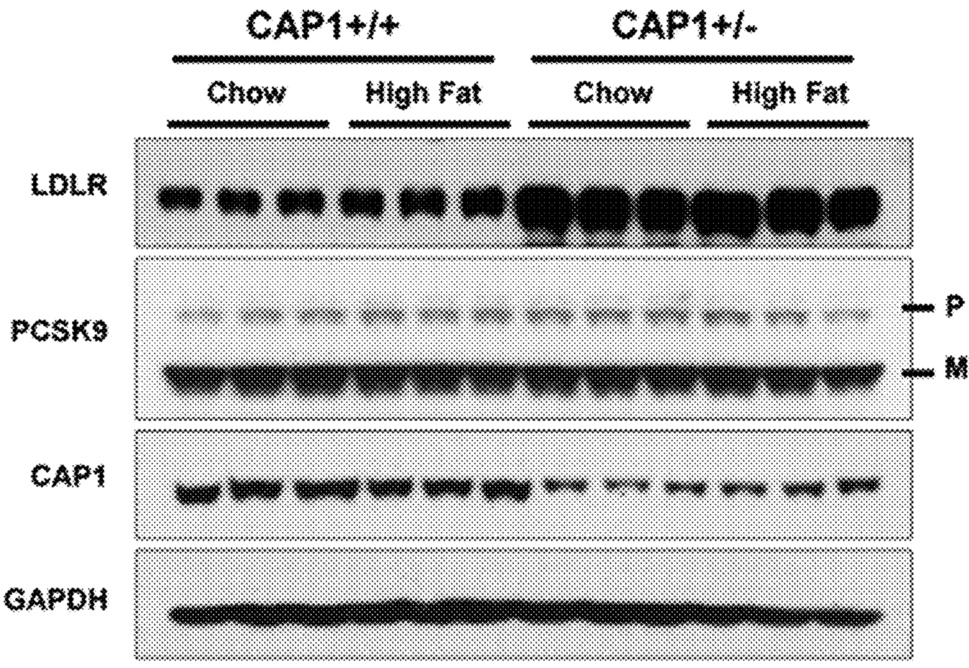
Figure 3E:
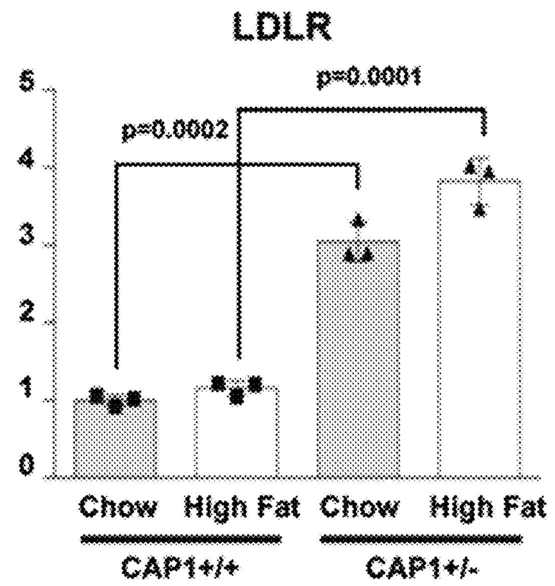
Figure 3F:
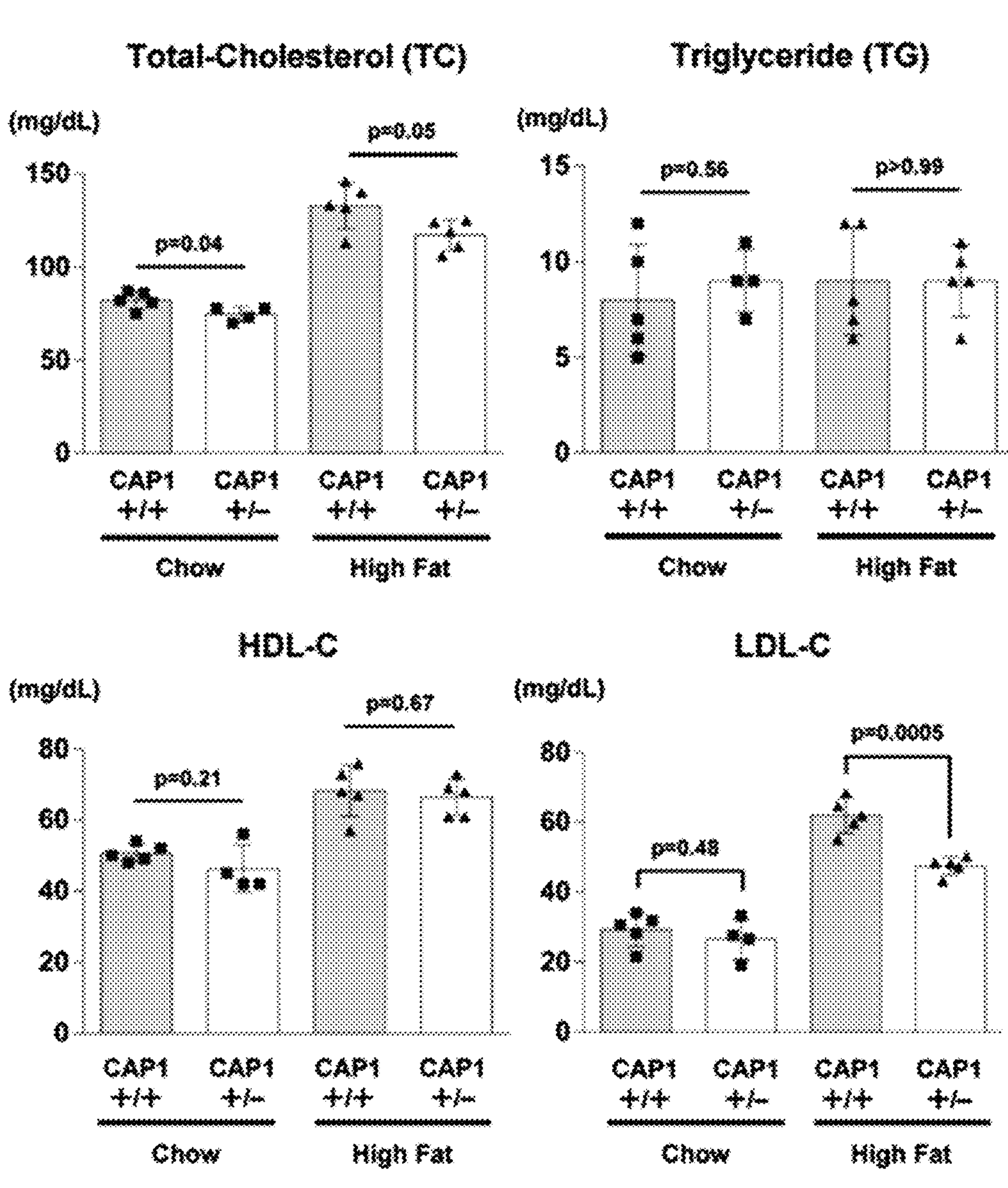

To investigate the role of CAP1 in vivo, CAP1 knock-out mice targeting CAP1 exon 3 were produced using a transcription activator-like effector nuclease (TALEN). Heterozygous knock-out mice (CAP1$^{+/-}$ mice) were used because homozygous knock-out mice died on embryonic day 16.5. It was found that the organs of CAP1$^{+/-}$ mice were not different from those of wild-type mice up to about 16 weeks, and CAP1 mRNA and protein levels were remarkably decreased in various organs of CAP1$^{+/-}$ mice (FIG. 3D). Accordingly, the present inventors compared the expression levels of the LDL receptor and PCSK9 between CAP1$^{+/-}$ mice and CAP1$^{+/+}$ mice fed or not fed a high-fat diet. In the investigation of mRNA expression of the LDL receptor by rt-PCR, no significant difference was confirmed, but the protein level of the LDL receptor was remarkably higher in CAP1$^{+/-}$ mice than in CAP1$^{+/+}$ mice (FIG. 3E). In accordance with the results, it was confirmed that CAP1$^{+/-}$ mice had lower total cholesterol and LDL-cholesterol levels than wild-type mice under a high-fat diet (FIG. 3F). There were no significant differences in plasma triglyceride (TG) and high density lipoprotein (HDL) cholesterol levels.

Figure 3G:
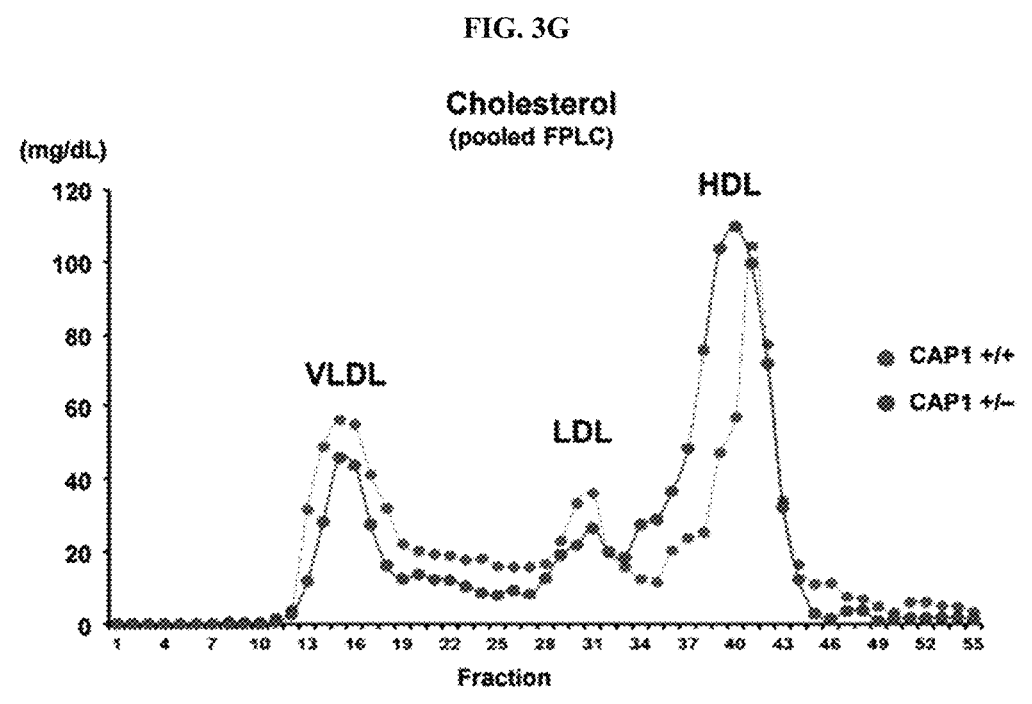

Next, by fractionation of plasma lipoproteins by fast protein liquid chromatography (FPLC), the present inventors confirmed that LDL-cholesterol and VLDL-cholesterol levels were reduced in CAP1$^{+/-}$ mice compared to CAP$^{+/+}$ mice fed a high-fat diet and HDL-cholesterol migrated in a large-buoyant form (FIG. 3G).

Figure 3H:
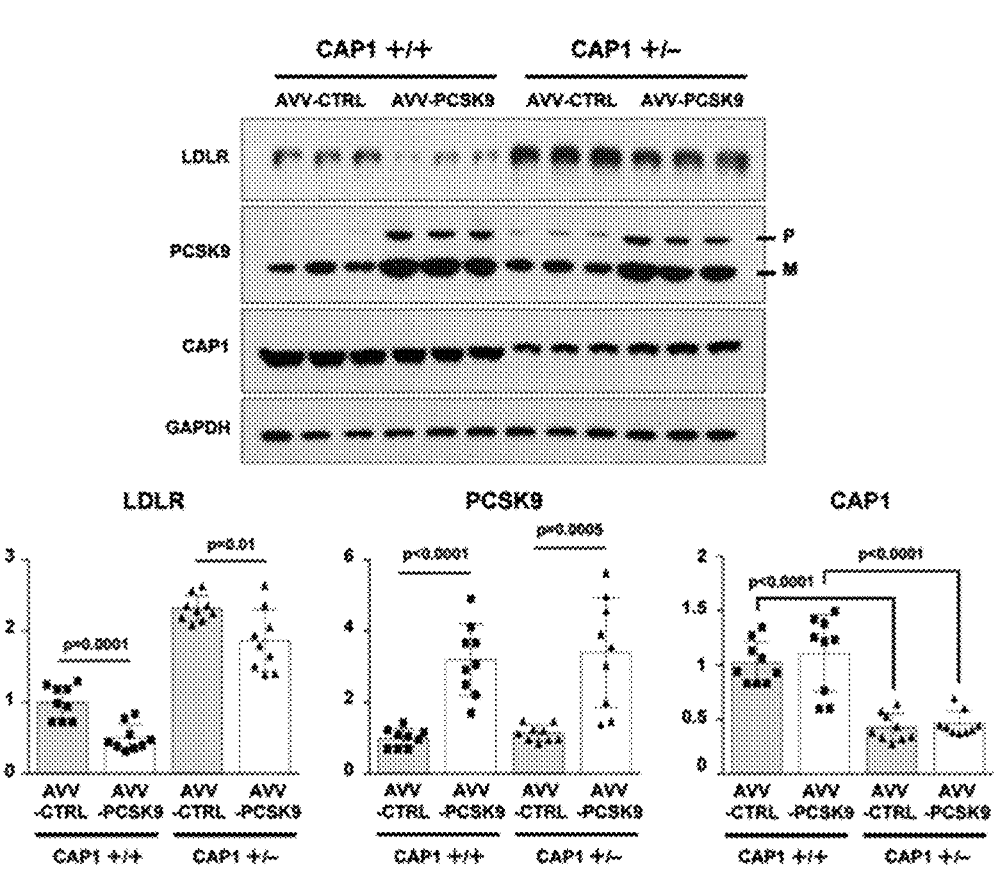
Figure 3I:
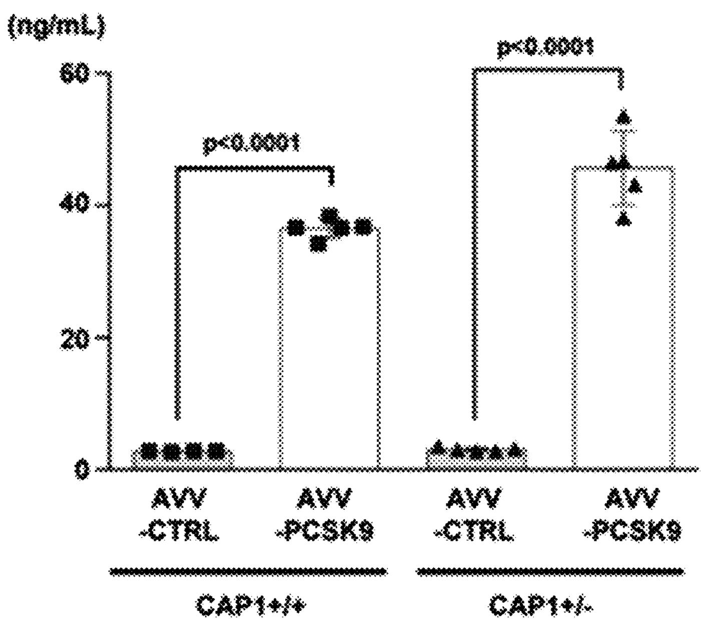
Figure 3J:
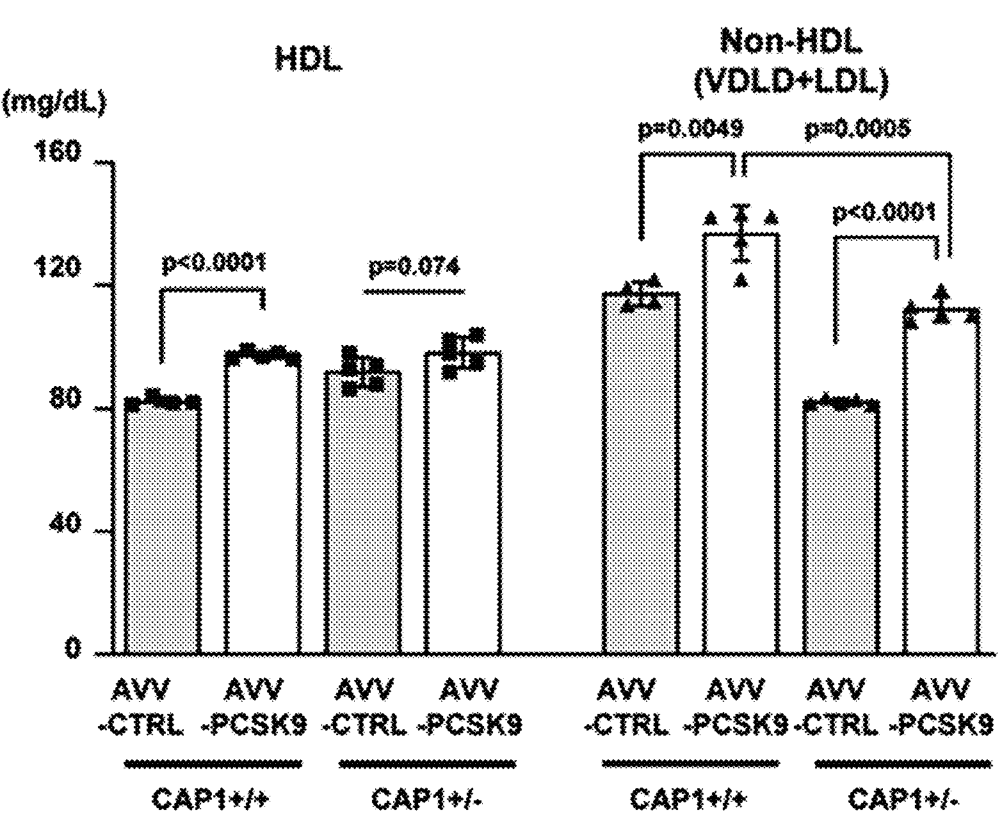

Subsequently, the present inventors overexpressed PCSK9 using an adeno-associated virus in CAP1$^{+/-}$ and CAP1$^{+/+}$ mice, and then measured the expression levels of the LDL receptor and LDL-cholesterol levels. As a result, as illustrated in FIGS. 3H to 3J, CAP1 heterozygous knock-out mice showed an improved cholesterol profile compared to wild-type animals by preventing the reduction or degradation of the LDL receptor protein by transduction of PCSK9. These results show that the CAP1 protein is essential for degradation of the LDL receptor protein by PCSK9.

Figure 4A:
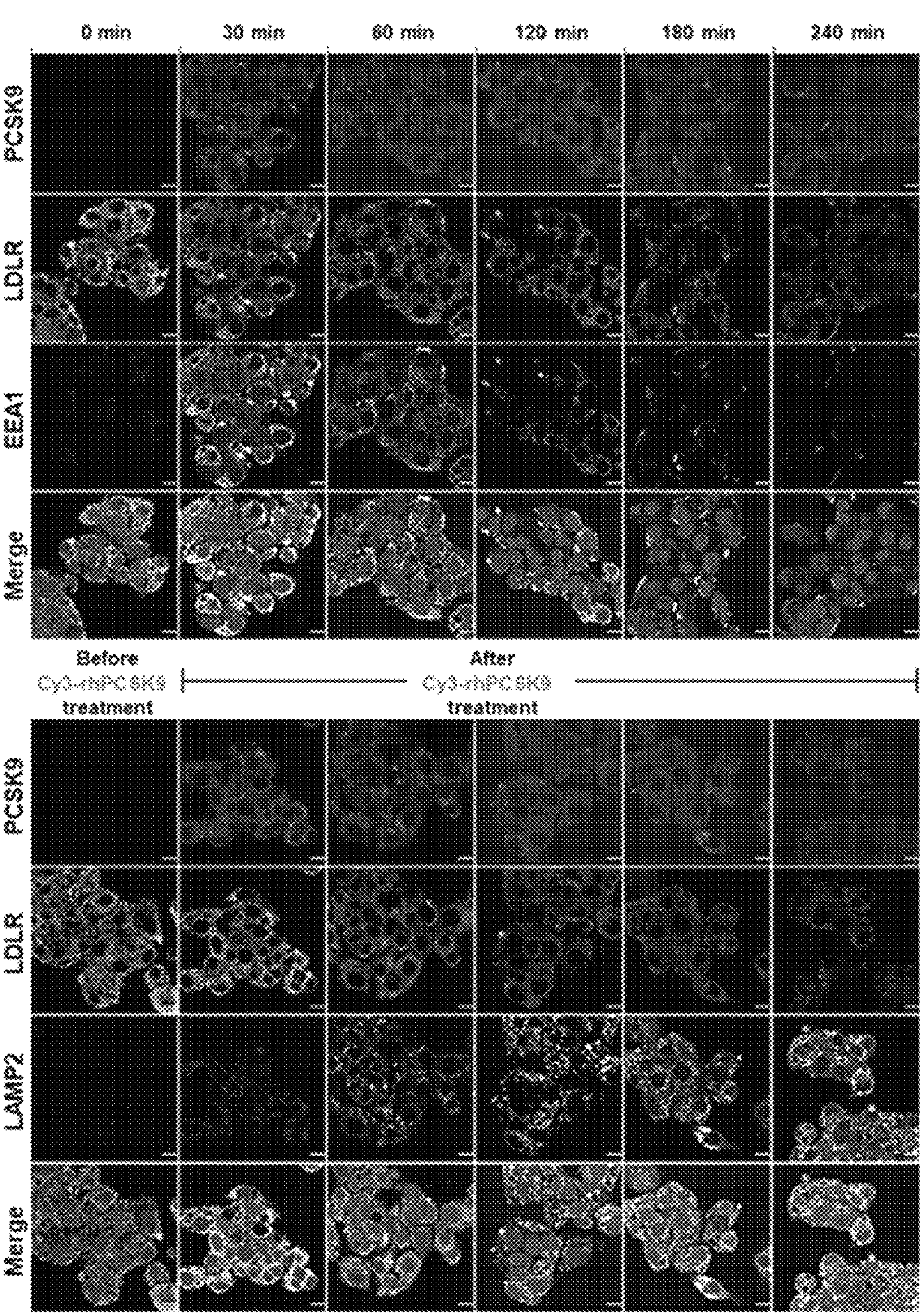
FIGS. 4A to 4S are views showing that CAP1 mediates caveolin-dependent endocytosis and lysosomal degradation of LDL receptors.
Figure 4B:
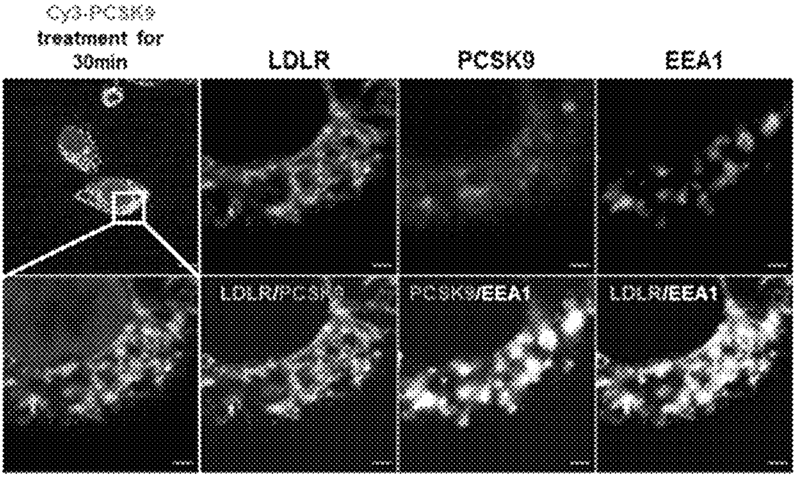
Figure 4C:
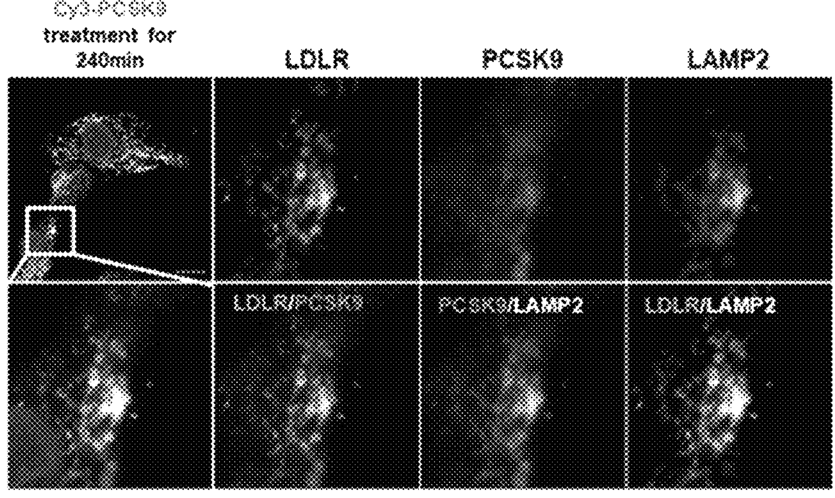
Figure 4D:
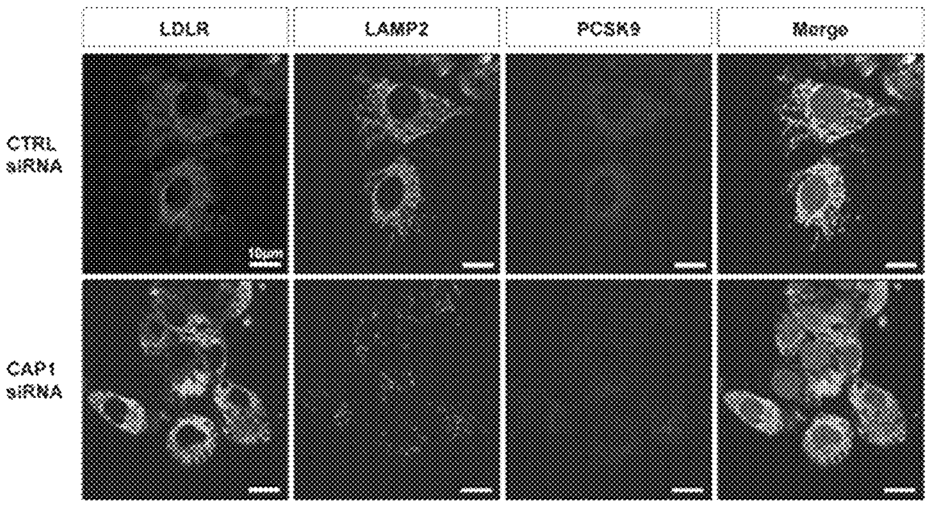
(FIG. 4D) Results of treating HepG2 cells with recombinant hPCSK9 and after 240 minutes, performing immunofluorescent staining with LDL receptor (green), PCSK9 (red) and lysosomal marker LAMP2 (white)

Example 4. CAP1 Induces Caveolae-Dependent Endocytosis of PCSK9-LDL Receptor Complex Leading to LDL Receptor Degradation PCSK9-mediated degradation of the LDL receptor was blocked exclusively by a lysosomal protease inhibitor (E-64d), but not by inhibitors of the proteasome (lactacystin) or autophagy (bafilomycin), suggesting that the LDL receptor is degraded by the lysosomal pathway as previously reported. Such findings were also explained by tracking LDL receptors having PCSK9-Cy3, an endosomal marker early endosome antigen1 (EEA1) and a lysosomal marker lysosome-associated membrane protein2 (LAMP2) in HepG2 cells treated with Cy3 dye-conjugated PCSK9 (PCSK9-Cy3) at various time points. That is, EEA1 was co-localized with PCSK9 and the LDL receptor within 30 minutes after PCSK9-Cy3 treatment (FIG. 4A). Subsequently, LAMP2 co-localized with PCSK9 and the LDL receptor appeared within 60 minutes (FIG. 4B). This increased until 240 minutes when PCSK9 and the LDL receptor disappeared (FIGS. 4A and 4C). Lysosome formation, not such early endosome formation, was blocked by CAP1 depletion (FIG. 4D).

Figure 4E:
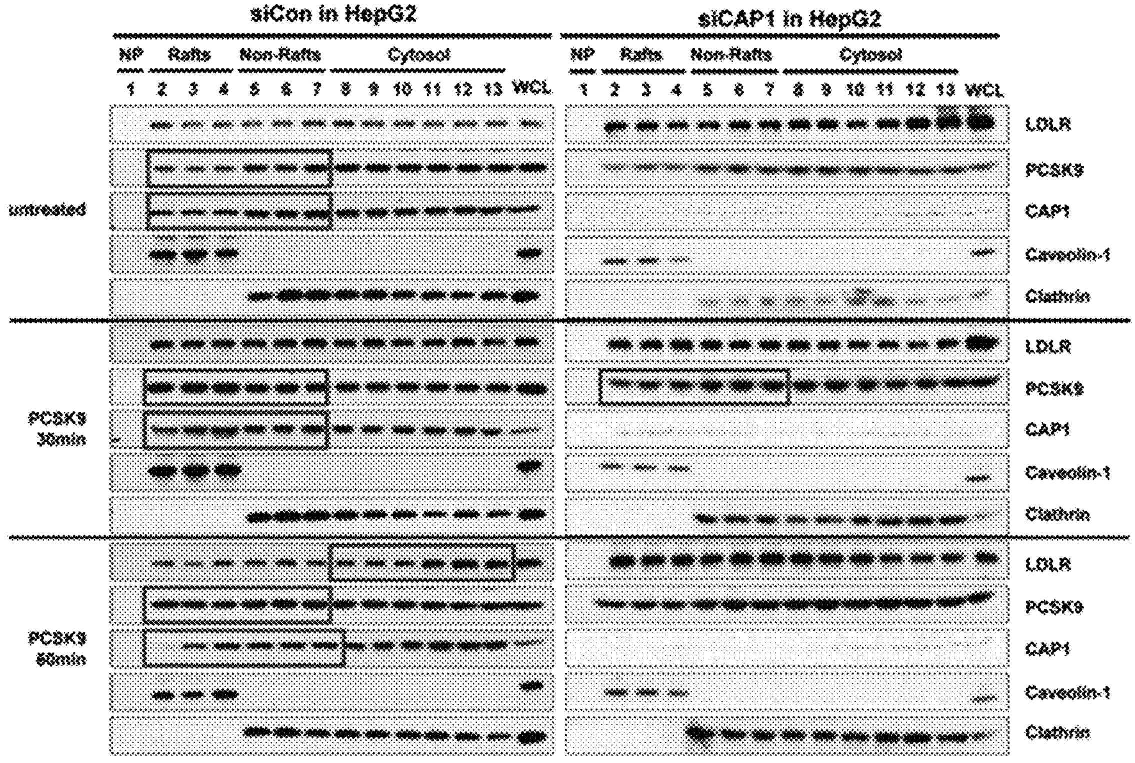
(FIG. 4E) Results of treating HepG2 cells treated with CAP1 siRNA with PCSK9, and then performing cell membrane fractionation showing the cell distribution of LDL receptors, PCSK9 and CAP1 and western blot analysis.
Figure 4F:
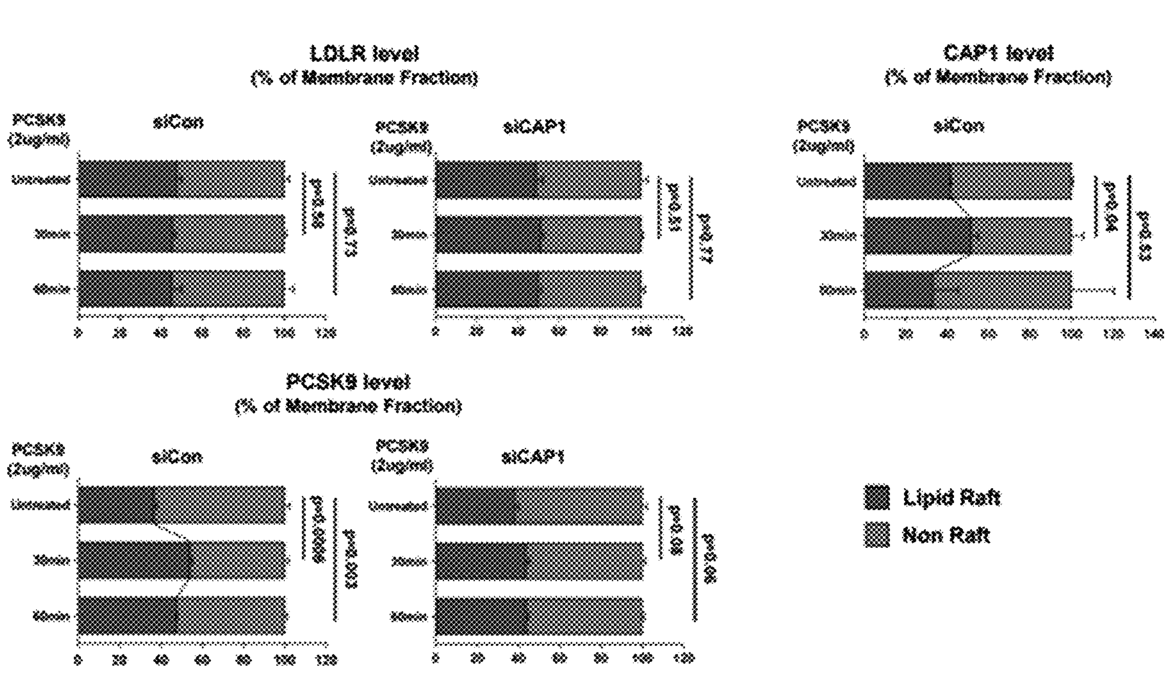
(FIG. 4F) Graph quantifying western blot results of FIG. 4E.

In raft isolation experiments, endogenous PCSK9 was distributed more in a non-raft fraction before exogenous PCSK9 treatment [raft (36.8%)/non-raft (63.2%)]. Within 30 minutes after exogenous PCSK9 treatment, it was predominantly included in a lipid raft fraction [raft (54.3%)/non-raft (45.7%)], which is closely associated with caveolae formation (FIGS. 4E and 4F). The expression of the LDL receptor in the membrane fraction was reduced 60 minutes after PCSK9 treatment. However, the expression pattern of PCSK9 and the LDL receptor was not significantly changed despite the treatment of CAP1-deficient cells with PCSK9 (FIGS. 4E and 4F).

Figure 4G:
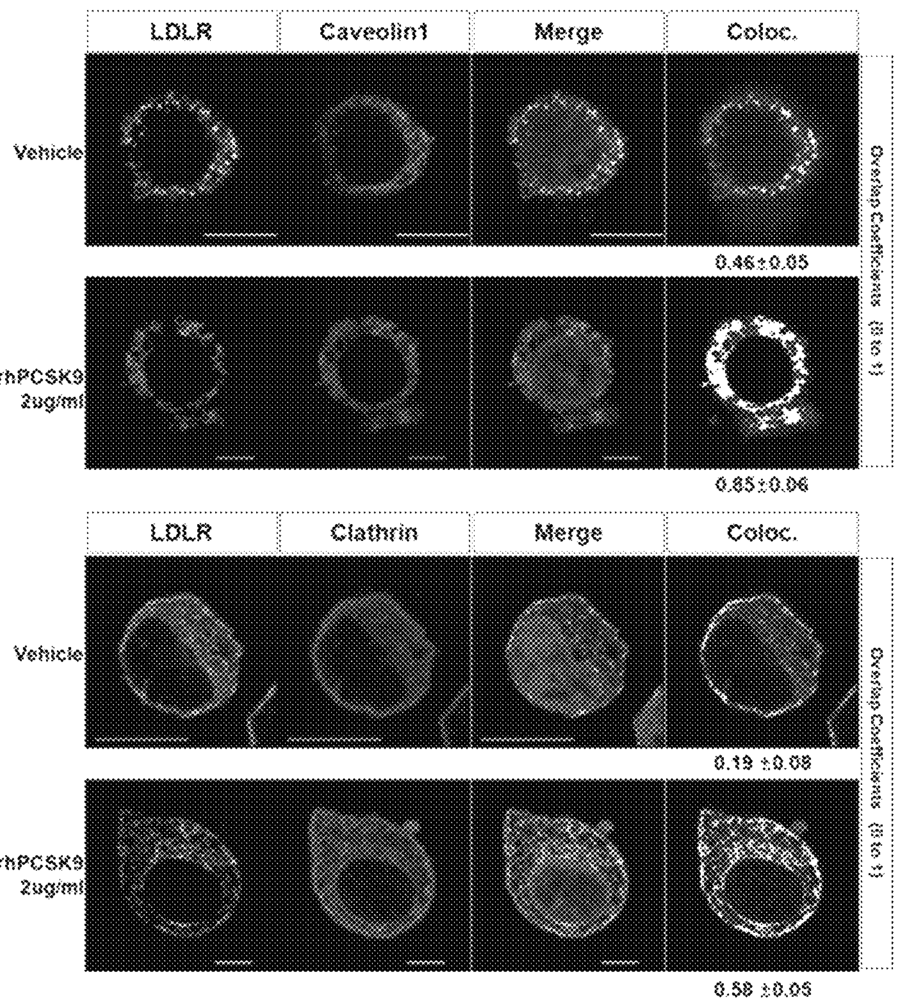
(FIG. 4G) A set of views comparing co-localization between LDL receptor (green) and caveolin 1 (red from top) or clathrin (red from bottom) 30 minutes after treatment with recombinant hPCSK9 in HepG2 cells.
Figure 4H:
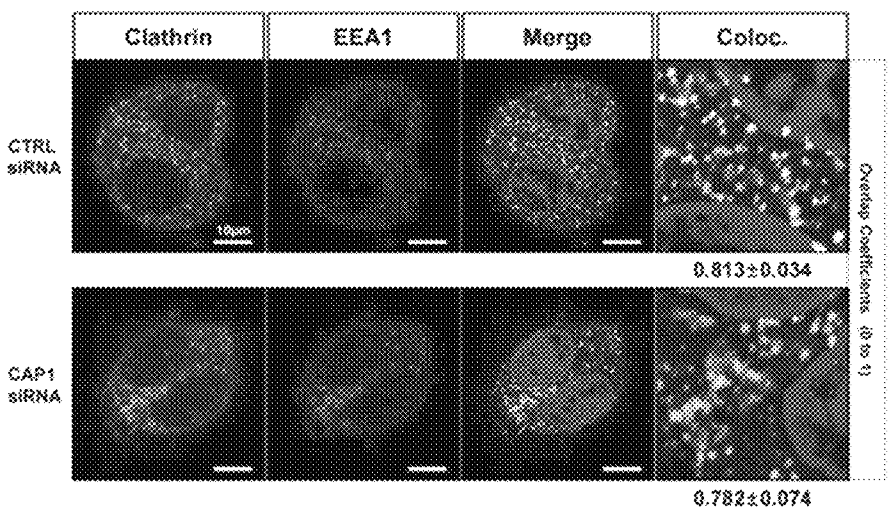
(FIGS. 4H to 4I) Views illustrating co-localization of clathrin or caveolin-1 and endosomal marker EEA1 after treatment with recombinant human PCSK9 in HepG2 cells for 30 minutes.
Figure 4I:
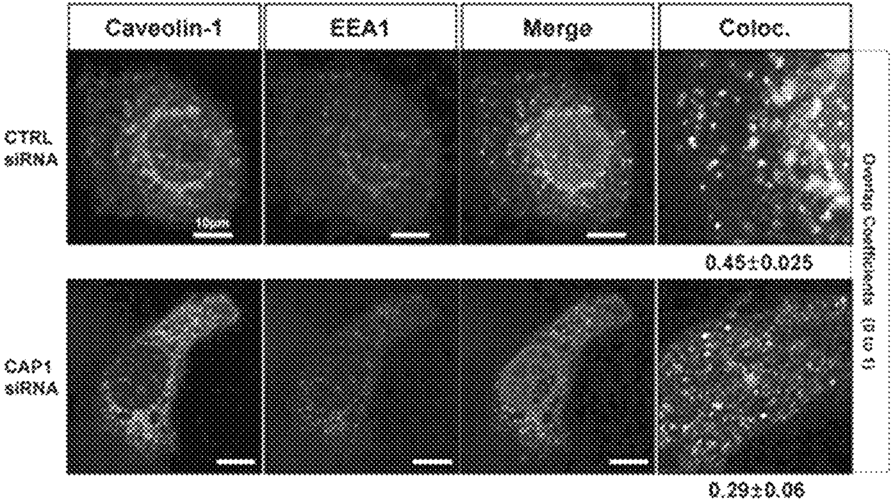

Early endosome formation by PCSK9 is known to be mediated by the clathrin pathway. However, PCSK9 treatment increased not only clathrin, but also the number of co-localized endosomes with caveolin (FIG. 4G). Interestingly, in regard to enhanced endosome formation, knockdown of CAP1 after PCSK9 treatment reduced caveolin-endosomes, but not clathrin-endosomes, and these results suggest that CAP1 induces caveolin-mediated endocytosis, not clathrin-mediated endocytosis of the PCSK9-LDL receptor complex (FIGS. 4H and 4I).

Figure 4J:
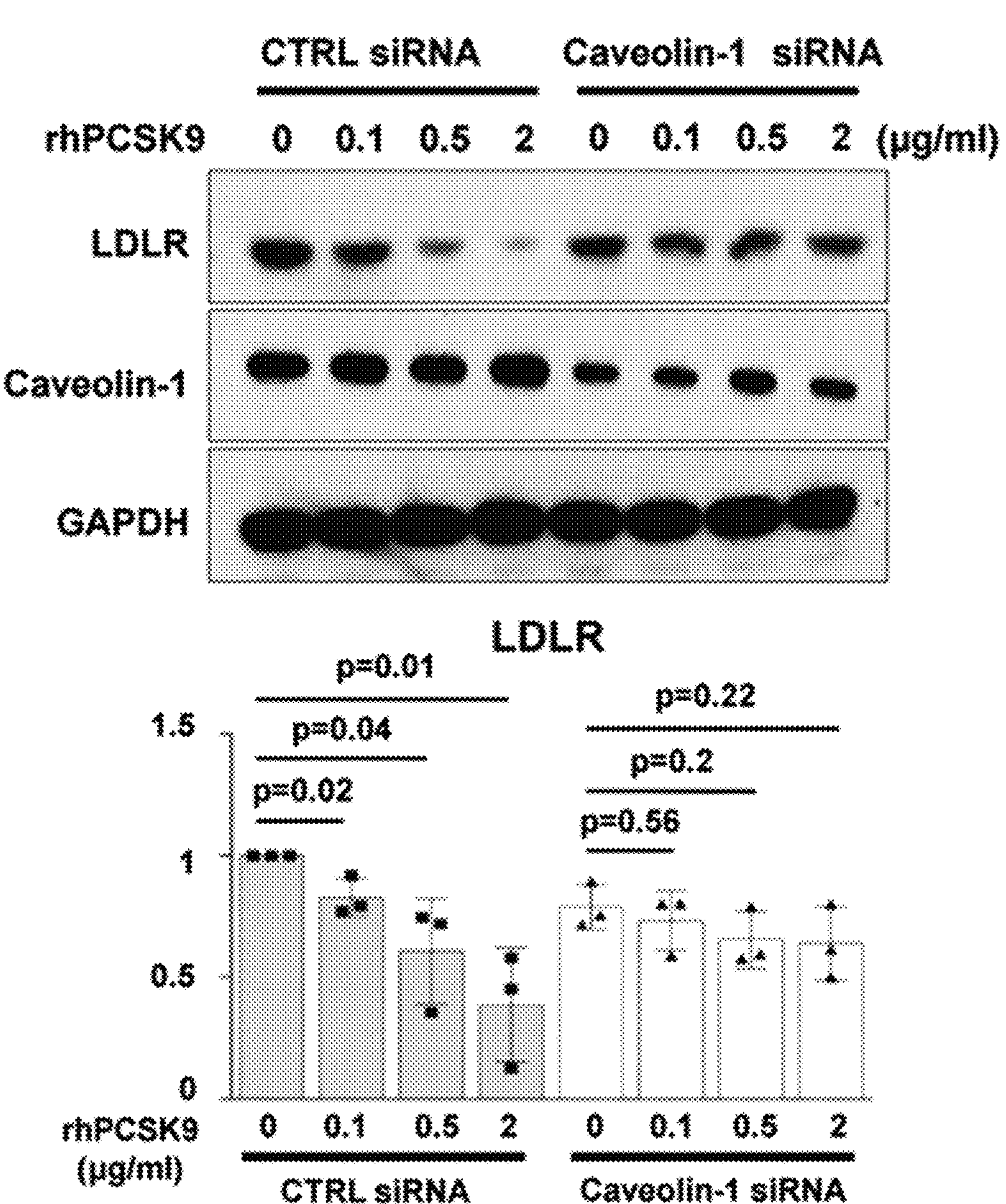
(FIGS. 4J and 4K) Views illustrating effect of caveolin or clathrin knockdown on PCSK9-induced LDL receptor degradation in HEpG2 cells.
Figure 4K:
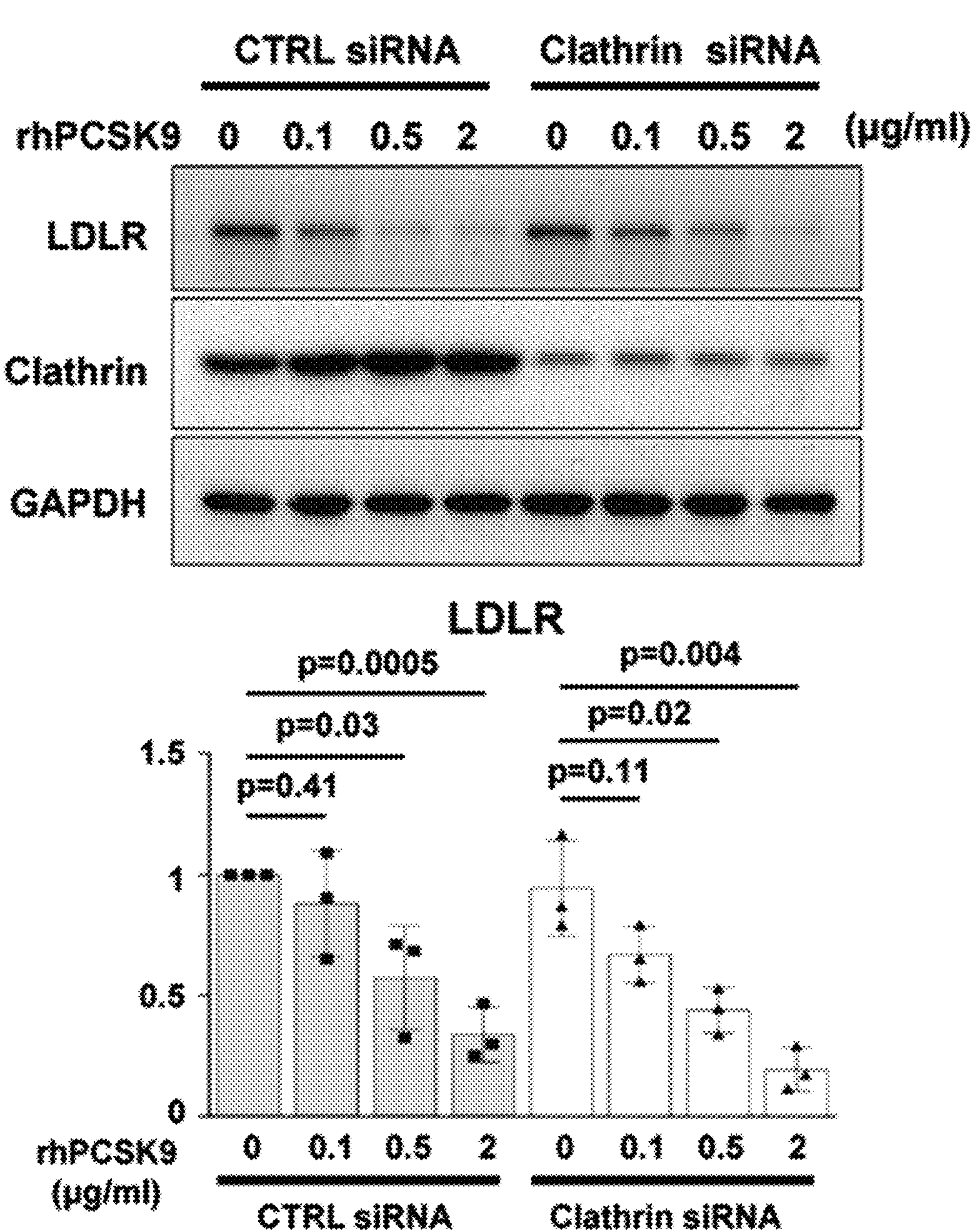

Therefore, caveolin or clathrin was knocked down to compare the caveolin- and clathrin-mediated LDL receptor endocytosis according to PCSK9 treatment, respectively. As a result, as illustrated in FIG. 4J, the LDL receptor was not degraded in caveolin-deficient cells despite PCSK9 treatment. By comparison, as illustrated in 4K, it was confirmed that the LDL receptor was degraded in a dose-dependent manner by PCSK9 treatment in clathrin-deficient cells, and such results suggest that the degradation of the PCSK9-mediated LDL receptor is clathrin-independent.

Figure 4L:
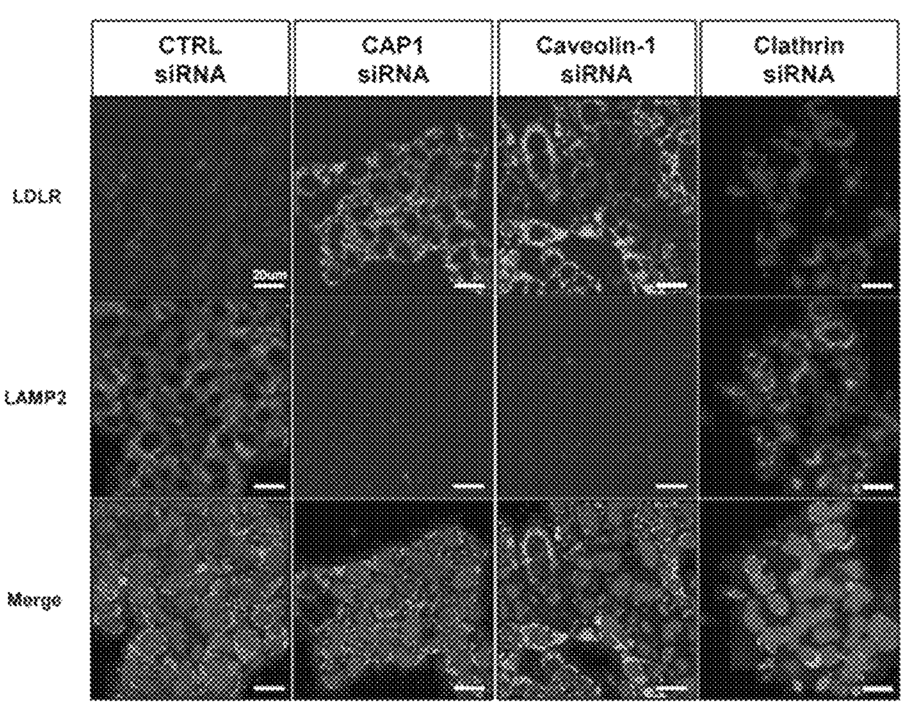
(FIG. 4L) Results of performing immunofluorescent staining with LDL receptor (green) and lysosomal marker LAMP2 (red) 240 minutes after treatment with hPCSK9 in HepG2 cells pre-treated with siRNA for CAP1, caveolin-1 or clathrin.

In the absence of caveolin, LAMP2 could not be formed and the LDL receptor was not degraded by PCSK9. In contrast, in the absence of clathrin, LAMP2 appeared and the LDL receptor was degraded (FIG. 4L). Further, knockdown of CAP1 failed to produce LAMP2, suggesting that CAP1 is closely associated with caveolin-mediated degradation of the LDL receptor by PCSK9 (FIG. 4L).

Figure 4M:
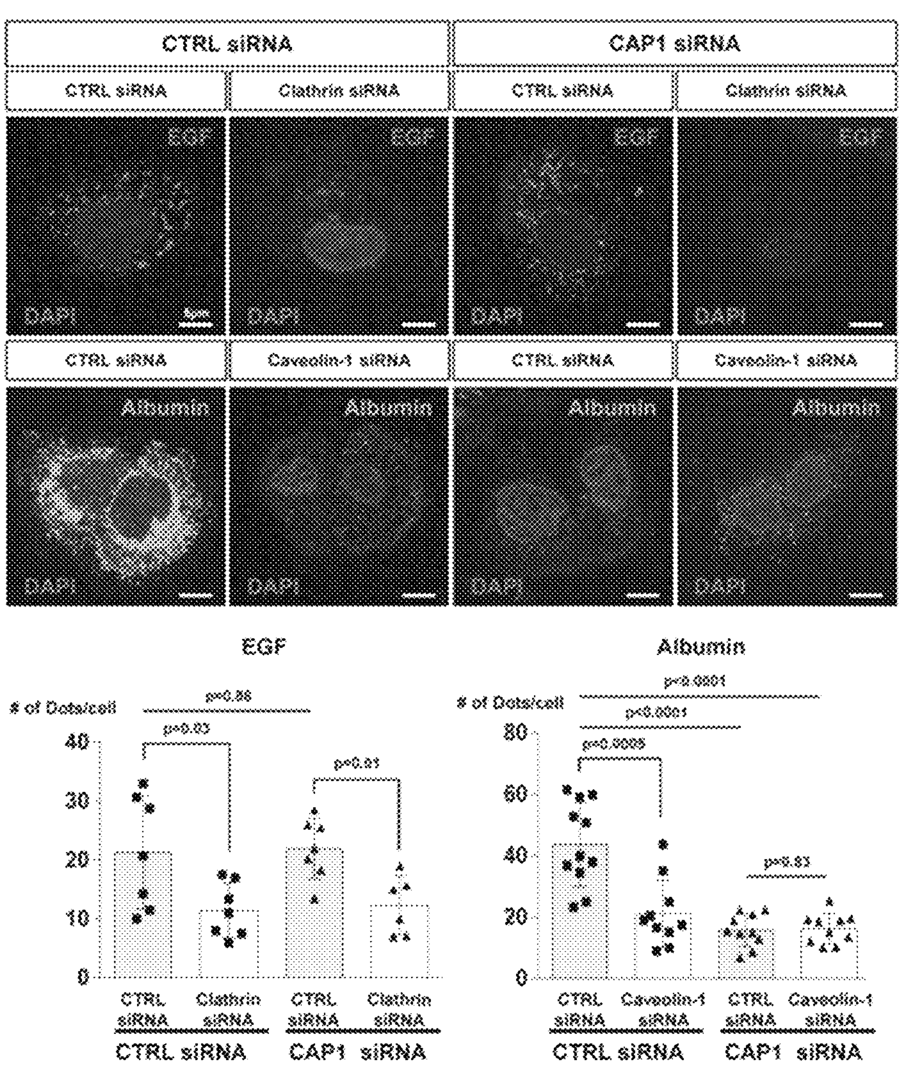
(FIG. 4M) View of immunofluorescent staining of EGF (red) and albumin (green) in HepG2 cells (scale bar, 10 μm)

Next, the present inventors evaluated the effect of CAP1 deficiency on the endocytosis of EGF or albumin. It is known that EGF and the receptor complex thereof are internalized mainly by clathrin-dependent endocytosis, whereas albumin uptake is dependent on caveolae. As a result, as illustrated in FIG. 4M, caveolin-dependent albumin endocytosis was significantly reduced by the deficiency of CAP1, whereas clathrin-dependent EGF receptor endocytosis was not affected.

Figure 4N:
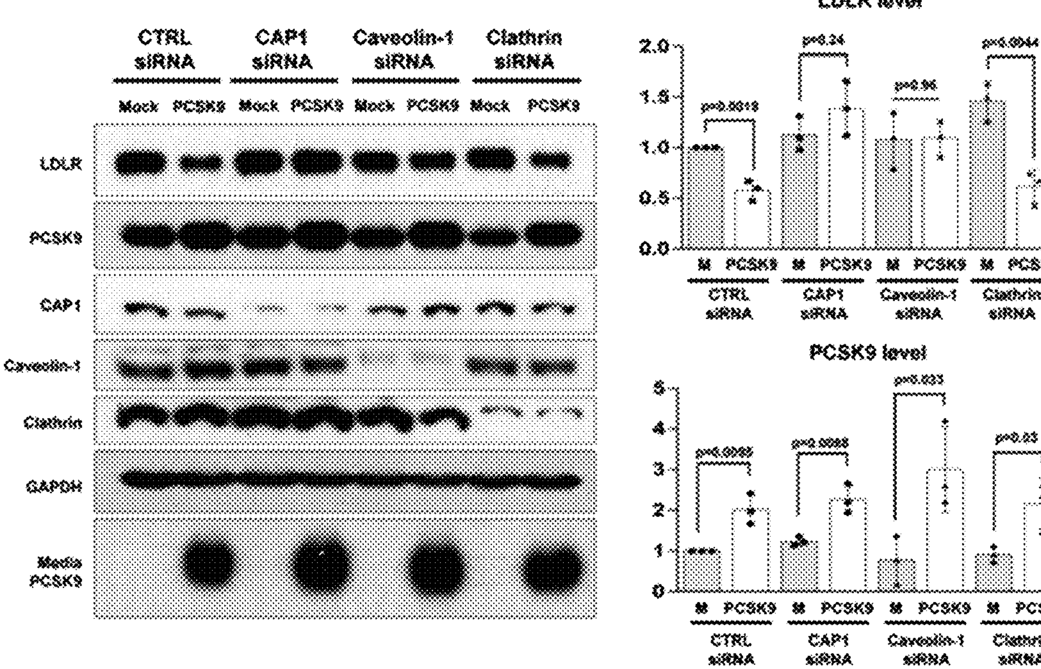
(FIG. 4N) A set of views illustrating the effect of knockdown of CAP1, caveolin-1 or clathrin on LDL receptor degradation induced by PCSK9 overexpression.
Figure 4O:
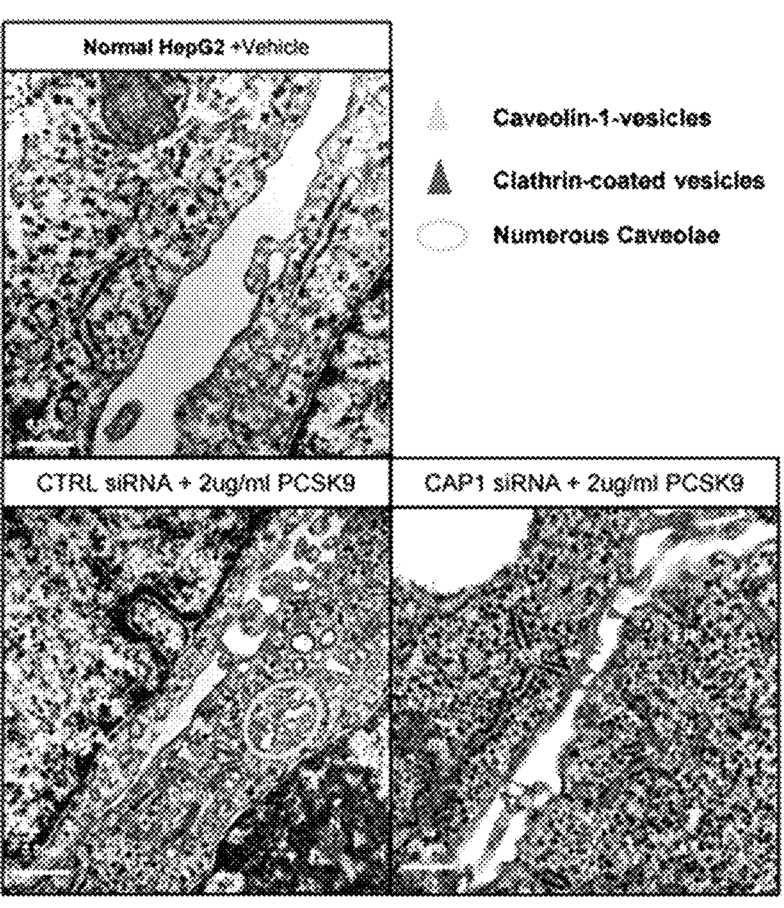
(FIG. 4O) A set of transmission electron microscope images according to CAP1 siRNA treatment 15 minutes after treatment with PCSK9 in HepG2 cells (scale bar, 0.5 μm)
Figure 4P:
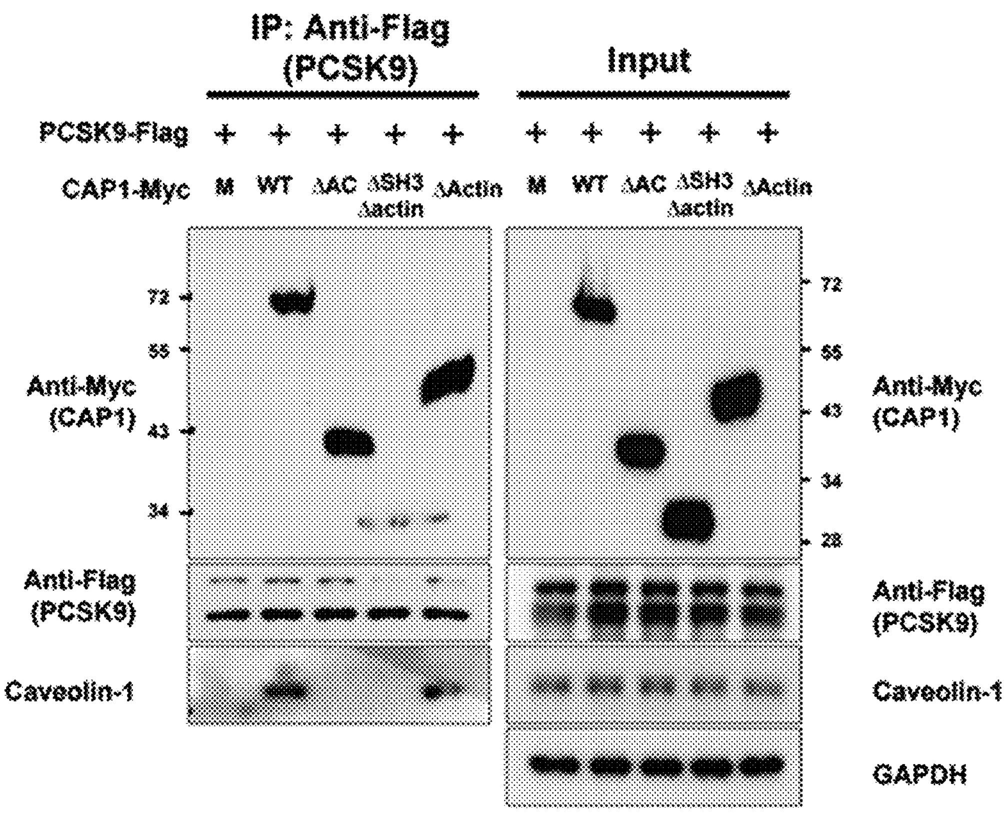
(FIG. 4P) View showing the importance of SH3BD in the binding of CAP1 and caveolin-1.

Such observation suggests that CAP1 may be involved not only in the endocytosis of the PCSK9-LDL receptor complex, but also in general caveolin-dependent endocytosis. In addition, as illustrated in FIG. 4N, the degradation of the LDL receptor mediated by endogenously overexpressed PCSK9 was attenuated by siRNA for CAP1 or caveolin. Furthermore, electron microscopy analysis showed that only caveosome formation, not clathrin, was remarkably attenuated by CAP1 siRNA after PCSK9 treatment (FIG. 4O). The mechanism by which CAP1 directs the PCSK9-LDL receptor complex to caveosomes is based on the binding of the AC domain of CAP1 to caveolin-1. In immunoprecipitation experiments, PCSK9 including the LDL receptor was able to form complexes with wtCAP1 and caveolin-1, but not in the presence of mutant CAP1, such as ΔSH3BD ΔactinBD or ΔACBD CAP1 (FIG. 4P). These results demonstrate that the SH3BD of CAP1 is essential for binding to the CRD of PCSK9.

Figure 4Q:
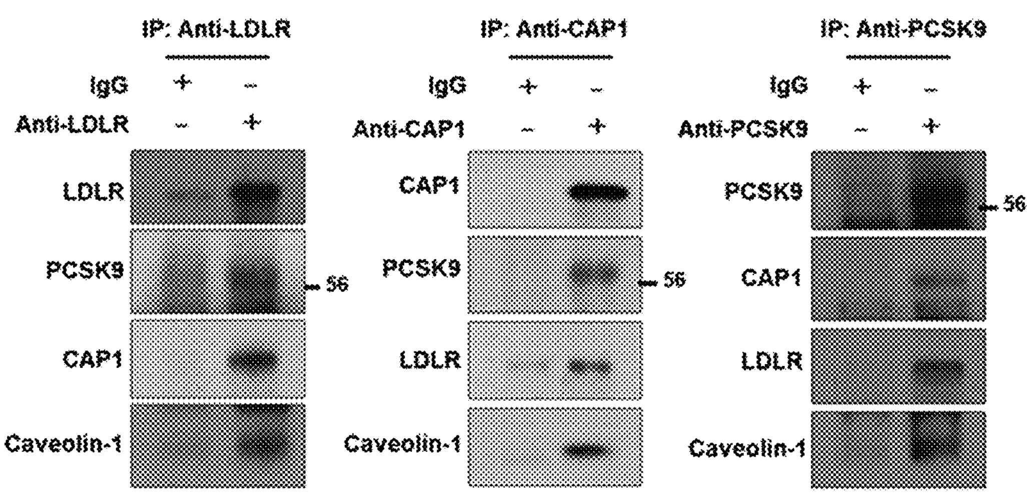
(FIG. 4Q) Results of immunoprecipitation assay for caveolin-1, LDL receptor, CAP1 and PCSK9 in liver lysates of wild-type mice.
Figure 4Q:
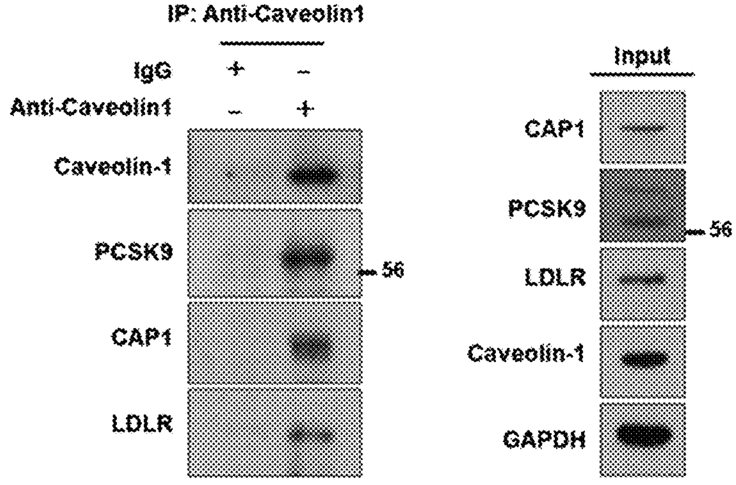
Figure 4R:
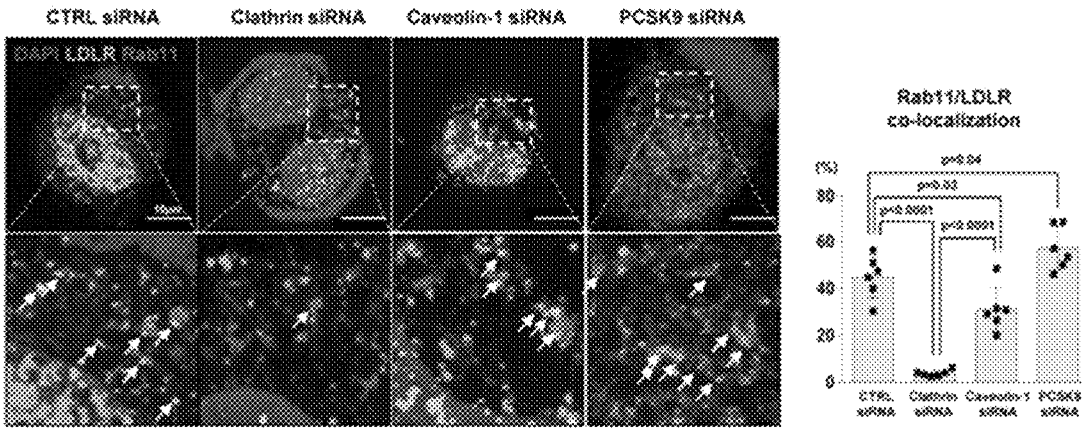
(FIG. 4R) Results of performing immunofluorescent staining with Rab11 (red), LDL receptor (green) and DAPI (blue) 4 hours after treatment of LDL cholesterol in HepG2 cells.

Furthermore, the ActinBD of CAP1 is also required for binding to caveolin. As illustrated in FIG. 4Q, immunoprecipitation analysis on wild-type mouse liver lysates showed that caveolin binds to the LDL receptor, CAP1 and PCSK9. Additionally, the LDL receptor-PCSK9-CAP1 complex was co-localized with caveolin in the mouse liver. One hour after LDL-cholesterol treatment, the endocytosis of the LDL receptor, which was stained with an early endosomal marker Rab5, was significantly reduced by both clathrin siRNA and caveolin siRNA. When PCSK9 was blocked in the siRNA-attenuated LDL receptor degradation pathway, caveolin-mediated LDL receptor endocytosis was significantly reduced, whereas clathrin-mediated endocytosis was not significantly altered. In addition, co-staining of Rab11 and the LDL receptor associated with the recycling mechanism 4 hours after LDL-cholesterol treatment showed that the amount of recycled LDL receptor was remarkably reduced in clathrin siRNA treatment compared to caveolin siRNA treatment (FIG. 4R).

Figure 4S:
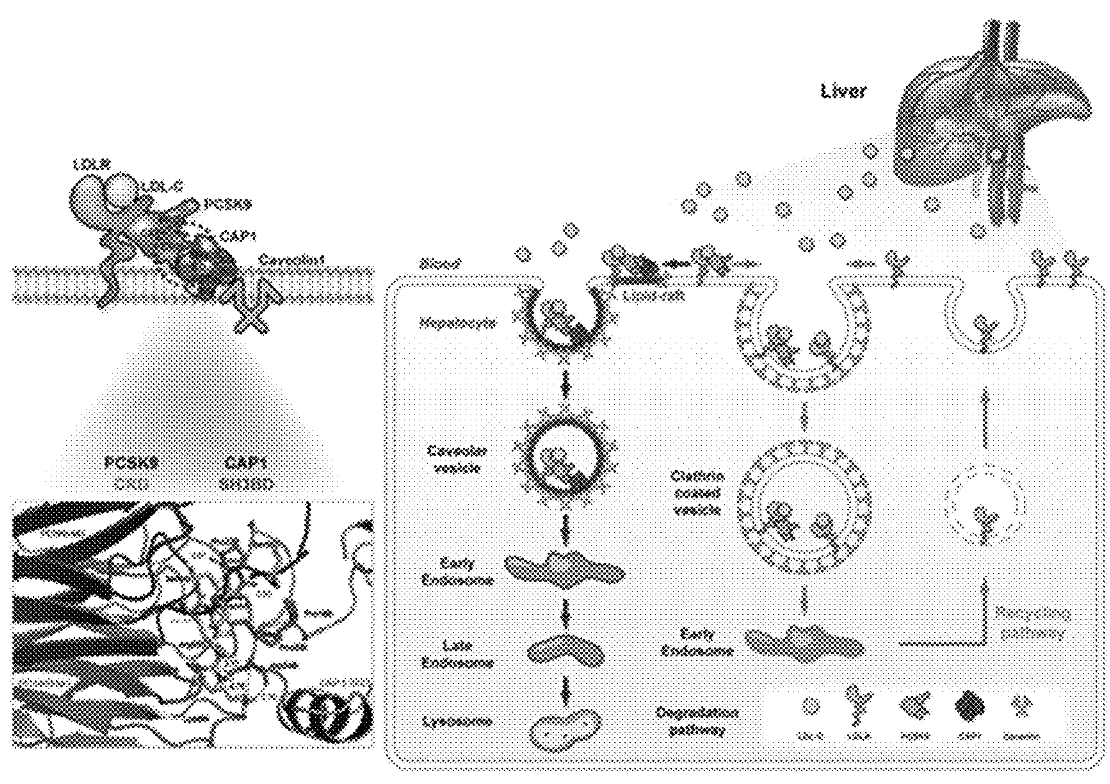

When the results demonstrated through Examples 1 to 4 are combined, as illustrated in the schematic view of FIG. 4S, the LDL receptor enters the cell by clathrin-dependent endocytosis as the LDL receptor binds to LDL-cholesterol, and then allosteric dissociation is caused by the acidic pH of the endosomes and thus the LDL receptor is regenerated on the cell surface. PCSK9 also promotes clathrin-dependent endocytosis but does not cause lysosomal degradation of the LDL receptor. However, when the LDL receptor-PCSK9 complex interacts with CAP1, CAP1 may bind to caveolin-1 through its actin-binding domain, so these proteins enter cells by caveolin-dependent endocytosis. Subsequently, caveolin-coated endosomes including the LDL receptor-PCSK9-CAP1 complex are directed to lysosomes for degradation. That is, it is revealed for the first time that as a binding partner of PCSK9, CAP1 is an essential molecule that mediates the endocytosis and lysosomal degradation of the caveolin-dependent LDL receptor.

Example 5. Preparation of Competitive Inhibitor Fc-CAP1 of CAP1

A protein synthesis company was commissioned to construct hFc-CAP1 according to the present invention according to the amino acid sequence of SEQ ID NO: 4. A pCEP4 expression vector was used for the expression of mFc-CAP1.

Expi293 cells used for protein purification were cultured according to the manufacturer's (Thermo Scientific, USA) culture method with some modifications. More specifically, 0.5× antibiotic-antimycotic (Gibco, 15240-062, USA) was added to FreeStyle medium to culture the cells in a shaker maintained at a temperature of 37° C., a $CO_2$ partial pressure of 7% and 140 RPM. During the transduction of an mFc-CAP1 plasmid, 300 ml of the cells were cultured at $1\times10^6$ cells per ml. The next day, a transfection mixture [30 ml of 150 mM NaCl+600 μg (2 μg/ml) mFc-CAP1 plasmid+1200 μg PEI] was prepared, incubated at room temperature for 30 minutes, and then added in a dropwise manner to the cells.

On day 7 after the day of transfection, the cells and the medium were centrifuged at 3,000 rpm for 10 minutes, and then the supernatant was collected. The collected supernatant was concentrated, then filtered using a column and mFc beads (CaptureSelect™ IgG-Fc, ms), and separated from the beads sequentially using 0.1 M glycine (pH 2.8). Thereafter, the degree of protein expression was confirmed by western blot, and the buffer was dialyzed against PBS using a column (Zeba™ Spin Desalting Columns).

The mFc-CAP1 isolated and purified as described above was used as an inhibitor of binding (or suppressor) between CAP1 and resistin or CAP1 and PCSK9 in the following Examples 6 to 8.

Example 6. mFc-CAP1 Suppresses Activation of NF-κB p65 Subunit in Peripheral Blood Mononuclear Cells Human mononuclear cell line THP-1 cells were cultured in an RPMI medium including 1× antibiotic-antimycotic (Gibco, 15240-062, USA) and 10% fetal bovine serum (FBS) in an incubator maintained at a temperature of 37° C. and a $CO_2$ partial pressure of 5% according to the culture method of American Type Culture Collection (ATCC, USA). Thereafter, the THP-1 cells were diluted with the RPMI medium, and then $1\times10^6$ cells per well were uniformly added thereto, and cultured in an incubator under conditions of 37° C. and 5% $CO_2$ for 24 hours.

To maximize the effect on THP-1 cells, the cells were cultured in 0.1% FBS RPMI under conditions of 37° C. and 5% $CO_2$ for 16 hours to induce the starvation state of cells. Thereafter, 1 μg/ml recombinant human (rh) PCSK9 or 50 ng/ml recombinant human resistin (rhResistin) was mixed with mFc-CAP1 at each concentration (0.1, 0.5, and 2 μg/ml) and pre-cultured for 30 minutes, and then THP-1 cells were treated with the pre-cultured mixture for 30 minutes. Thereafter, proteins were isolated from THP-1 cells using a cell lysis buffer (CST, #9803) and confirmed by western blot.

Figure 5A:
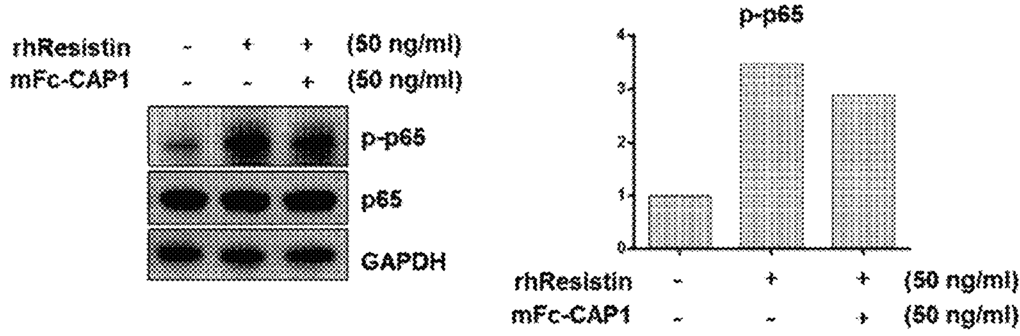
FIGS. 5A and 5B are views showing that mFC-CAP1 can suppress the activation of the NF-κp65 subunit in peripheral blood mononuclear cells.
Figure 5B:
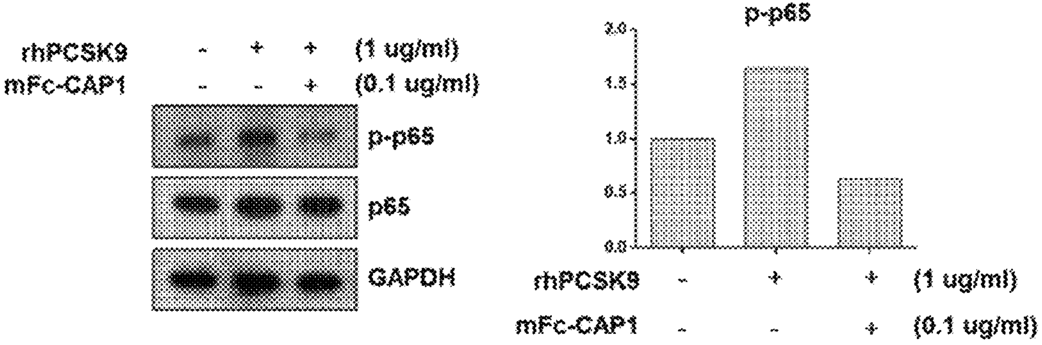

As a result, as illustrated in FIG. 5A, the 5276 position of the p65 subunit was phosphorylated by resistin treatment in THP-1 to induce the activation of NF-κ, and in a group also treated with mFc-CAP1, it was confirmed that phosphorylation of p65 was suppressed in a concentration-dependent manner. In the case of PCSK9, as illustrated in FIG. 5B, the S276 position of the p65 subunit was phosphorylated by PCSK9 treatment in THP-1, and it was confirmed that the phosphorylation of p65 was suppressed in a concentration-dependent manner when treated with mFc-CAP1. The results described above mean that the induction of inflammation according to NF-κB activation by PCSK9 is effectively inhibited by mFc-CAP1.

Example 7. mFc-CAP1 in Hepatocytes Suppresses Degradation of LDL Receptor and Activation of NF-κB and Promotes Activation of AMPK Pathway 7.1. Culture of HepG2 Human Liver Cancer Cells HepG2 cells were cultured in a Dulbecco's Modified Eagle's medium (DMEM, high glucose) including 1× antibiotic-antimycotic (Gibco) and 10% FBS in an incubator maintained at a temperature of 37° C. and a $CO_2$ partial pressure of 5% according to the culture method of ATCC. Thereafter, the HepG2 cells were diluted with the DMEM medium, and then $1\times10^5$ cells per well were uniformly added thereto, and cultured in an incubator under conditions of 37° C. and 5% $CO_2$ for 24 hours.

7.2. Confirmation of PCSK9-Mediated LDL Receptor Protective Effect and AMPK Pathway Activation Effect of mFc-CAP1

HepG2 cells were cultured in a basal DMEM in an incubator at 37° C. and 5% $CO_2$ for 6 hours. Thereafter, the cells were simultaneously treated with 2 μg/ml recombinant human PCSK9 and each concentration (0.1, 1 μg/ml or 0.05, 0.15, 0.5 μg/ml) of mFc-CAP1 for 4 hours. Thereafter, proteins were isolated from HepG2 cells using a cell lysis buffer (CST, #9803), and after electrophoresis, the proteins were transferred to a polyvinylidene fluoride membrane (PVDF) membrane (Millipore, USA), and then reacted with each antibody.

Figure 6A:
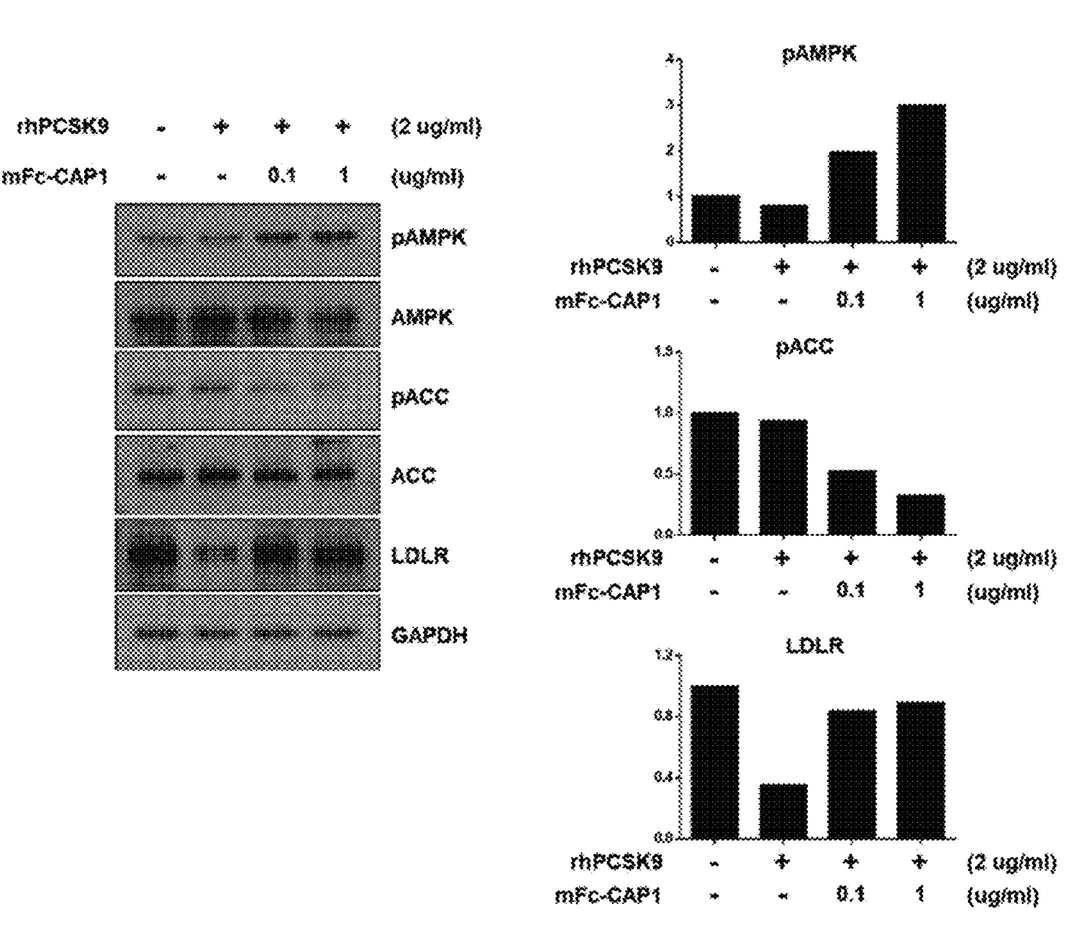
FIGS. 6A to 6F are views showing that mFc-CAP1 has LDL receptor protective effect, AMPK pathway activation and NF-κ inhibitory effect in hepatocytes.
Figure 6B:
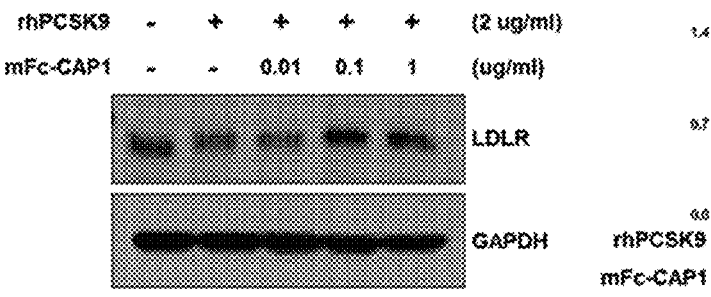
Figure 6B:
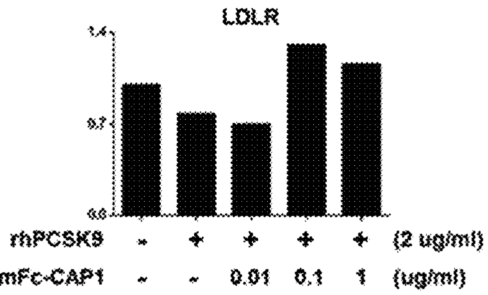

As a result, as illustrated in FIGS. 6A and 6B, it was confirmed that when HepG2 cells were treated with PCSK9 alone, the degradation of the LDL receptor was promoted by PCSK9, and when the HepG2 cells were treated with mFc-CAP1 simultaneously, the protective effect on the LDL receptor appeared in a concentration-dependent manner. In addition, it was confirmed that AMPK was effectively phosphorylated during mFc-CAP1 treatment, and accordingly, the phosphorylation of ACC was suppressed.

The results described above directly show that mFc-CAP1 according to the present invention can successfully suppress LDL receptor degradation through AMPK activation, and accordingly, there is an effect of protecting the LDL receptor for reducing blood LDL-cholesterol levels.

7.3. Confirmation of Resistin-Mediated LDL Receptor Protective Effect and NF-κ Inhibitory Effect of mFc-CAP1

HepG2 cells were treated with 50 ng/ml rh resistin and each concentration (0.1, 1 μg/ml or 0.05, 0.15, 0.5 μg/ml) of mFc-CAP1 and cultured in an incubator at 37° C. and 5% $CO_2$ for 12 to 16 hours. Thereafter, proteins were obtained by the method described in Example 7.2, electrophoresed, and then respectively reacted with specific antibodies.

Figure 6C:
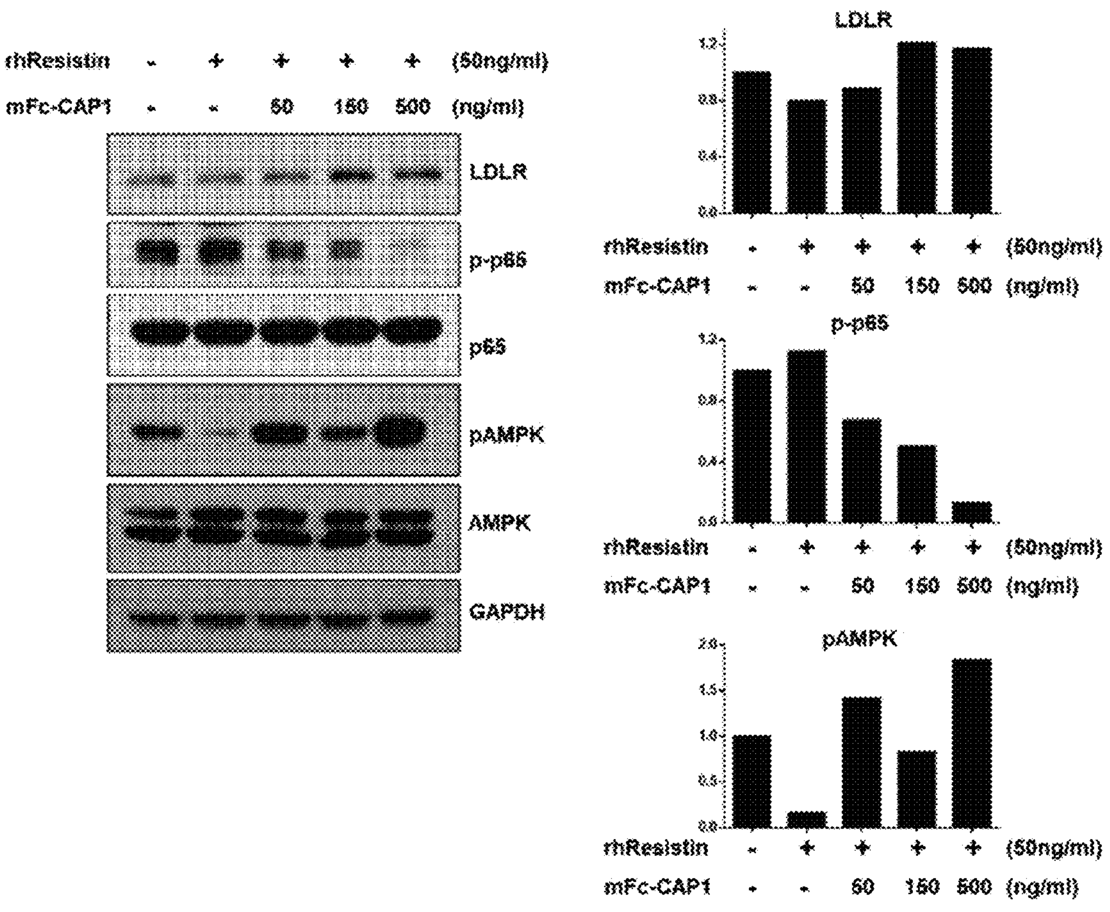
Figure 6D:
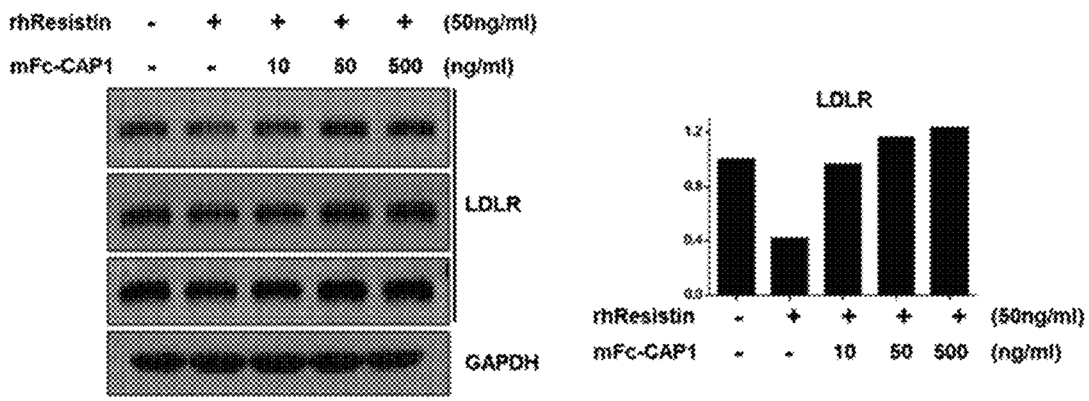

As a result, as illustrated in FIGS. 6C and 6D, when cells were co-treated with mFc-CAP1 and rh-resistin overnight, the degradation level of the LDL receptor by rh resistin was found to be relatively moderate. In addition, it was confirmed that p-p65 activated by resistin was reduced by mFc-CAP1 treatment, whereas pAMPK was activated by mFc-CAP1 treatment.

The results described above confirm that mFc-CAP1 according to the present invention can suppress LDL receptor degradation by resistin, and this is due to suppression of p65 phosphorylation and activation of AMPK, demonstrating that a competitive inhibitor of CAP1 has a protective effect on LDL receptors for reducing blood LDL-cholesterol levels.

7.4. Confirmation of Resistin-Mediated LDL Receptor Protective Effect and AMPK Pathway Activation Effect of mFc-CAP1

After HepG2 cells in culture were changed to a basal DMEM medium, the HepG2 cells were cultured in an incubator at 37° C. and 5% $CO_2$ for 6 hours. After 6 hours, the HepG2 cells were pre-treated with 5-aminoimidazole-4-carboxamide riboside (AICAR), an AMPK activator, for 1 hour, and then treated with 50 ng/ml rh resistin and each concentration (0.05, 0.5 μg/ml) of mFc-CAP1 in combination for 4 hours.

Figure 6E:
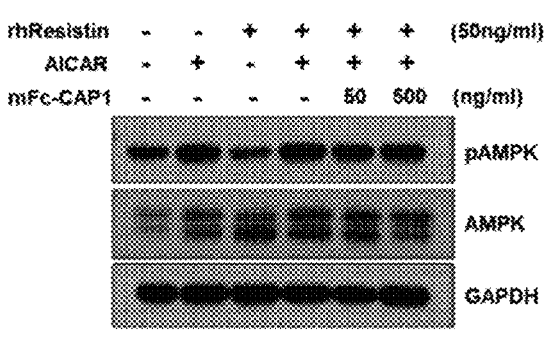
Figure 6E:
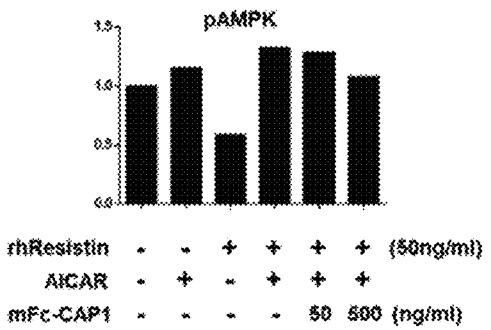

As a result, as illustrated in FIG. 6E, it was confirmed that the activation of AMPK by AICAR was suppressed by resistin, which was again activated by mFc-CAP1 treatment.

Figure 6F:
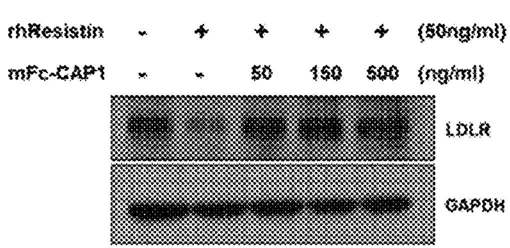
Figure 6F:
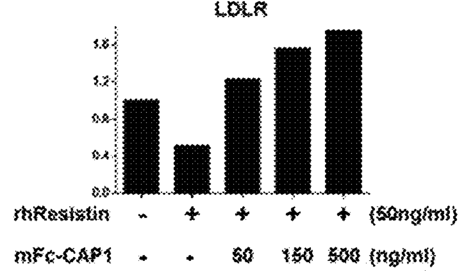

Furthermore, when HepG2 cells in culture was changed to a basal DMEM medium, cultured in an incubator at 37° C. and 5% $CO_2$ for 6 hours, and simultaneously treated with 50 ng/ml rh resistin and each concentration (0.1, 1 μg/ml or 0.05, 0.15, 0.5 μg/ml) of mFc-CAP1, as illustrated in FIG. 6F, it was confirmed that the degradation of the LDL receptor was promoted by treatment with rh resistin alone, and that degradation was suppressed by simultaneous treatment with mFc-CAP1.

Example 8. Knock-Down of CAP1 in Human Umbilical Vein Endothelial Cells (HUVECs) Suppresses Uptake of LDL-Cholesterol In order to directly confirm the LDL cholesterol uptake inhibitory effect of mFc-CAP1 according to the present invention, the present inventors suppressed CAP1 gene expression in human umbilical vein endothelial cells using shRNA. The shCAP1 of the following SEQ ID NO: 9 designed to target the CAP1 gene was prepared by cloning into the HpaI and XhoI restriction enzyme sites of a pLL3.7 lentiviral vector.

```
CAP1 shRNA,
                                  (SEQ ID NO: 9)
5'-AGAUGUGGAUAAGAAGCAU-3'.
```

Figure 7C:
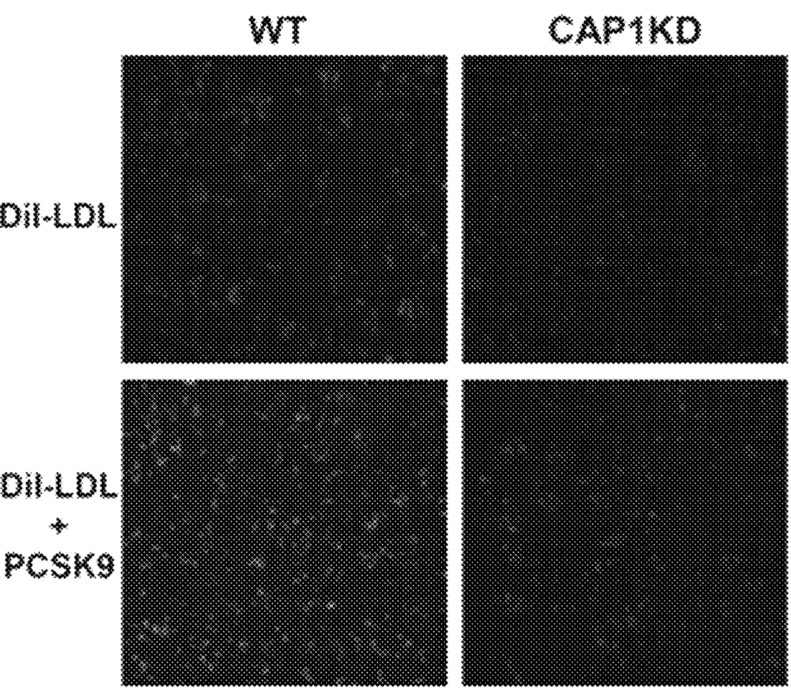
FIG. 7 shows fluorescence microscope images (top) and comparative graphs (bottom) confirming changes in LDL-cholesterol uptake according to knock-down of the CAP1 gene using shRNA in human umbilical vein endothelial cells (HUVECs).
Figure 7C:
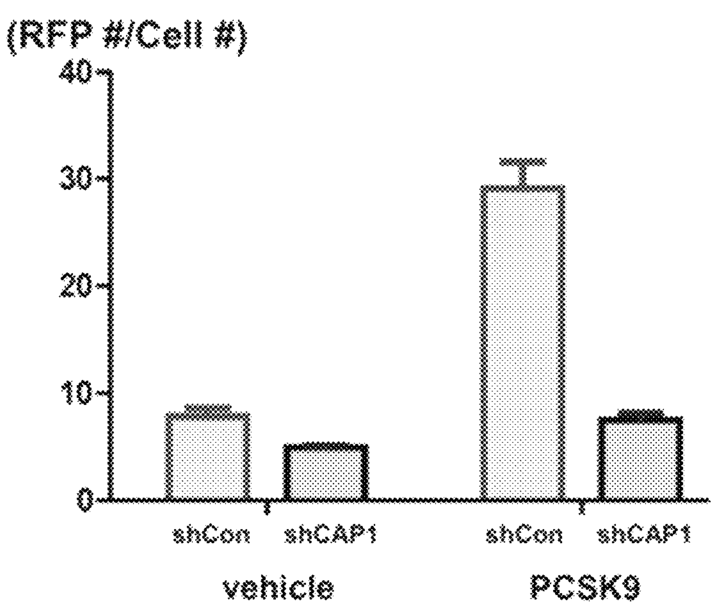

It is known that blood LDL-cholesterol passes through endothelial cells of arterial blood vessels to induce arteriosclerosis. Thus, the present inventors confirmed whether changes in LDL-cholesterol uptake occur when the expression of CAP1 is suppressed using the shCAP1. As a result, as illustrated in FIG. 7, when venous endothelial cells HUVECs were treated with PCSK9, LDL-cholesterol passes through the vascular wall to enter, and in this case, it was found that CAP1-knocked down endothelial cells did not allow LDL-cholesterol to enter the endothelial cells. The results described above suggest that CAP1 plays an important role in the intracellular uptake of LDL-cholesterol capable of inducing arteriosclerosis, and suppression of binding or expression of CAP1 can treat various cardiovascular diseases including arteriosclerosis.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

According to the present invention, cholesterol levels can be regulated by inhibiting the binding of CAP1, which directly binds to PCSK9 to regulate the life cycle of LDL receptors, to PCSK9 or resistin, or suppressing the expression of the CAP1 gene. Therefore, the inhibitor of binding between CAP1 and PCSK9 or resistin or the CAP1 gene expression inhibitor according to the present invention, and the like are expected to have great industrial application values in that they can lower the level of blood cholesterol, and accordingly, can be usefully used as a composition for treating various cardiovascular diseases associated with abnormal levels of blood cholesterol or caused thereby, and furthermore, there is also an effect of reducing inflammation.

The invention claimed is:

1. A method for lowering blood cholesterol comprising administering to a subject in need thereof, a composition comprising, an inhibitor of binding between adenylyl cyclase-associated protein 1 (CAP1) and proprotein convertase subtilisin or kexin type-9 (PCSK9), wherein the inhibitor is selected from SEQ ID NO: 4 and SEQ ID NO: 6, and wherein the inhibitor specifically binds to one or more domains selected from the group consisting of a Src homolog 3 (SH3) binding domain of CAP1 and a cysteine-rich domain (CRD) of PCSK9.

2. The method of claim 1, wherein the SEQ ID NO: 4 is a fusion protein of a CAP1 protein comprising the amino acid sequence of SEQ ID NO:1 and hFc fragment of human immunoglobulin heavy chain; wherein the SEQ ID NO: 6 is a fusion protein of a CAP1 protein comprising the amino acid sequence of SEQ ID NO:1 and mFc fragment of mouse immunoglobulin heavy chain.

3. The method of claim 1, wherein the inhibitor of binding specifically binds to a site comprising 34B aspartic acid present in the SH3 binding domain of CAP1.

4. The method of claim 1, wherein the inhibitor of binding specifically binds to a site comprising lysine 494 present in the M1 domain or arginine 659 present in the M3 domain of PCSK9.

5. The method of claim 1, wherein the composition suppresses degradation of a low-density lipoprotein (LDL) receptor.

6. The method of claim 1, wherein the cholesterol is LDL-cholesterol.

7. A method for treating cardiovascular diseases comprising administering to a subject in need thereof, a pharmaceutical composition comprising:

an inhibitor of binding between adenylyl cyclase-associated protein 1 (CAP1) and proprotein convertase subtilisin or kexin type-9 (PCSK9), wherein the inhibitor is selected from SEQ ID NO:4 and SEQ ID NO:6 and wherein the inhibitor specifically binds to one or more domains selected from the group consisting of a Src homolog 3 (SH3) binding domain of CAP1 and a cysteine-rich domain (CRD) of PCSK9.

8. A method for reducing inflammation comprising administering to a subject in need thereof, a pharmaceutical composition comprising:

an inhibitor of binding between adenylyl cyclase-associated protein 1 (CAP1) and proprotein convertase subtilisin or kexin type-9 (PCSK9), wherein the inhibitor is selected from SEQ ID NO:4 and SEQ ID NO:6 and wherein the inhibitor specifically binds to one or more domains selected from the group consisting of a Src homolog 3 (SH3) binding domain of CAP1 and a cysteine-rich domain (CRD) of PCSK9.

* * * * *

SEQUENCE LISTING

```
<160> NUMBER OF SEQ ID NOS: 13

<210> SEQ ID NO 1
<211> LENGTH: 475
<212> TYPE: PRT
<213> ORGANISM: Homo sapiens

<400> SEQUENCE: 1

Met Ala Asp Met Gln Asn Leu Val Glu Arg Leu Glu Arg Ala Val Gly
1               5                   10                  15

Arg Leu Glu Ala Val Ser His Thr Ser Asp Met His Arg Gly Tyr Ala
            20                  25                  30

Asp Ser Pro Ser Lys Ala Gly Ala Ala Pro Tyr Val Gln Ala Phe Asp
        35                  40                  45

Ser Leu Leu Ala Gly Pro Val Ala Glu Tyr Leu Lys Ile Ser Lys Glu
    50                  55                  60

Ile Gly Gly Asp Val Gln Lys His Ala Glu Met Val His Thr Gly Leu
65                  70                  75                  80

Lys Leu Glu Arg Ala Leu Leu Val Thr Ala Ser Gln Cys Gln Gln Pro
                85                  90                  95

Ala Glu Asn Lys Leu Ser Asp Leu Leu Ala Pro Ile Ser Glu Gln Ile
            100                 105                 110

Lys Glu Val Ile Thr Phe Arg Glu Lys Asn Arg Gly Ser Lys Leu Phe
        115                 120                 125

Asn His Leu Ser Ala Val Ser Glu Ser Ile Gln Ala Leu Gly Trp Val
    130                 135                 140

Ala Met Ala Pro Lys Pro Gly Pro Tyr Val Lys Glu Met Asn Asp Ala
145                 150                 155                 160
```

```
Ala Met Phe Tyr Thr Asn Arg Val Leu Lys Glu Tyr Lys Asp Val Asp
                165                 170                 175

Lys Lys His Val Asp Trp Val Lys Ala Tyr Leu Ser Ile Trp Thr Glu
            180                 185                 190

Leu Gln Ala Tyr Ile Lys Glu Phe His Thr Thr Gly Leu Ala Trp Ser
        195                 200                 205

Lys Thr Gly Pro Val Ala Lys Glu Leu Ser Gly Leu Pro Ser Gly Pro
    210                 215                 220

Ser Ala Gly Ser Gly Pro Pro Pro Pro Pro Pro Gly Pro Pro Pro Pro
225                 230                 235                 240

Pro Val Ser Thr Ser Ser Gly Ser Asp Glu Ser Ala Ser Arg Ser Ala
                245                 250                 255

Leu Phe Ala Gln Ile Asn Gln Gly Glu Ser Ile Thr His Ala Leu Lys
            260                 265                 270

His Val Ser Asp Asp Met Lys Thr His Lys Asn Pro Ala Leu Lys Ala
        275                 280                 285

Gln Ser Gly Pro Val Arg Ser Gly Pro Lys Pro Phe Ser Ala Pro Lys
    290                 295                 300

Pro Gln Thr Ser Pro Ser Pro Lys Arg Ala Thr Lys Lys Glu Pro Ala
305                 310                 315                 320

Val Leu Glu Leu Glu Gly Lys Lys Trp Arg Val Glu Asn Gln Glu Asn
                325                 330                 335

Val Ser Asn Leu Val Ile Glu Asp Thr Glu Leu Lys Gln Val Ala Tyr
            340                 345                 350

Ile Tyr Lys Cys Val Asn Thr Thr Leu Gln Ile Lys Gly Lys Ile Asn
        355                 360                 365

Ser Ile Thr Val Asp Asn Cys Lys Lys Leu Gly Leu Val Phe Asp Asp
    370                 375                 380

Val Val Gly Ile Val Glu Ile Ile Asn Ser Lys Asp Val Lys Val Gln
385                 390                 395                 400

Val Met Gly Lys Val Pro Thr Ile Ser Ile Asn Lys Thr Asp Gly Cys
                405                 410                 415

His Ala Tyr Leu Ser Lys Asn Ser Leu Asp Cys Glu Ile Val Ser Ala
            420                 425                 430

Lys Ser Ser Glu Met Asn Val Leu Ile Pro Thr Glu Gly Gly Asp Phe
        435                 440                 445

Asn Glu Phe Pro Val Pro Glu Gln Phe Lys Thr Leu Trp Asn Gly Gln
    450                 455                 460

Lys Leu Val Thr Thr Val Thr Glu Ile Ala Gly
465                 470                 475


<210> SEQ ID NO 2
<211> LENGTH: 692
<212> TYPE: PRT
<213> ORGANISM: Homo sapiens

<400> SEQUENCE: 2

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
```

```
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480
```

```
Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690


<210> SEQ ID NO 3
<211> LENGTH: 108
<212> TYPE: PRT
<213> ORGANISM: Homo sapiens

<400> SEQUENCE: 3

Met Lys Ala Leu Cys Leu Leu Leu Leu Pro Val Leu Gly Leu Leu Val
1               5                   10                  15

Ser Ser Lys Thr Leu Cys Ser Met Glu Glu Ala Ile Asn Glu Arg Ile
            20                  25                  30

Gln Glu Val Ala Gly Ser Leu Ile Phe Arg Ala Ile Ser Ser Ile Gly
        35                  40                  45

Leu Glu Cys Gln Ser Val Thr Ser Arg Gly Asp Leu Ala Thr Cys Pro
    50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
            100                 105


<210> SEQ ID NO 4
<211> LENGTH: 722
<212> TYPE: PRT
<213> ORGANISM: Artificial Sequence
<220> FEATURE:
<223> OTHER INFORMATION: Amino acid sequence of hFc-CAP1
```

<400> SEQUENCE: 4

```
Met Ala Asp Met Gln Asn Leu Val Glu Arg Leu Glu Arg Ala Val Gly
1               5                   10                  15

Arg Leu Glu Ala Val Ser His Thr Ser Asp Met His Arg Gly Tyr Ala
            20                  25                  30

Asp Ser Pro Ser Lys Ala Gly Ala Ala Pro Tyr Val Gln Ala Phe Asp
        35                  40                  45

Ser Leu Leu Ala Gly Pro Val Ala Glu Tyr Leu Lys Ile Ser Lys Glu
    50                  55                  60

Ile Gly Gly Asp Val Gln Lys His Ala Glu Met Val His Thr Gly Leu
65                  70                  75                  80

Lys Leu Glu Arg Ala Leu Leu Val Thr Ala Ser Gln Cys Gln Gln Pro
                85                  90                  95

Ala Glu Asn Lys Leu Ser Asp Leu Leu Ala Pro Ile Ser Glu Gln Ile
            100                 105                 110

Lys Glu Val Ile Thr Phe Arg Glu Lys Asn Arg Gly Ser Lys Leu Phe
        115                 120                 125

Asn His Leu Ser Ala Val Ser Glu Ser Ile Gln Ala Leu Gly Trp Val
    130                 135                 140

Ala Met Ala Pro Lys Pro Gly Pro Tyr Val Lys Glu Met Asn Asp Ala
145                 150                 155                 160

Ala Met Phe Tyr Thr Asn Arg Val Leu Lys Glu Tyr Lys Asp Val Asp
                165                 170                 175

Lys Lys His Val Asp Trp Val Lys Ala Tyr Leu Ser Ile Trp Thr Glu
            180                 185                 190

Leu Gln Ala Tyr Ile Lys Glu Phe His Thr Thr Gly Leu Ala Trp Ser
        195                 200                 205

Lys Thr Gly Pro Val Ala Lys Glu Leu Ser Gly Leu Pro Ser Gly Pro
    210                 215                 220

Ser Ala Gly Ser Gly Pro Pro Pro Pro Pro Pro Gly Pro Pro Pro Pro
225                 230                 235                 240

Pro Val Ser Thr Ser Ser Gly Ser Asp Glu Ser Ala Ser Arg Ser Ala
                245                 250                 255

Leu Phe Ala Gln Ile Asn Gln Gly Glu Ser Ile Thr His Ala Leu Lys
            260                 265                 270

His Val Ser Asp Asp Met Lys Thr His Lys Asn Pro Ala Leu Lys Ala
        275                 280                 285

Gln Ser Gly Pro Val Arg Ser Gly Pro Lys Pro Phe Ser Ala Pro Lys
    290                 295                 300

Pro Gln Thr Ser Pro Ser Pro Lys Arg Ala Thr Lys Lys Glu Pro Ala
305                 310                 315                 320

Val Leu Glu Leu Glu Gly Lys Lys Trp Arg Val Glu Asn Gln Glu Asn
                325                 330                 335

Val Ser Asn Leu Val Ile Glu Asp Thr Glu Leu Lys Gln Val Ala Tyr
            340                 345                 350

Ile Tyr Lys Cys Val Asn Thr Thr Leu Gln Ile Lys Gly Lys Ile Asn
        355                 360                 365

Ser Ile Thr Val Asp Asn Cys Lys Lys Leu Gly Leu Val Phe Asp Asp
    370                 375                 380

Val Val Gly Ile Val Glu Ile Ile Asn Ser Lys Asp Val Lys Val Gln
385                 390                 395                 400

Val Met Gly Lys Val Pro Thr Ile Ser Ile Asn Lys Thr Asp Gly Cys
```

```
                405                 410                 415

His Ala Tyr Leu Ser Lys Asn Ser Leu Asp Cys Glu Ile Val Ser Ala
            420                 425                 430

Lys Ser Ser Glu Met Asn Val Leu Ile Pro Thr Glu Gly Gly Asp Phe
        435                 440                 445

Asn Glu Phe Pro Val Pro Glu Gln Phe Lys Thr Leu Trp Asn Gly Gln
    450                 455                 460

Lys Leu Val Thr Thr Val Thr Glu Ile Ala Gly Gly Gln Ala Gly Gln
465                 470                 475                 480

Glu Pro Lys Ser Ser Asp Lys Thr His Thr Ser Pro Pro Ser Pro Asp
                485                 490                 495

Lys Thr His Thr Cys Pro Pro Cys Pro Ala Pro Glu Leu Leu Gly Gly
            500                 505                 510

Pro Ser Val Phe Leu Phe Pro Pro Lys Pro Lys Asp Thr Leu Met Ile
        515                 520                 525

Ser Arg Thr Pro Glu Val Thr Cys Val Val Val Asp Val Ser His Glu
    530                 535                 540

Asp Pro Glu Val Lys Phe Asn Trp Tyr Val Asp Gly Val Glu Val His
545                 550                 555                 560

Asn Ala Lys Thr Lys Pro Arg Glu Glu Gln Tyr Asn Ser Thr Tyr Arg
                565                 570                 575

Val Val Ser Val Leu Thr Val Leu His Gln Asp Trp Leu Asn Gly Lys
            580                 585                 590

Glu Tyr Lys Cys Lys Val Ser Asn Lys Ala Leu Pro Ala Pro Ile Glu
        595                 600                 605

Lys Thr Ile Ser Lys Ala Lys Gly Gln Pro Arg Glu Pro Gln Val Tyr
    610                 615                 620

Thr Leu Pro Pro Ser Arg Glu Glu Met Thr Lys Asn Gln Val Ser Leu
625                 630                 635                 640

Thr Cys Leu Val Lys Gly Phe Tyr Pro Ser Asp Ile Ala Val Glu Trp
                645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
        675                 680                 685

Lys Ser Arg Trp Gln Gln Gly Asn Val Phe Ser Cys Ser Val Met His
    690                 695                 700

Glu Ala Leu His Asn His Tyr Thr Gln Lys Ser Leu Ser Leu Ser Pro
705                 710                 715                 720

Gly Lys
```

<210> SEQ ID NO 5
<211> LENGTH: 2166
<212> TYPE: DNA
<213> ORGANISM: Artificial Sequence
<220> FEATURE:
<223> OTHER INFORMATION: DNA sequence of hFc-CAP1

<400> SEQUENCE: 5

```
atggctgaca tgcaaaatct ggtagaaaga ttggagaggg cagtgggccg cctggaggca      60

gtatctcata cctctgacat gcaccgtggg tatgcagaca gtccttcaaa agcaggagca     120

gctccatatg tgcaggcatt tgactcgctg cttgctggtc ctgtggcaga gtacttgaag     180

atcagtaaag agattggggg agacgtgcag aaacatgcgg agatggtcca cacaggtttg     240
```

```
aagttggagc gagctctgtt ggttacagct tctcagtgtc aacagccagc agaaaataag    300
ctttccgatt tgttggcacc catctcagag cagatcaaag aagtgataac ctttcgggag    360
aagaaccgag gcagcaagtt gtttaatcac ctgtcagctg tcagtgaaag tatccaggcc    420
ctgggctggg tggctatggc tcccaagcct ggcccttatg tgaaagaaat gaatgatgcc    480
gccatgtttt atacaaaccg agtcctcaaa gagtacaaag atgtggataa gaagcatgta    540
gactgggtca aagcttattt aagtatatgg acagagctgc aggcttacat taaggagttc    600
cataccaccg gactggcctg gagcaaaacg gggcctgtgg caaaagaact gagcggactg    660
ccatctggac cctctgccgg atcaggtcct cctccccctc caccaggccc ccctcctccc    720
ccagtctcta ccagttcagg ctcagatgag tctgcttccc gctcagcact gttcgcgcag    780
attaatcagg gggagagcat tacacatgcc ctgaaacatg tatctgatga catgaagact    840
cacaagaacc ctgccctgaa ggctcagagt ggtccagtac gcagtggccc caaaccattc    900
tctgcaccta aaccccaaac cagcccatcc cccaaacgag ccacaaagaa ggagccagct    960
gtacttgaac tggagggcaa gaagtggaga gtggaaaatc aggaaaatgt ttccaacctg   1020
gtgattgagg acacagagct gaaacaggtg gcttacatat acaagtgtgt caacacgaca   1080
ttgcaaatca agggcaaaat taactccatt acagtagata actgtaagaa acttggcctg   1140
gtattcgatg acgtggtggg cattgtggag ataatcaaca gtaaggatgt caaagttcag   1200
gtaatgggta aagtgccaac catatccatc aacaaaacag atggctgcca tgcttacctg   1260
agcaagaatt ccctggattg tgaaatagtc agtgccaaat cttccgagat gaatgtcctc   1320
attcctacag aaggcggtga ctttaatgaa ttcccagttc ctgagcagtt caagacccta   1380
tggaacgggc agaagttggt caccacagtg acagaaattg ctggaggcca ggccggccag   1440
gagcccaaat ctagcgacaa aactcacaca agcccaccga gcccagacaa aactcacaca   1500
tgcccaccgt gcccagcacc tgaactcctg gggggaccgt cagtcttcct cttcccccca   1560
aaacccaagg acaccctcat gatctcccgg acccctgagg tcacatgcgt ggtggtggac   1620
gtgagccacg aagaccctga ggtcaagttc aactggtacg tggacggcgt ggaggtgcat   1680
aatgccaaga caaagccgcg ggaggagcag tacaacagca cgtaccgtgt ggtcagcgtc   1740
ctcaccgtcc tgcaccagga ctggctgaat ggcaaggagt acaagtgcaa ggtctccaac   1800
aaagccctcc cagcccccat cgagaaaacc atctccaaag ccaaagggca gccccgagaa   1860
ccacaggtgt acaccctgcc cccatcccgg gaggagatga ccaagaacca ggtcagcctg   1920
acctgcctgg tcaaaggctt ctatcccagc gacatcgccg tggagtggga gagcaatggg   1980
cagccggaga acaactacaa gaccacgcct cccgtgctgg actccgacgg ctccttcttc   2040
ctctacagca agctcaccgt ggacaagagc aggtggcagc aggggaacgt cttctcatgc   2100
tccgtgatgc acgaggctct gcacaaccac tacacgcaga agagcctctc cctgtctccg   2160
ggtaaa                                                              2166
```

```
<210> SEQ ID NO 6
<211> LENGTH: 709
<212> TYPE: PRT
<213> ORGANISM: Artificial Sequence
<220> FEATURE:
<223> OTHER INFORMATION: Amino acid sequence of mFc-CAP1

<400> SEQUENCE: 6

Met Ala Asp Met Gln Asn Leu Val Glu Arg Leu Glu Arg Ala Val Gly
1               5                   10                  15
```

-continued

```
Arg Leu Glu Ala Val Ser His Thr Ser Asp Met His Arg Gly Tyr Ala
            20                  25                  30

Asp Ser Pro Ser Lys Ala Gly Ala Ala Pro Tyr Val Gln Ala Phe Asp
        35                  40                  45

Ser Leu Leu Ala Gly Pro Val Ala Glu Tyr Leu Lys Ile Ser Lys Glu
    50                  55                  60

Ile Gly Gly Asp Val Gln Lys His Ala Glu Met Val His Thr Gly Leu
65                  70                  75                  80

Lys Leu Glu Arg Ala Leu Leu Val Thr Ala Ser Gln Cys Gln Gln Pro
                85                  90                  95

Ala Glu Asn Lys Leu Ser Asp Leu Leu Ala Pro Ile Ser Glu Gln Ile
            100                 105                 110

Lys Glu Val Ile Thr Phe Arg Glu Lys Asn Arg Gly Ser Lys Leu Phe
        115                 120                 125

Asn His Leu Ser Ala Val Ser Glu Ser Ile Gln Ala Leu Gly Trp Val
    130                 135                 140

Ala Met Ala Pro Lys Pro Gly Pro Tyr Val Lys Glu Met Asn Asp Ala
145                 150                 155                 160

Ala Met Phe Tyr Thr Asn Arg Val Leu Lys Glu Tyr Lys Asp Val Asp
                165                 170                 175

Lys Lys His Val Asp Trp Val Lys Ala Tyr Leu Ser Ile Trp Thr Glu
            180                 185                 190

Leu Gln Ala Tyr Ile Lys Glu Phe His Thr Thr Gly Leu Ala Trp Ser
        195                 200                 205

Lys Thr Gly Pro Val Ala Lys Glu Leu Ser Gly Leu Pro Ser Gly Pro
    210                 215                 220

Ser Ala Gly Ser Gly Pro Pro Pro Pro Pro Pro Gly Pro Pro Pro Pro
225                 230                 235                 240

Pro Val Ser Thr Ser Ser Gly Ser Asp Glu Ser Ala Ser Arg Ser Ala
                245                 250                 255

Leu Phe Ala Gln Ile Asn Gln Gly Glu Ser Ile Thr His Ala Leu Lys
            260                 265                 270

His Val Ser Asp Asp Met Lys Thr His Lys Asn Pro Ala Leu Lys Ala
        275                 280                 285

Gln Ser Gly Pro Val Arg Ser Gly Pro Lys Pro Phe Ser Ala Pro Lys
    290                 295                 300

Pro Gln Thr Ser Pro Ser Pro Lys Arg Ala Thr Lys Lys Glu Pro Ala
305                 310                 315                 320

Val Leu Glu Leu Glu Gly Lys Lys Trp Arg Val Glu Asn Gln Glu Asn
                325                 330                 335

Val Ser Asn Leu Val Ile Glu Asp Thr Glu Leu Lys Gln Val Ala Tyr
            340                 345                 350

Ile Tyr Lys Cys Val Asn Thr Thr Leu Gln Ile Lys Gly Lys Ile Asn
        355                 360                 365

Ser Ile Thr Val Asp Asn Cys Lys Lys Leu Gly Leu Val Phe Asp Asp
    370                 375                 380

Val Val Gly Ile Val Glu Ile Ile Asn Ser Lys Asp Val Lys Val Gln
385                 390                 395                 400

Val Met Gly Lys Val Pro Thr Ile Ser Ile Asn Lys Thr Asp Gly Cys
                405                 410                 415

His Ala Tyr Leu Ser Lys Asn Ser Leu Asp Cys Glu Ile Val Ser Ala
            420                 425                 430

Lys Ser Ser Glu Met Asn Val Leu Ile Pro Thr Glu Gly Gly Asp Phe
```

```
        435                 440                 445

Asn Glu Phe Pro Val Pro Glu Gln Phe Lys Thr Leu Trp Asn Gly Gln
    450                 455                 460

Lys Leu Val Thr Thr Val Thr Glu Ile Ala Gly Gly Gln Ala Gly Gln
465                 470                 475                 480

Glu Pro Lys Ser Ser Asp Lys Thr His Thr Ser Pro Pro Ser Pro Val
                485                 490                 495

Pro Glu Val Ser Ser Val Phe Ile Phe Pro Pro Lys Pro Lys Asp Val
            500                 505                 510

Leu Thr Ile Thr Leu Thr Pro Lys Val Thr Cys Val Val Val Asp Ile
        515                 520                 525

Ser Lys Asp Asp Pro Glu Val Gln Phe Ser Trp Phe Val Asp Asp Val
    530                 535                 540

Glu Val His Thr Ala Gln Thr Gln Pro Arg Glu Glu Gln Phe Asn Ser
545                 550                 555                 560

Thr Phe Arg Ser Val Ser Glu Leu Pro Ile Met His Gln Asp Trp Leu
                565                 570                 575

Asn Gly Lys Glu Phe Lys Cys Arg Val Asn Ser Ala Ala Phe Pro Ala
            580                 585                 590

Pro Ile Glu Lys Thr Ile Ser Lys Thr Lys Gly Arg Pro Lys Ala Pro
        595                 600                 605

Gln Val Tyr Thr Ile Pro Pro Pro Lys Glu Gln Met Ala Lys Asp Lys
    610                 615                 620

Val Ser Leu Thr Cys Met Ile Thr Asp Phe Phe Pro Glu Asp Ile Thr
625                 630                 635                 640

Val Glu Trp Gln Trp Asn Gly Gln Pro Ala Glu Asn Tyr Lys Asn Thr
                645                 650                 655

Gln Pro Ile Met Asp Thr Asp Gly Ser Tyr Phe Val Tyr Ser Lys Leu
            660                 665                 670

Asn Val Gln Lys Ser Asn Trp Glu Ala Gly Asn Thr Phe Thr Cys Ser
        675                 680                 685

Val Leu His Glu Gly Leu His Asn His His Thr Glu Lys Ser Leu Ser
    690                 695                 700

His Ser Pro Gly Lys
705


<210> SEQ ID NO 7
<211> LENGTH: 2130
<212> TYPE: DNA
<213> ORGANISM: Artificial Sequence
<220> FEATURE:
<223> OTHER INFORMATION: DNA sequence of mFc-CAP1

<400> SEQUENCE: 7

atggctgaca tgcaaaatct ggtagaaaga ttggagaggg cagtgggccg cctggaggca      60

gtatctcata cctctgacat gcaccgtggg tatgcagaca gtccttcaaa agcaggagca     120

gctccatatg tgcaggcatt tgactcgctg cttgctggtc ctgtggcaga gtacttgaag     180

atcagtaaag agattggggg agacgtgcag aaacatgcgg agatggtcca cacaggtttg     240

aagttggagc gagctctgtt ggttacagct tctcagtgtc aacagccagc agaaaataag     300

ctttccgatt tgttggcacc catctcagag cagatcaaag aagtgataac ctttcgggag     360

aagaaccgag gcagcaagtt gtttaatcac ctgtcagctg tcagtgaaag tatccaggcc     420

ctgggctggg tggctatggc tcccaagcct ggcccttatg tgaaagaaat gaatgatgcc     480
```

-continued

```
gccatgtttt atacaaaccg agtcctcaaa gagtacaaag atgtggataa gaagcatgta    540

gactgggtca aagcttattt aagtatatgg acagagctgc aggcttacat taaggagttc    600

cataccaccg gactggcctg gagcaaaacg gggcctgtgg caaaagaact gagcggactg    660

ccatctggac cctctgccgg atcaggtcct cctccccctc caccaggccc ccctcctccc    720

ccagtctcta ccagttcagg ctcagatgag tctgcttccc gctcagcact gttcgcgcag    780

attaatcagg gggagagcat tacacatgcc ctgaaacatg tatctgatga catgaagact    840

cacaagaacc ctgccctgaa ggctcagagt ggtccagtac gcagtggccc caaaccattc    900

tctgcaccta aaccccaaac cagcccatcc cccaaacgag ccacaaagaa ggagccagct    960

gtacttgaac tggagggcaa gaagtggaga gtggaaaatc aggaaaatgt ttccaacctg   1020

gtgattgagg acacagagct gaaacaggtg gcttacatat acaagtgtgt caacacgaca   1080

ttgcaaatca agggcaaaat taactccatt acagtagata actgtaagaa acttggcctg   1140

gtattcgatg acgtggtggg cattgtggag ataatcaaca gtaaggatgt caaagttcag   1200

gtaatgggta aagtgccaac catatccatc aacaaaacag atggctgcca tgcttacctg   1260

agcaagaatt ccctggattg tgaaatagtc agtgccaaat cttccgagat gaatgtcctc   1320

attcctacag aaggcggtga ctttaatgaa ttcccagttc ctgagcagtt caagacccta   1380

tggaacgggc agaagttggt caccacagtg acagaaattg ctggaggcca ggccggccag   1440

gagcccaaat ctagcgacaa aactcacaca agcccaccga gcccagtccc agaagtatca   1500

tctgtcttca tcttcccccc aaagcccaag gatgtgctca ccattactct gactcctaag   1560

gtcacgtgtg ttgtggtaga catcagcaag gatgatcccg aggtccagtt cagctggttt   1620

gtagatgatg tggaggtgca cacagctcag acgcaacccc gggaggagca gttcaacagc   1680

actttccgct cagtcagtga acttcccatc atgcaccagg actggctcaa tggcaaggag   1740

ttcaaatgca gggtcaacag tgcagctttc cctgccccca tcgagaaaac catctccaaa   1800

accaaaggca gaccgaaggc tccacaggtg tacaccattc cacctcccaa ggagcagatg   1860

gccaaggata aagtcagtct gacctgcatg ataacagact tcttccctga agacattact   1920

gtggagtggc agtggaatgg gcagccagcg gagaactaca agaacactca gcccatcatg   1980

gacacagatg gctcttactt cgtctacagc aagctcaatg tgcagaagag caactgggag   2040

gcaggaaata ctttcacctg ctctgtgtta catgagggcc tgcacaacca ccatactgag   2100

aagagcctct cccactctcc tggtaaatga                                    2130
```

<210> SEQ ID NO 8
<211> LENGTH: 21
<212> TYPE: RNA
<213> ORGANISM: Artificial Sequence
<220> FEATURE:
<223> OTHER INFORMATION: siRNA sequence for CAP1

<400> SEQUENCE: 8

```
aaaccgaguc cucaaagagu a                                               21
```

<210> SEQ ID NO 9
<211> LENGTH: 19
<212> TYPE: RNA
<213> ORGANISM: Artificial Sequence
<220> FEATURE:
<223> OTHER INFORMATION: shRNA sequence for CAP1

<400> SEQUENCE: 9

```
agauguggau aagaagcau                                                  19
```

<210> SEQ ID NO 10
<211> LENGTH: 126
<212> TYPE: PRT
<213> ORGANISM: Artificial Sequence
<220> FEATURE:
<223> OTHER INFORMATION: Amino acid sequence of CAP1 SH3 binding domain

<400> SEQUENCE: 10

```
Leu Ala Trp Ser Lys Thr Gly Pro Val Ala Lys Glu Leu Ser Gly Leu
1               5                   10                  15

Pro Ser Gly Pro Ser Ala Gly Ser Gly Pro Pro Pro Pro Pro Pro Gly
            20                  25                  30

Pro Pro Pro Pro Pro Val Ser Thr Ser Ser Gly Ser Asp Glu Ser Ala
        35                  40                  45

Ser Arg Ser Ala Leu Phe Ala Gln Ile Asn Gln Gly Glu Ser Ile Thr
    50                  55                  60

His Ala Leu Lys His Val Ser Asp Asp Met Lys Thr His Lys Asn Pro
65                  70                  75                  80

Ala Leu Lys Ala Gln Ser Gly Pro Val Arg Ser Gly Pro Lys Pro Phe
                85                  90                  95

Ser Ala Pro Lys Pro Gln Thr Ser Pro Ser Pro Lys Arg Ala Thr Lys
            100                 105                 110

Lys Glu Pro Ala Val Leu Glu Leu Glu Gly Lys Lys Trp Arg
        115                 120                 125
```

<210> SEQ ID NO 11
<211> LENGTH: 272
<212> TYPE: PRT
<213> ORGANISM: Homo sapiens
<220> FEATURE:
<221> NAME/KEY: DOMAIN
<222> LOCATION: (1)..(272)
<223> OTHER INFORMATION: cystein-rich domain

<400> SEQUENCE: 11

```
Lys Asp Val Ile Asn Glu Ala Trp Phe Pro Glu Asp Gln Arg Val Leu
1               5                   10                  15

Thr Pro Asn Leu Val Ala Ala Leu Pro Pro Ser Thr His Gly Ala Gly
            20                  25                  30

Trp Gln Leu Phe Cys Arg Thr Val Trp Ser Ala His Ser Gly Pro Thr
        35                  40                  45

Arg Met Ala Thr Ala Val Ala Arg Cys Ala Pro Asp Glu Glu Leu Leu
    50                  55                  60

Ser Cys Ser Ser Phe Ser Arg Ser Gly Lys Arg Arg Gly Glu Arg Met
65                  70                  75                  80

Glu Ala Gln Gly Gly Lys Leu Val Cys Arg Ala His Asn Ala Phe Gly
                85                  90                  95

Gly Glu Gly Val Tyr Ala Ile Ala Arg Cys Cys Leu Leu Pro Gln Ala
            100                 105                 110

Asn Cys Ser Val His Thr Ala Pro Pro Ala Glu Ala Ser Met Gly Thr
        115                 120                 125

Arg Val His Cys His Gln Gln Gly His Val Leu Thr Gly Cys Ser Ser
    130                 135                 140

His Trp Glu Val Glu Asp Leu Gly Thr His Lys Pro Pro Val Leu Arg
145                 150                 155                 160

Pro Arg Gly Gln Pro Asn Gln Cys Val Gly His Arg Glu Ala Ser Ile
                165                 170                 175
```

```
His Ala Ser Cys Cys His Ala Pro Gly Leu Glu Cys Lys Val Lys Glu
            180                 185                 190

His Gly Ile Pro Ala Pro Gln Glu Gln Val Thr Val Ala Cys Glu Glu
        195                 200                 205

Gly Trp Thr Leu Thr Gly Cys Ser Ala Leu Pro Gly Thr Ser His Val
    210                 215                 220

Leu Gly Ala Tyr Ala Val Asp Asn Thr Cys Val Val Arg Ser Arg Asp
225                 230                 235                 240

Val Ser Thr Thr Gly Ser Thr Ser Glu Gly Ala Val Thr Ala Val Ala
                245                 250                 255

Ile Cys Cys Arg Ser Arg His Leu Ala Gln Ala Ser Gln Glu Leu Gln
            260                 265                 270


<210> SEQ ID NO 12
<211> LENGTH: 79
<212> TYPE: PRT
<213> ORGANISM: Homo sapiens
<220> FEATURE:
<221> NAME/KEY: DOMAIN
<222> LOCATION: (1)..(79)
<223> OTHER INFORMATION: M1 domain

<400> SEQUENCE: 12

Trp Gln Leu Phe Cys Arg Thr Val Trp Ser Ala His Ser Gly Pro Thr
1               5                   10                  15

Arg Met Ala Thr Ala Val Ala Arg Cys Ala Pro Asp Glu Glu Leu Leu
            20                  25                  30

Ser Cys Ser Ser Phe Ser Arg Ser Gly Lys Arg Arg Gly Glu Arg Met
        35                  40                  45

Glu Ala Gln Gly Gly Lys Leu Val Cys Arg Ala His Asn Ala Phe Gly
    50                  55                  60

Gly Glu Gly Val Tyr Ala Ile Ala Arg Cys Cys Leu Leu Pro Gln
65                  70                  75


<210> SEQ ID NO 13
<211> LENGTH: 89
<212> TYPE: PRT
<213> ORGANISM: Homo sapiens
<220> FEATURE:
<221> NAME/KEY: DOMAIN
<222> LOCATION: (1)..(89)
<223> OTHER INFORMATION: M3 domain

<400> SEQUENCE: 13

Pro Gly Leu Glu Cys Lys Val Lys Glu His Gly Ile Pro Ala Pro Gln
1               5                   10                  15

Glu Gln Val Thr Val Ala Cys Glu Glu Gly Trp Thr Leu Thr Gly Cys
            20                  25                  30

Ser Ala Leu Pro Gly Thr Ser His Val Leu Gly Ala Tyr Ala Val Asp
        35                  40                  45

Asn Thr Cys Val Val Arg Ser Arg Asp Val Ser Thr Thr Gly Ser Thr
    50                  55                  60

Ser Glu Gly Ala Val Thr Ala Val Ala Ile Cys Cys Arg Ser Arg His
65                  70                  75                  80

Leu Ala Gln Ala Ser Gln Glu Leu Gln
                85
```